(12) United States Patent
MacHold et al.

(10) Patent No.: US 7,879,077 B2
(45) Date of Patent: *Feb. 1, 2011

(54) METHOD AND SYSTEM FOR CONTROL OF A PATIENT'S BODY TEMPERATURE BY WAY OF A TRANSLUMINALLY INSERTABLE HEAT EXCHANGE CATHETER

(75) Inventors: Timothy R. MacHold, Moss Beach, CA (US); Wade A. Keller, San Jose, CA (US); Alex T. Roth, Redwood City, CA (US); Nicole Denise Bloom, San Francisco, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 760 days.

This patent is subject to a terminal disclaimer.

(21) Appl. No.: 11/674,119

(22) Filed: Feb. 12, 2007

(65) Prior Publication Data

US 2007/0203552 A1  Aug. 30, 2007

Related U.S. Application Data

(60) Continuation of application No. 10/645,891, filed on Aug. 20, 2003, now Pat. No. 7,175,649, which is a division of application No. 09/707,257, filed on Nov. 6, 2000, now Pat. No. 6,620,189, which is a continuation-in-part of application No. 09/563,946, filed on May 2, 2000, now Pat. No. 6,673,098.

(60) Provisional application No. 60/219,922, filed on Jul. 21, 2000, provisional application No. 60/185,561, filed on Feb. 28, 2000.

(51) Int. Cl.
*A61F 7/00* (2006.01)
(52) U.S. Cl. ........................... 607/96; 607/113; 607/114
(58) Field of Classification Search ....................... None
See application file for complete search history.

(56) References Cited

U.S. PATENT DOCUMENTS 2,308,484 A  1/1943  Auzin et al.

(Continued)

FOREIGN PATENT DOCUMENTS

AU       730835       3/2001

(Continued)

OTHER PUBLICATIONS

European Patent Office Search Report dated Jul. 20, 2007.

*Primary Examiner*—Robert L Nasser
(74) *Attorney, Agent, or Firm*—John K. Fitzgerald; Fulwider Patton LLP

(57) ABSTRACT

Methods and apparatuses for temperature modification of a patient, or selected regions thereof, including an induced state of hypothermia. The temperature modification is accomplished using an in-dwelling heat exchange catheter within which a fluid heat exchange medium circulates. A heat exchange cassette of any one of several disclosed variations is attached to the circulatory conduits of the catheter, the heat exchange cassette being sized to engage a cavity within one of various described re-usable control units. The control units include a heater/cooler device, a user input device, and a processor connected to receive input from various sensors around the body and the system. The heater/cooler device may be thermoelectric to enable both heating and 15" cooling based on polarity. A temperature control scheme for ramping the body temperature up or down without overshoot is provided. The disposable heat exchange cassettes may include an integral pump head that engages with a pump drive mechanism within the re-usable control unit. More than one control unit may be provided to receive the same heat exchange cassette so that, for example, a large capacity control unit can be used initially, and a smaller, battery-powered unit can be substituted once the patient reaches the desired target temperature.

3 Claims, 36 Drawing Sheets

U.S. PATENT DOCUMENTS

| | | |
|---|---|---|
| 3,369,549 A | 2/1968 | Armao |
| 3,425,419 A | 2/1969 | Dato |
| 3,726,283 A | 4/1973 | Dye et al. |
| 3,788,328 A | 1/1974 | Alley et al. |
| 3,995,617 A | 12/1976 | Watkins et al. |
| 4,014,317 A | 3/1977 | Bruno |
| 4,038,519 A | 7/1977 | Foucras |
| 4,111,209 A | 9/1978 | Wolvek et al. |
| 4,246,932 A | 1/1981 | Raines |
| 4,298,006 A | 11/1981 | Parks |
| 4,393,863 A | 7/1983 | Osterholm |
| 4,445,514 A | 5/1984 | Osterholm |
| 4,445,887 A | 5/1984 | Osterholm |
| 4,445,888 A | 5/1984 | Osterholm |
| 4,446,154 A | 5/1984 | Osterholm |
| 4,446,155 A | 5/1984 | Osterholm |
| 4,450,841 A | 5/1984 | Osterholm |
| 4,451,251 A | 5/1984 | Osterholm |
| 4,470,407 A | 9/1984 | Hussein |
| 4,540,402 A | 9/1985 | Aigner |
| 4,657,532 A | 4/1987 | Osterholm |
| 4,661,094 A | 4/1987 | Simpson |
| 4,662,383 A | 5/1987 | Sogawa et al. |
| 4,672,962 A | 6/1987 | Hershenson |
| 4,686,085 A | 8/1987 | Osterholm |
| 4,701,166 A | 10/1987 | Groshong et al. |
| 4,705,501 A | 11/1987 | Wigness et al. |
| 4,748,979 A | 6/1988 | Hershenson |
| 4,754,752 A | 7/1988 | Ginsburg et al. |
| 4,758,431 A | 7/1988 | Osterholm |
| 4,769,005 A | 9/1988 | Ginsburg et al. |
| 4,795,423 A | 1/1989 | Osterholm |
| 4,804,358 A | 2/1989 | Karcher et al. |
| 4,819,655 A | 4/1989 | Webler |
| 4,830,849 A | 5/1989 | Osterholm |
| 4,857,054 A | 8/1989 | Helfer |
| 4,873,978 A | 10/1989 | Ginsburg |
| 4,892,095 A | 1/1990 | Nakhgevany |
| 4,892,519 A | 1/1990 | Songer et al. |
| 4,899,741 A | 2/1990 | Bentley et al. |
| 4,909,252 A | 3/1990 | Goldberger |
| 4,919,134 A | 4/1990 | Streeter |
| 4,920,963 A | 5/1990 | Brader |
| 4,941,475 A | 7/1990 | Williams et al. |
| 4,960,103 A | 10/1990 | Urso |
| 4,962,761 A | 10/1990 | Golden |
| 4,963,130 A | 10/1990 | Osterholm |
| 4,976,691 A | 12/1990 | Sahota |
| 4,981,691 A | 1/1991 | Osterholm et al. |
| 4,995,863 A | 2/1991 | Nichols et al. |
| 5,011,488 A | 4/1991 | Ginsburg |
| 5,019,075 A | 5/1991 | Spears et al. |
| 5,030,210 A | 7/1991 | Alchas |
| 5,041,089 A | 8/1991 | Mueller et al. |
| 5,085,630 A | 2/1992 | Osterholm et al. |
| 5,092,841 A | 3/1992 | Spears |
| 5,097,829 A | 3/1992 | Quisenberry |
| 5,106,360 A | 4/1992 | Ishiwara et al. |
| 5,112,301 A | 5/1992 | Fenton, Jr. et al. |
| 5,147,385 A | 9/1992 | Beck et al. |
| 5,149,321 A | 9/1992 | Klatz et al. |
| 5,151,100 A | 9/1992 | Abele et al. |
| 5,174,285 A | 12/1992 | Fontenot |
| 5,180,364 A | 1/1993 | Ginsburg |
| 5,191,883 A | 3/1993 | Lennox et al. |
| 5,196,024 A | 3/1993 | Barath |
| 5,211,631 A | 5/1993 | Sheaff |
| 5,216,032 A | 6/1993 | Manning |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,261,399 A | 11/1993 | Klatz et al. |
| 5,269,758 A | 12/1993 | Taheri |
| 5,334,181 A | 8/1994 | Rubinsky et al. |
| 5,342,301 A | 8/1994 | Saab |
| 5,344,436 A | 9/1994 | Fontenot et al. |
| 5,368,591 A | 11/1994 | Lennox et al. |
| 5,395,314 A | 3/1995 | Klatz et al. |
| 5,403,281 A | 4/1995 | O'Neill et al. |
| 5,437,633 A | 8/1995 | Manning |
| 5,437,673 A | 8/1995 | Baust et al. |
| 5,486,208 A | 1/1996 | Ginsburg |
| 5,514,094 A | 5/1996 | Anello et al. |
| 5,531,776 A | 7/1996 | Ward et al. |
| 5,563,584 A | 10/1996 | Rader et al. |
| 5,584,804 A | 12/1996 | Klatz et al. |
| 5,624,392 A | 4/1997 | Saab |
| 5,645,531 A | 7/1997 | Thompson et al. |
| 5,653,692 A | 8/1997 | Masterson et al. |
| 5,676,691 A | 10/1997 | Friedman |
| 5,678,570 A | 10/1997 | Manning |
| 5,716,386 A | 2/1998 | Ward et al. |
| 5,733,319 A | 3/1998 | Neilson et al. |
| 5,837,003 A | 11/1998 | Ginsburg |
| 5,871,526 A | 2/1999 | Gibbs et al. |
| 5,957,963 A | 9/1999 | Dobak, III |
| 5,972,013 A | 10/1999 | Schmidt |
| 5,980,561 A | 11/1999 | Kolen et al. |
| 6,019,783 A | 2/2000 | Phillips et al. |
| 6,042,559 A | 3/2000 | Dobak, III |
| 6,051,019 A | 4/2000 | Dobak, III |
| 6,096,068 A | 8/2000 | Dobak, III et al. |
| 6,126,684 A | 10/2000 | Gobin et al. |
| 6,146,411 A | 11/2000 | Noda et al. |
| 6,149,670 A | 11/2000 | Worthen et al. |
| 6,149,676 A | 11/2000 | Ginsburg |
| 6,149,677 A | 11/2000 | Dobak, III |
| 6,206,004 B1 | 3/2001 | Schmidt et al. |
| 6,224,624 B1 | 5/2001 | Lasheras et al. |
| 6,231,595 B1 | 5/2001 | Dobak, III |
| 6,235,048 B1 | 5/2001 | Dobak, III |
| 6,245,095 B1 | 6/2001 | Dobak, III et al. |
| 6,251,129 B1 | 6/2001 | Dobak, III et al. |
| 6,254,626 B1 | 7/2001 | Dobak, III et al. |
| 6,261,312 B1 | 7/2001 | Dobak, III et al. |
| 6,287,326 B1 | 9/2001 | Pecor |
| 6,290,717 B1 | 9/2001 | Philips |
| 6,299,599 B1 | 10/2001 | Pham et al. |
| 6,312,452 B1 | 11/2001 | Dobak, III et al. |
| 6,338,727 B1 | 1/2002 | Noda et al. |
| 6,375,674 B1 | 4/2002 | Carson |
| 7,175,649 B2 * | 2/2007 | Machold et al. ............. 607/104 |

FOREIGN PATENT DOCUMENTS

| | | |
|---|---|---|
| AU | 756115 | 1/2003 |
| AU | 772661 | 5/2004 |
| WO | 94/17842 A1 | 8/1994 |
| WO | 97/39707 A1 | 10/1997 |
| WO | 00/09054 A1 | 2/2000 |
| WO | 00/38601 A1 | 7/2000 |
| WO | 00/48670 A1 | 8/2000 |
| WO | 00/66053 A1 | 11/2000 |

\* cited by examiner

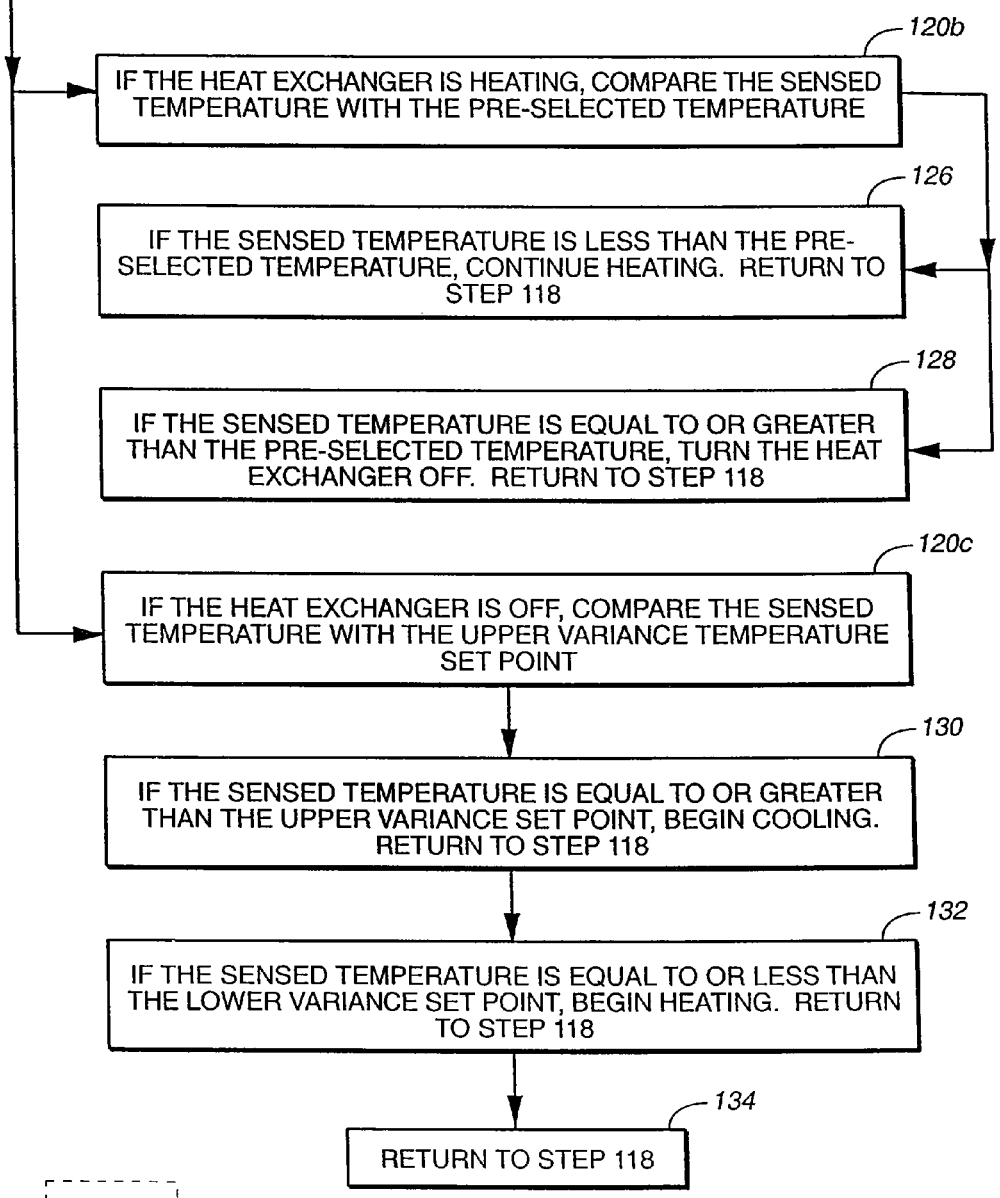

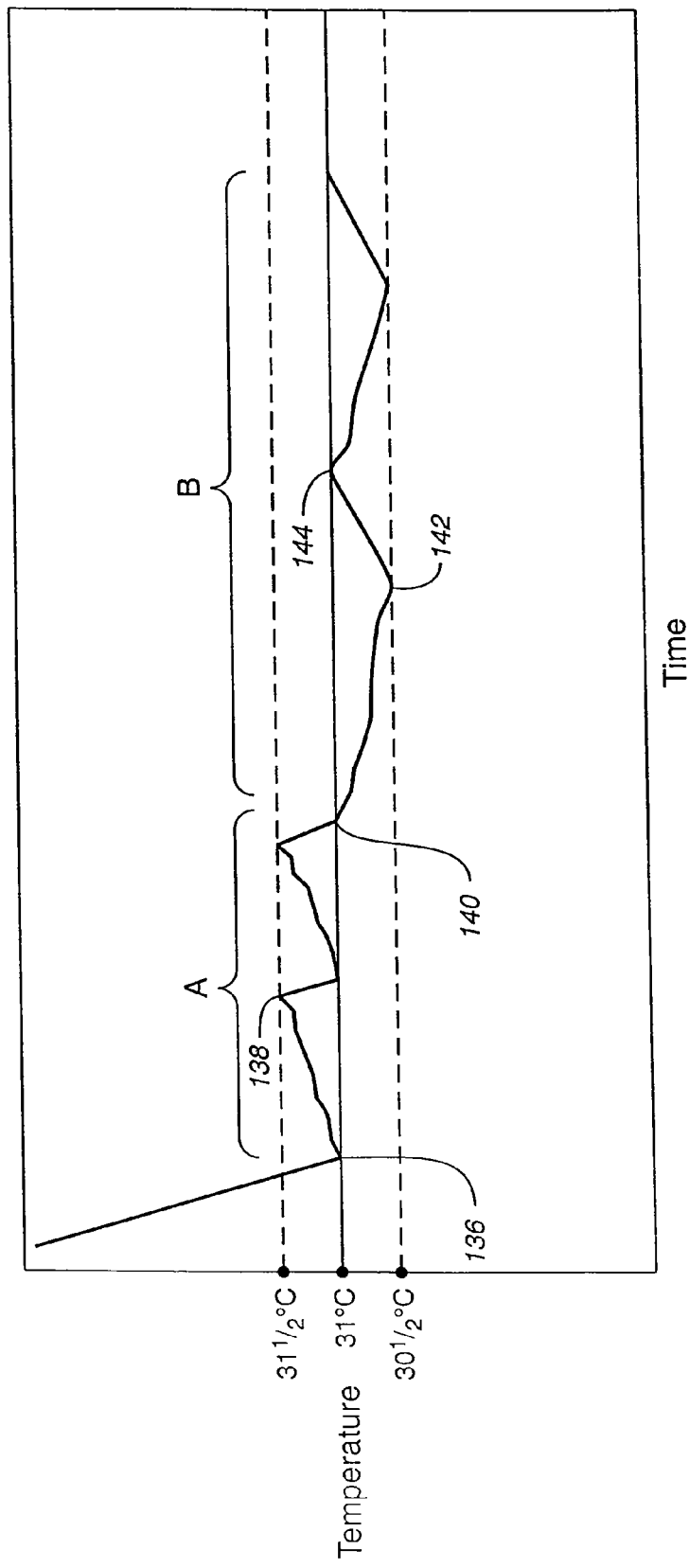

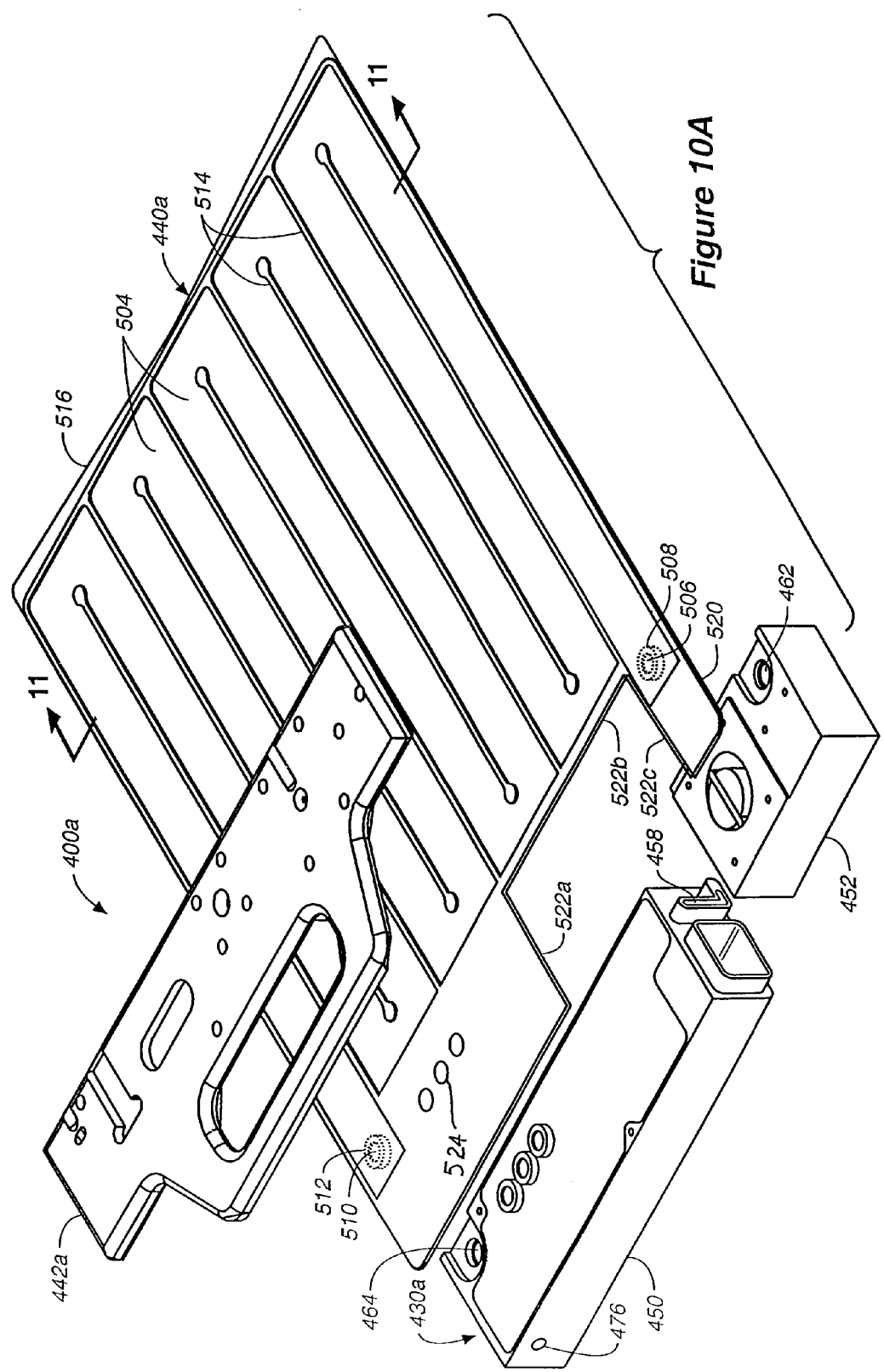

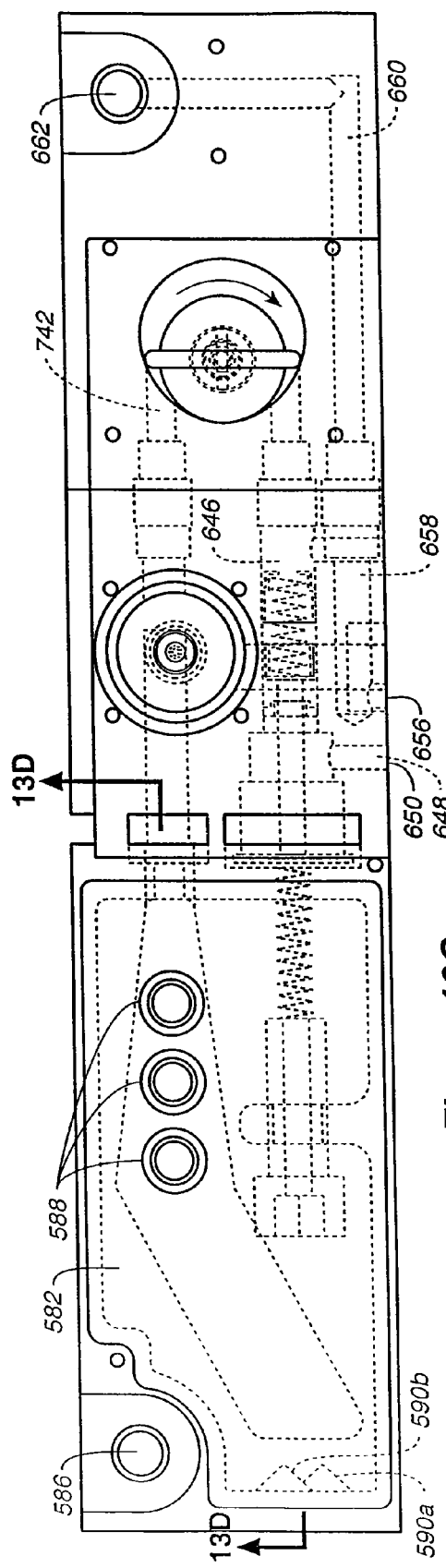
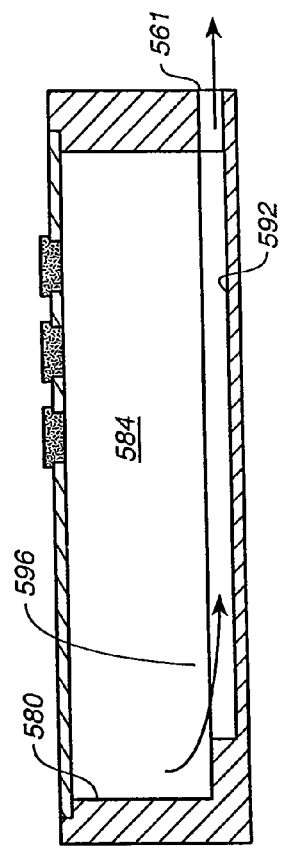
*Figure 13C*
*Figure 13D*

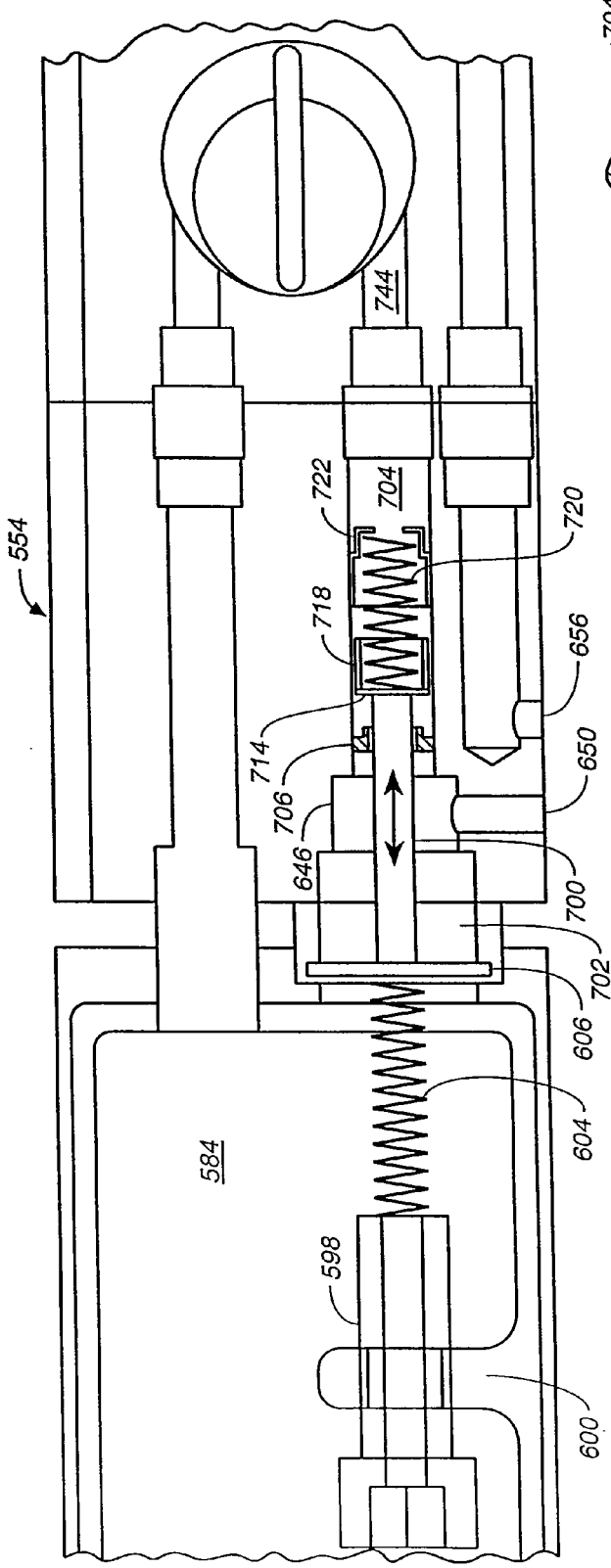
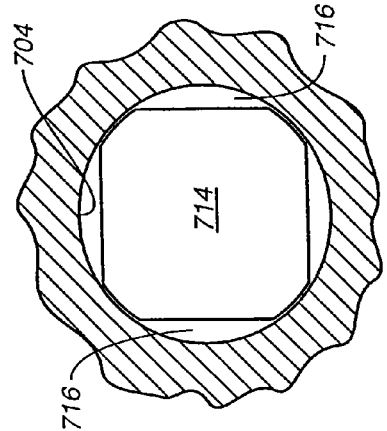
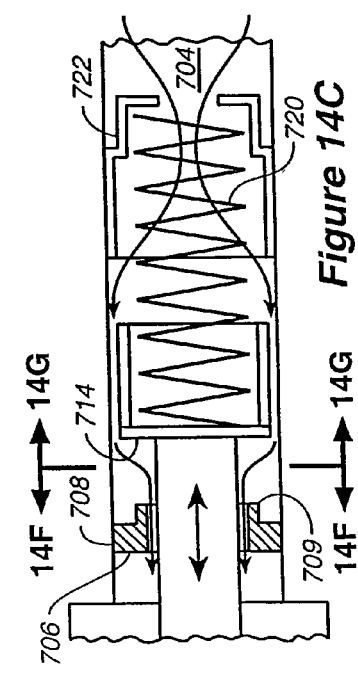
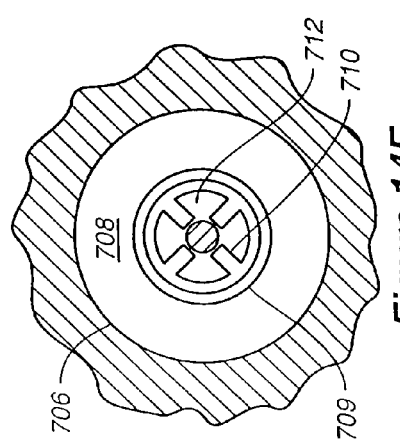
Figure 14B
Figure 14C
Figure 14G
Figure 14F

METHOD AND SYSTEM FOR CONTROL OF A PATIENT'S BODY TEMPERATURE BY WAY OF A TRANSLUMINALLY INSERTABLE HEAT EXCHANGE CATHETER

RELATED APPLICATIONS

This application is a continuation of U.S. application Ser. No. 10/645,891, filed Aug. 20, 2003, now U.S. Pat. No. 7,175,649, which is a divisional application of U.S. application Ser. No. 09/707,257, filed Nov. 6, 2000, now U.S. Pat. No. 6,620,189 B1, which is a continuation-in-part of U.S. application Ser. No. 09/563,946, filed May 2, 2000, now U.S. Pat. No. 6,673,098 which claims the benefit of U.S. provisional application Ser. No. 60/219,922, filed Jul. 21, 2000, and also claims the benefit of U.S. provisional application Ser. No. 60/185,561, filed Feb. 28, 2000, the entire contents of which are incorporated herein by reference.

FIELD OF THE INVENTION

The present invention relates generally to medical devices and methods and, more particularly, to a programmable, microprocessor based controller and method for controlling the temperature and flow of a thermal exchange fluid that is circulated through a heat exchange catheter inserted into a patient's body for the purpose or cooling or warming at least a portion of the patient's body.

BACKGROUND OF THE INVENTION

Under ordinary circumstances, the thermoregulatory mechanisms of a healthy human body serve to maintain the body at a constant temperature of about 37° C. (98.6° F.), a condition sometimes referred to as normothermia. To maintain normothermia, the thermoregulatory mechanisms act so that heat lost from the person's body is replaced by the same amount of heat generated by metabolic activity within the body. For various reasons such as extreme environmental exposure to a cold environment or loss of thermoregulatory ability as a result of disease or anesthesia, a person may develop a body temperature that is below normal, a condition known as hypothermia. A person may develop a condition that is above normothermia, a condition known as hyperthermia, as a result of extreme exposure to a hot environment, or malfunctioning thermoregulatory mechanisms, the latter being a condition sometimes called malignant hyperthermia. The body may also establish a set point temperature (that is, the temperature which the body's thermoregulatory mechanisms function to maintain) that is above normothermia, a condition usually referred to as fever. The present invention addresses all of these situations.

Accidental hypothermia is generally a dangerous condition that may even be life threatening, and requires treatment. If severe, for example where the body temperature drops below 30° C., hypothermia may have serious consequences such as cardiac arrhythmias, inability of the blood to clot normally, or interference with normal metabolism. If the period of hypothermia is extensive, the patient may even experience impaired immune response and increased incidence of infection.

Simple methods for treating accidental hypothermia have been known since very early times. Such methods include wrapping the patient in blankets, administering warm fluids by mouth, and immersing the patient in a warm water bath. If the hypothermia is not too severe, these methods may be effective. However, wrapping a patient in a blanket depends on the ability of the patient's own body to generate heat to re-warm the body. Administering warm fluids by mouth relies on the patient's ability to swallow, and is limited in the temperature of the liquid consumed and the amount of fluid that may be administered in a limited period of time. Immersing a patient in warm water is often impractical, particularly if the patient is simultaneously undergoing surgery or some other medical procedure.

More recently, hypothermia may be treated in a more complex fashion. Heated warming blankets may be applied to a patient or warming lamps that apply heat to the skin of the patient may be used. Heat applied to the patient's skin, however, has to transmit through the skin by conduction or radiation which may be slow and inefficient, and the blood flow to the skin may be shut down by the body's thermoregulatory response, and thus, even if the skin is warmed, such mechanisms may be ineffective in providing heat to the core of the patient's body. When breathing gases are administered to a patient, for example a patient under anesthesia, the breathing gases may be warmed. This provides heat relatively fast to the patient, but the amount of heat that can be administered without injuring the patient's lungs is very limited. An alternative method of warming a hypothermic patient involves infusing a hot liquid into the patient via an IV infusion, but this is limited by the amount of liquid that can be infused and the temperature of the liquid.

In extreme situations, a very invasive method may be employed to control hypothermia. Shunts may be placed into the patient to direct blood from the patient through an external machine such as a cardiopulmonary by-pass (CPB) machine which includes a heater. In this way, the blood may be removed from the patient, heated externally, and pumped back into the patient. Such extreme measures have obvious advantages as to effectiveness, but also obvious drawbacks as to invasiveness. The pumping of blood through an external circuit that treats the blood is generally quite damaging to the blood, and the procedure is only possible in a hospital setting with highly trained personnel operating the equipment.

Accidental hyperthermia may also result from various conditions. Where the normal thermoregulatory ability of the body is lost, because of disease or anesthesia, run-away hyperthermia, also known as malignant hyperthermia, may result. The body may also set a higher than normal set point resulting in fever which is a type of hyperthermia. Like hypothermia, accidental hyperthermia is a serious condition that may sometimes be fatal. In particular, hyperthermia has been found to be neurodestructive, both in itself or in conjunction with other health problems such as traumatic brain injury or stroke, where a body temperature in excess of normal has been shown to result in dramatically worse outcomes, even death.

As with hypothermia, when the condition is not too severe, simple methods for treating the condition exist, such as cold water baths and cooling blankets, or antipyretic drugs such as aspirin or acetominophen, and for the more extreme cases, more effective but complex and invasive means such as cooled breathing gases, cold infusions, and blood cooled during CPB also exist. These, however, are subject to the limitations and complications as described above in connection with hypothermia.

Although both hypothermia and hyperthermia may be harmful and require treatment in some case, in other cases hyperthermia, and especially hypothermia, may be therapeutic or otherwise advantageous, and therefore may be intentionally induced. For example, periods of cardiac arrest or cardiac insufficiency in heart surgery result in insufficient blood to the brain and spinal cord, and thus can produce brain damage or other nerve damage. Hypothermia is recognized in the medical community as an accepted neuroprotectant and therefore a patient is often kept in a state of induced hypothermia. Hypothermia also has similar advantageous protective ability for treating or minimizing the adverse effects of certain neurological diseases or disorders such as head trauma, spinal trauma and hemorrhagic or ischemic stroke. Therefore it is sometimes desirable to induce whole-body or regional hypothermia for the purpose of facilitating or minimizing adverse effects of certain surgical or interventional procedures such as open heart surgery, aneurysm repair surgeries, endovascular aneurysm repair procedures, spinal surgeries, or other surgeries where blood flow to the brain, spinal cord or vital organs may be interrupted or compromised. Hypothermia has even been found to be advantageous to protect cardiac muscle tissue after a myocardial infarct (MI).

Current methods of attempting to induce hypothermia generally involve constant surface cooling, by cooling blanket or by alcohol or ice water rubs. However, such cooling methods are extremely cumbersome, and generally ineffective to cool the body's core. The body's response to cold alcohol or ice water applied to the surface is to shut down the circulation of blood through the capillary beds, and to the surface of the body generally, and thus to prevent the cold surface from cooling the core. If the surface cooling works at all, it does so very slowly. There is also an inability to precisely control the temperature of the patient by this method.

If the patient is in a surgical setting, the patient may be anesthetized and cooled by CPB as described above. Generally, however, this is only available in the most extreme situations involving a full surgical team and full surgical suite, and importantly, is only available for a short period of time because of the damage to the blood caused by pumping. Generally surgeons do not wish to pump the blood for periods longer than 4 hours, and in the case of stroke or traumatic brain damage, it may be desirable to induce hypothermia for longer than a full day. Because of the direct control of the temperature of a large amount of blood, this method allows fairly precise control of the patient's temperature. However, it is this very external manipulation of large amounts of the patient's blood that makes long term use of this procedure very undesirable.

Means for effectively adding heat to the core of the body that do not involve pumping the blood with an external, mechanical pump have been suggested. For example, a method of treating hypothermia or hyporthermia by means of a heat exchange catheter placed in the bloodstream of a patient was described in U.S. Pat. No. 5,486,208 to Ginsburg, the complete disclosure of which is incorporated herein by reference. Means of controlling the temperature of a patient by controlling such a system is disclosed in U.S. Pat. No. 5,837,003, also to Ginsburg, the complete disclosure of which is incorporated herein by reference. A further system for such controlled intervascular temperature control is disclosed in publication WO 00/10494 to Ginsburg et al., the complete disclosure of which is incorporated herein by reference. Those patents and publication disclose a method of treating or inducing hypothermia by inserting a heat exchange catheter having a heat exchange area including a balloon with heat exchange fins into the bloodstream of a patient, and circulating heat exchange fluid through the balloon while the balloon is in contact with the blood to add or remove heat from the bloodstream. (As used herein, a balloon is a structure that is readily inflated under pressure and collapsed under vacuum.)

A number of catheter systems for cooling tissue adjacent the catheter or regulating the temperature of the catheter using the temperature of fluid circulating within the catheter are shown in the published art. Some such catheters rely on a reservoir or similar tank for a supply of heat exchange fluid. For example, U.S. Pat. No. 3,425,419 to Dato, U.S. Pat. No. 5,423,811 to Imran et al., U.S. Pat. No. 5,733,319 to Neilson, et al., U.S. Pat. No. 6,019,783 to Phillips, et al., and U.S. Pat. No. 5,624,392 to Saab disclose catheters with circulating heat exchange fluid from a tank or reservoir. For such systems that involve a catheter placed in the bloodstream, however, difficulties arise in sterilizing the fluid source between uses and rapidly changing the temperature of a large volume of fluid having a significant thermal mass.

For the foregoing reasons, there is a need for a rapid and effective means to add or remove heat from the fluid supply for a catheter used to control the body temperature of a patient in an effective and efficient manner, while avoiding the inadequacies of the prior art methods. In particular, a fluid source that rapidly, efficiently and controllably regulates a disposable source of fluid based on feedback from the temperature of the patient or target tissue within the patient would be a great advantage.

SUMMARY OF THE INVENTION

The present invention avoids many of the problems of the prior art by providing an improved system to control the heating and/or cooling of a catheter with a body. The system generally includes a control unit exterior to body, a number of conduits extending from the control unit, and a heat transfer catheter in communication with the control unit via the conduits. The control unit modulates the temperature of a heat transfer region on the catheter using an advantageous control methodology to avoid over-shooting a target temperature. The catheter and conduits preferably define a fluid circulation path, wherein the control unit modulates the temperature of the heat transfer region by adjusting the temperature of a heat transfer fluid within the circulation path. Desirably, the control unit defines a cavity and the conduits are connected to a cassette that fits within the cavity, the cassette having an external heat exchanger through which the heat exchange fluid flows.

In one aspect of the present invention, a controller for controlling the temperature and flow of heat exchange fluid within a circuit is provided. The circuit is of a type that includes a heat exchange catheter, an external heat exchanger, and a pump for flowing heat exchange fluid through the circuit. The controller includes a heat and/or cold generating element in thermal contact with the external heat exchanger containing the heat exchange fluid. A patient sensor is positioned and configured to generate a signal representing a biophysical condition of the patient. The microprocessor in the controller receives the signal from the patient sensor and responds by controlling the generating element. The control unit further includes a mechanical drive unit for activating the pump contained in the circuit, and a safety sensor for detecting a fluid parameter in the circuit to generate a safety signal representative of the presence or absence of the fluid parameter. The safety signal is transmitted to the microprocessor that responds by controlling the operation of the pump. The sensor may be a bubble detector, and the fluid parameter is gas entrained in the heat exchange fluid. Alternatively, the circuit further comprises a reservoir, and the sensor is a fluid level detector for detecting a low fluid level in the reservoir.

In a still further aspect of the present invention, a heat transfer catheter flow system comprises a heat transfer medium circulation loop including a transfer catheter; a heat transfer unit, and conduits coupled to the heat transfer catheter and heat transfer unit that enable circulation of the heat transfer medium therebetween. The system further includes a pump head in contact with heat transfer medium within the circulation loop for circulating the medium through the loop. A cassette including a heat transfer unit and the pump head mates with a controller housing a control circuit and a pump motor so that the pump head engages the pump motor. An electronic feedback loop that detects back-torque experienced by the pump motor provides feedback to a control circuit that in turn controls the speed of the pump motor.

In another aspect, the present invention provides a controller for controlling the temperature and flow of heat exchange fluid within a circuit of the type that has a heat exchange catheter, an external heat exchanger, and a pump for flowing heat exchange fluid through the circuit. The controller includes a heat and/or cold generating element in thermal contact with the external heat exchanger. A mechanical drive unit activates the pump contained in the circuit to pump the heat exchange fluid. The controller includes a microprocessor connected to control both the generating element and the mechanical drive unit. A safety system is provided for detecting problems in the circuit. The safety system includes a plurality of sensors that generate signals indicative of respective parameters of the system and/or patient. The signals are transmitted to the microprocessor that responds by controlling the operation of the generating element and the mechanical drive unit. In one embodiment, the safety system includes a sensor for detecting the fluid level within the circuit. In a further embodiment, the safety system includes a sensor for detecting the temperature of a location within the patient, and further may include a redundant sensor for detecting the temperature of a location within the patient wherein a microprocessor is responsive to a difference in the two sensed patient temperatures. Furthermore, the safety system may include sensors for detecting bubbles within the circuit, detecting the operating status of the generating element, or detecting the operating status of the mechanical drive unit.

In one embodiment of the invention, a heat transfer catheter system includes a heat transfer catheter, a heat transfer unit, and conduits coupling the two elements and enabling circulation of heat transfer medium therebetween. The heat transfer unit defines a flow channel between opposite sidewalls, one of the sidewalls being relatively thin and flexible and providing minimal thermal insulation, while the opposite sidewall is relatively non-flexible so as to provide structural support to the heat transfer unit. The system may include a controller having a cavity for receiving the heat transfer unit and a heat and/or cold generating element therein positioned adjacent the flexible sidewall when the heat transfer unit is inserted within the cavity. The cavity may be sized such that outward expansion of the flexible sidewall upon flow of heat exchange medium through the flow channel causes the heat transfer unit to become compressively retained within the cavity. Desirably, the flexible sidewall attaches to the opposite sidewall both around their respective edges and along a series of lines within the edges such that the flow channel defines a serpentine path.

The present invention also provides a method of regulating the temperature of patient; comprising the steps of:
  providing a heat exchange catheter system including a heat exchange catheter having a fluid path therethrough, a pair of conduits fluidly connected to the heat exchange catheter, and an external heat exchanger connected via the conduits to circulate heat exchange medium through the exchange catheter;
  providing a first controller adapted to couple to the external heat exchanger of the heat exchange catheter system, the first controller including a heat and/or cold generating element therein for exchanging heat at a first rate with the heat exchange medium within the external heat exchanger;
  providing a second controller adapted to couple to the external heat exchanger of the heat exchange catheter system, the second controller including a heat and/or cold generating element therein for exchanging heat at a second rate with the heat exchange medium within the external heat exchanger;
  coupling the heat exchange catheter system with the first controller;
  inserting the heat exchange catheter into the patient;
  regulating the temperature of the patient by exchanging heat at the first rate between the generating element of the first controller and the external heat exchanger;
  de-coupling the heat exchange catheter system from the first controller;
  coupling the heat exchange catheter system with the second controller; and
  regulating the temperature of the patient by exchanging heat at the second rate between the generating element of the second controller and the external heat exchanger.

The method may include performing a therapeutic or diagnostic procedure on the patient between the steps of de-coupling the heat exchange catheter system from the first controller and the step of coupling the heat exchange catheter system with the second controller. Indeed, the first controller and the second controller may be the same physical device.

In a still further method of the present invention; the rate of change of a patient's body temperature is controlled using a heat transfer catheter and associated controller The transfer catheter has a heat transfer region thereon, and the controller is placed in communication with the catheter via conduits. The controller is adapted to elevate or depress the temperature of the catheter heat transfer region relative to the body temperature. The patient's body temperature within a body cavity or in another location is sensed, while the temperature of the heat transfer region is determined. A target temperature is then selected. The target temperature may be different than the body temperature, or may be the same if maintenance of normal patient temperature is the goal. A ramp rate equal to the time rate of change of temperature from the body temperature to the target temperature is selected. The temperature of the transfer region of the catheter based on the ramp rate is set. The method includes monitoring the temperature differential between the target temperature and the body temperature; and reducing the ramp rate when the temperature differential reduces below a predetermined threshold. Desirably, the heat transfer catheter and conduits defined a fluid circulation path therethrough, wherein the step of setting the temperature of the catheter heat transfer region comprises setting the temperature of a circulating fluid within the circulation path. Preferably, the step of determining the temperature of the catheter heat transfer region comprises directly or indirectly sensing the temperature of the circulating fluid. A comparison may be made between the target temperature and the temperature of the circulating fluid, which is then used to adjust the temperature of the circulating fluid.

In one aspect of the invention, the reservoir section is provided with a means to detect the fluid level in the reservoir and comprises at least one prism mounted within the reservoir section adjacent the inside of a relatively transparent window or wall portion in the reservoir, and at least one optical beam source and at least one optical beam sensor mounted on the reusable control unit adjacent the outside of the window. In one specific embodiment, the fluid level detector comprises a prism mounted in the reservoir, a light beam source and a light beam sensor. The prism has a diffraction surface and the light beam source directs a light beam against that surface. The prism is configured so that when the diffraction surface is in contact with air, the light beam is reflected to impinge on the light beam sensor and the sensor generates a signal. Likewise, when the diffraction surface is in contact with fluid, the light beam does not reflect to the sensor and the sensor does not generate a signal.

In operation, a light beam is directed through the reservoir section and against the prism at a particular point along its angled length. The sensor is located to detect the presence or absence of a reflected beam. As long as the fluid reservoir remains full and the fluid level is at a pre-determined elevation above the point of impingement of the light, beam, the diffraction surface of the prism at that point is in contact with the fluid. Therefore, the light beam directed at the prism travels through the prism and, upon reaching the diffraction surface is reflected such that the sensor does not observe a reflected beam. If the fluid falls below the pre-determined elevation; the diffraction surface of the prism at the point where the beam impinges on it will no longer be in contact with the fluid and will be in contact with air instead. Air has a different index of refraction than the index of refraction of the fluid. Accordingly, upon reaching the diffraction surface, the reflected beam will no longer reflect out to the same point, and is reflected in such a manner that it impinges upon the sensor; which will then observe a reflected beam.

BRIEF DESCRIPTION OF THE DRAWINGS

FIGS. 3A-3B together show a flowchart of a control scheme of the heat exchange system of the present invention;

FIG. 4 is a graph of the sensed temperature of a target tissue or body fluid over time under the influence of the control scheme of FIGS. 3A-3B;

FIG. 10A is an exploded view of a first disposable heat exchange cassette for use in the present invention;

FIGS. 13C-13D are plan and sectional views, respectively, of the bulkhead assembly of FIG. 13B;

FIG. 14B is a simplified plan view of the feedblock section of FIG. 14A illustrating in hidden lines a fluid pressure regulating mechanism therein;

FIG. 14C is a slightly magnified view of a portion of the pressure regulating mechanism of FIG. 14B;

FIG. 14F is a cross-section taken along the line 14F-14F in FIG. 14C;

FIG. 14G is a cross-section taken along the line 14G-14G in FIG. 14C;

DETAILED DESCRIPTION OF EXEMPLARY EMBODIMENTS

The present invention is primarily intended to include a catheter placed in the bloodstream of a patient for regulating the patient's body temperature, although those skill in the art will understand that various other applications for the system of the present invention are possible Indeed; the present invention may have applications beyond controlling the temperature of an internal body fluid and the claims should not be so limited. In a preferred application; one or more of the heat exchange catheters of the present invention are positioned within a patient's vasculature to exchange heat with the blood in order to regulate the overall body temperature; or to regulate the temperature of a localized region of the patient's body. Heat exchange fluid is then circulated through the catheter to exchange heat between the blood and the heat exchange fluid; and a controller manages the functioning of the system. The catheters may be for example suitable for exchanging heat with arterial blood flowing toward the brain to cool the brain, and may thus prevent damage to brain tissue that might otherwise result from a stroke or other injury; or cooling venous blood flowing toward the heart to cool the myocardium to prevent tissue injury that might otherwise occur following an MI or other similar event.

In general the invention provides a preferred control unit and method for controlling the temperature and flow of heat transfer fluid for a heat transfer catheter used for controlling the body temperature of a patient. The control unit initially automatically supplies heat transfer fluid to the heat transfer catheter to prime the heat exchange catheter for use. It also receives input from the user receives temperature information from sensors that sense patient temperature information; and based thereon, automatically controls the temperature of the heat transfer fluid. Further; based on feedback from a pump in a cassette containing the heat transfer fluid; the control unit supplies heat transfer fluid at a relatively constant pressure. The cassette and the controller, working together, have several warning or alarm states that warn the user of dangerous situations, for example, by shutting down the pump motor and notifying the user if the fluid level in the cassette is unacceptably low.

Overview of Heat Exchange System

Any suitable heat exchange catheter may be utilized in a heat exchange system for regulating the temperature of a patient or a region of the patient's body and controlled by the control unit as disclosed herein. In addition to the catheters disclosed herein, and by way of illustration and not of limitation; catheters that may be utilized in this invention are the catheters disclosed in U.S. Pat. No. 5,486,208 to Ginsburg, U.S. Pat. No. 5,837,003 to Ginsburg, WO 00/10494 to Ginsburg et al., and U.S. Pat. No. 5,624,392 to Saab, the complete disclosure of each of which is hereby incorporated in full herein by reference.

Figure 1:
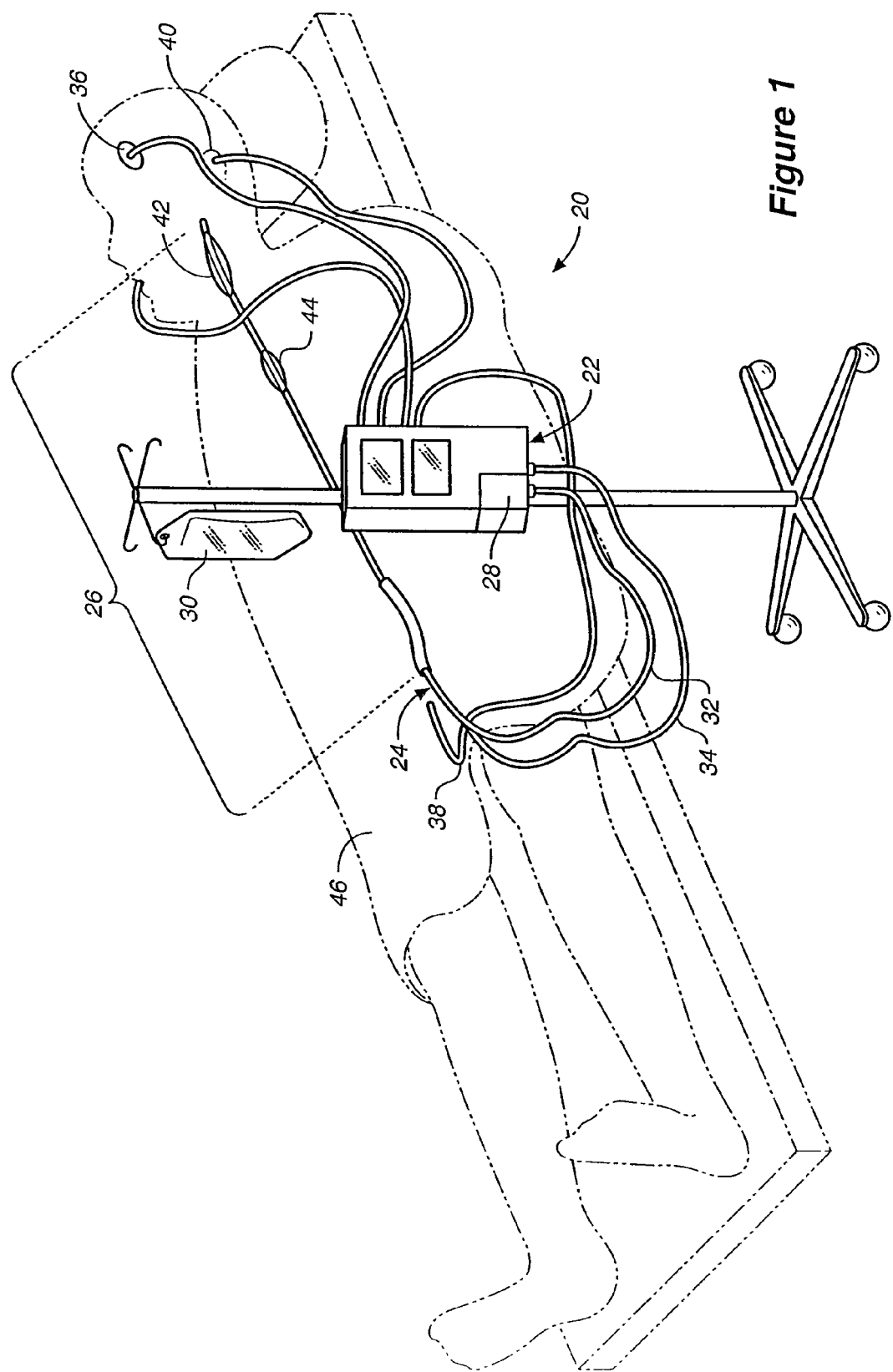
FIG. 1 is a perspective view of a patient undergoing treatment using a system in accordance with the present invention.

One example of such a heat exchange catheter system 20 is shown in FIG. 1, and includes a control unit 22 and a heat exchange catheter 24 formed with at least one heat transfer section 44. The heat transfer section or sections are located on that portion of the catheter 24, as illustrated by section 26 that is inserted into the patient. This insertion portion is less than the full-length of the catheter and extends from the location on the catheter just inside the patient; when the catheter is fully inserted; to the distal end of the catheter. The control unit 22 may include a fluid pump 28 for circulating a heat exchange fluid or medium within the catheter 24 and a heat exchanger component for heating and/or cooling circulating fluids within the heat transfer system 20. A reservoir or fluid bag 30 may be connected to the control unit 22 to provide a source of heat transfer fluid such as, saline, blood substitute solution or other biocompatible fluid A circulatory heat exchange flow channel within the catheter may be respectively connected to inlet 32 and outlet 34 conduits of the pump 28 for circulation of the heat transfer fluid through the balloon to cool the flow of body fluid such as blood within a selected body region. A similar arrangement may be implemented for heating of selected body regions simultaneously or independent of each other using the cooling component of the system.

The control unit 22 may further receive data from a variety of sensors which may be, for example solid-state thermocouples to provide feedback from the catheter and various sensors to provide patient temperature information representing core temperature or temperature of selected organs or portions of the body For instance, sensors may include a temperature probe 36 for the brain or head region, a rectal temperature probe 38, an ear temperature probe 40, an esophageal temperature probe (not shown); a bladder temperature probe (not shown) and the like.

Based upon sensed temperatures and conditions, the control unit 22 may direct the heating or cooling of the catheter in response The control unit 22 may activate a heat, exchanger at a first sensed temperature to heat fluid which is then circulated through the balloon, and may also de-activate the heat exchanger at a second sensed temperature which may be relatively higher or lower than the first sensed temperature or any other predetermined temperature. Alternatively, the control unit may actively cool the heat exchange fluid to cool the balloon. The control unit 22 may operate multiple heat transfer units to independently heat or cool different selected heat transfer sections to attain desired or preselected temperatures in body regions. Likewise the controller 22 may activate more than one heat exchanger to control temperature at particular regions of the patient's body. The controller might also activate or de-activate other apparatus, for example external heating blankets or the like in response to sensed temperatures.

The regulation exercised over the heat transfer catheters or other devices may be a simple on-off control, or may be a significantly more sophisticated control scheme including regulating the degree of heating or cooling, ramp rates of heating or cooling, proportional control as the temperature of the heat exchange region or patient approaches a target temperature; or the like.

The control unit 22 may further include a thermoelectric cooler and heater (and associated flow conduits) that are selectively activated to perform both heating and cooling functions with the same or different heat transfer mediums within the closed loop catheter system. For example; a first heat transfer section 42 located on the insertion portion 26 of at least one temperature regulating catheter 24 may circulate a cold solution in the immediate head region; or alternatively, within a carotid artery or other blood vessel leading to the brain. The head temperature may be locally monitored with temperature sensors 36 positioned in a relatively proximate exterior surface of the patient or within selected body regions. Another heat transfer section 44 of the catheter 24 also located on the insertion portion 26 may circulate a heated solution within a collapsible balloon or otherwise provide heat to other body locations through heat elements or other mechanisms described in accordance with other aspects of the invention. While heat exchange catheter 24 may provide regional hypothermia to the brain region for neuroprotective benefits other parts of the body may be kept relatively warm so that adverse side effects such as discomfort, shivering, blood coagulopathies, immune deficiencies, and the like, may be avoided or minimized. Warming of the body generally below the neck may be further achieved by insulating or wrapping the lower body in a heating pad or blanket 46 while the head region above the neck is cool. It should be understood of course that multiple heat exchange sections of the catheter 24 may be modified to provide whole body cooling or warming to affect body core temperature.

Exemplary Heat Exchange System

The present invention contemplates the use of a re-usable controller or control console having a heater/cooler device therein and which receives a disposable heat exchange element coupled via conduits to a distal in dwelling heat exchange catheter. More specifically, the controller desirably includes an outer housing having an opening or slot for receiving the heat exchange element, the opening and housing ensuring reliable positioning of the heat exchange element in proximity with the heater/cooler device. In this manner, set up of the system is facilitated because the operator only needs to fully insert and seat the heat exchange element into the controller opening in order to couple the reusable and disposable portions of the system.

Figure 2:
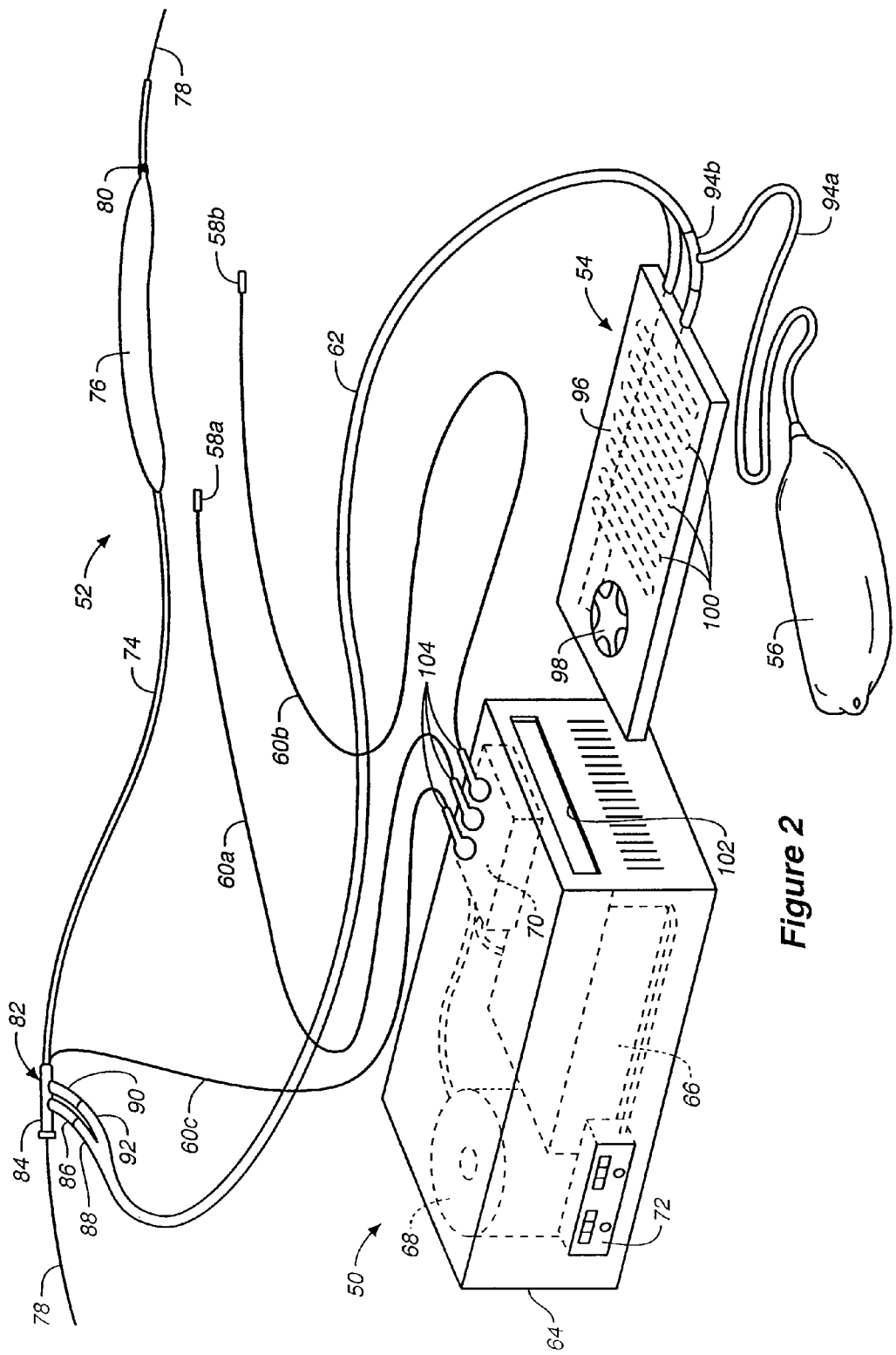
FIG. 2 is a schematic illustration of a disposable heat exchange cassette attached to a heat exchange catheter and an external fluid source; and positioned for insertion into a suitable opening in a re-usable control unit of the present invention.

In an exemplary embodiment, FIG. 2 illustrates a heat exchange catheter system that includes a re-usable control unit 50 and a plurality of disposable components including a heat exchange catheter 52, a heat exchange element 54, a saline bag 56, sensors 58a, 58b and associated wires 60a, 60b, and a plurality of fluid flow conduits including a two-way conduit 62 extending distally from the heat exchange element 54. The re-usable control unit 50 includes an outer housing 64 within which is provided a heater/cooler 66 a pump driver 68, and a controller processor 70. In addition, a manual input unit 72 enables an operator to enter desirable operating parameters of the controller, for example a pre-selected temperature for the brain. Each of the electronic devices provided within the control unit 50 communicate through suitable wiring.

The heat exchange catheter 52 is formed with a catheter conduit 74 and a heat exchanger 76 which may be, for example, a heat exchange balloon operated using a closed-loop flow of a biocompatible fluid that serves as the heat exchange medium. The catheter 52 may include a working lumen (not shown) for injection of drugs, fluoroscopic dye, or the like, and for receipt of a guidewire 78 for use in placing the catheter at an appropriate location in the patient's body. A sensor 80 may be provided on the catheter 52 distal to the heat exchanger 76 to monitor the temperature of the heat exchange balloon and other sensors (not shown) may be provided as desired to monitor the blood temperature at the distal tip of the catheter; at the proximal tip of the balloon, or at any other desired location along the catheter.

As seen in FIG. 2, the proximal end of the catheter conduit 74 may be connected to a multi-arm adapter 82 for providing separate access to various channels in the catheter 52. For example, a first arm 84 may provide access to the working lumen of the catheter 52 for insertion of the guidewire 78 to steer the heat exchange catheter to the desired location. Where the heat exchanger 76 is a heat exchange balloon for closed-loop flow or a heat exchange medium the adapter 82 may contain a second arm 86 connected to an inflow line 88, and a third arm 90 connected to an outflow line 92. The inflow line 88 and outflow line 92 are therefore placed in flow communication with respective inflow and outflow channels (not shown) provided in the conduit 74 and heat exchanger 76. In this regard, the inflow and outflow lines 88, 92 may come together to form the dual channel conduit 62 connected to the heat exchange element 54. Furthermore, an external fluid source such as the saline bag 56 may be placed in fluid communication with the outflow line 92 via a conduit 94a and a T-junction 94b. As will be explained further below, the external fluid source is used to prime the closed loop heat exchange balloon system. Alternatively, the external fluid source maybe directly connected to the heat exchange unit 54.

Still with reference to FIG. 2, the heat exchange unit 54 desirably includes a heat exchange plate 96 and a pump head 98. The pump head 98 pumps heat exchange fluid through a serpentine fluid pathway 100 in the heat exchange plate 96, and through the associated conduits and catheter 52. As mentioned, the heat exchange unit 54 is configured to install into the re-usable control unit 50. In this regard, the heat exchange unit 54 is desirably plate-shaped and sized to fit through art elongate slot 102 in the control unit housing 64. Once inserted, the pump head 98 is placed in proximity to and engaged with the pump driver 68, and the heat exchange plate 96 is placed in proximity to and in thermal communication with the heater/cooler 66. A solid-state thermoelectric heater/cooler 66 is particularly advantageous because the same unit is capable of either generating heat or removing heat by simply changing the polarity of the current activating the unit. Therefore, the heater/cooler 66 may be conveniently controlled so as to supply or remove heat from the system without the need for two separate units.

The pump driver 68 engages and activates the pump head 98 to cause it to circulate heat exchange fluid through the heat exchange unit 54 and the serpentine path 100 in the heat exchange plate 96. Therefore, when the heat exchanger unit 54 is properly installed in the control unit 50, the heater/cooler 66 may act to heat or cool the heat exchange fluid as that fluid is circulated through the serpentine pathway 100 and thereafter through the conduits leading to the in-dwelling heat exchanger 76. When the heat exchange fluid is circulated through the heat exchanger 76 located in the patient's body, it may act to add or remove heat from the body. In this way the heater/cooler 66 regulates the blood temperature of the patient as desired.

The heater/cooler 66 and a pump driver 68 are responsive to the controller processor 70. The processor 70 receives data input through electrical connections 104 to numerous sensors, for example body temperature sensors 58a, 58b positioned to sense the temperature at various locations within the patient. For example the temperature may be sensed at the patient's ear, brain region; bladder, rectum, esophagus, or other appropriate location as desired by the operator. Also, as mentioned, a sensor 80 may monitor the temperature of the heat exchanger 76, and other sensors along the catheter 52 may provide input to the controller processor 70, such as via a wire 60c. Additionally, by means of the manual input unit 72, an operator provides the operating parameters of the control system such as, for example; a pre-selected temperature for the brain and/or the whole body of the patient. The operator input parameters are communicated to the controller processor 70 by means of appropriate wiring.

The controller processor 70 coordinates the various data received and selectively actuates the several operational subsystems to achieve and maintain desired results, i.e., proper regulation of the patient's body temperature. For example, the processor 70 may actuate the heater/cooler 66 to increase the amount heat it is removing if the actual temperature is above the specified temperature, or it may decrease the amount of heat being removed if the temperature is below the specified temperature. Alternatively, the processor 70 may stop the pumping of the heat exchange fluid when the sensed body or regional temperature reaches the desired temperature.

Referring still to FIG. 2, the disposable heat exchange unit 54 of the invention is shown as being attached to a heat exchange catheter 52, external fluid source 56 is positioned in cooperation with a suitable reusable control unit. Prior to commencing, treatment the heat exchange unit 54 is inserted into the revisable control unit 50, the external fluid source 56 is attached to the fill port and the pump 98 is automatically or passively primed and the disposable system filled, after which the catheter is ready for insertion in the vasculature of the patient; for example in the inferior vena cava or the carotid artery. Chilled or warmed biocompatible fluid such as saline, is pumped into the carotid artery. Chilled or warmed biocompatible fluid such as saline, is pumped into the closed circuit catheter, which exchanges heat directly with the patient's blood. The control unit serves to automatically control the patient's temperature. Once treatment with the catheter is complete, the catheter is removed from the patient and the cassette is removed from the reusable control unit. Both the catheter and cassette are then discarded. The reusable control unit, however, which never comes into direct contact with the heat exchange fluid, is ready for immediate use for treatment on other patients, along with a new cassette and catheter and fresh external fluid source.

Exemplary Method of Temperature Control

Figure 3A:
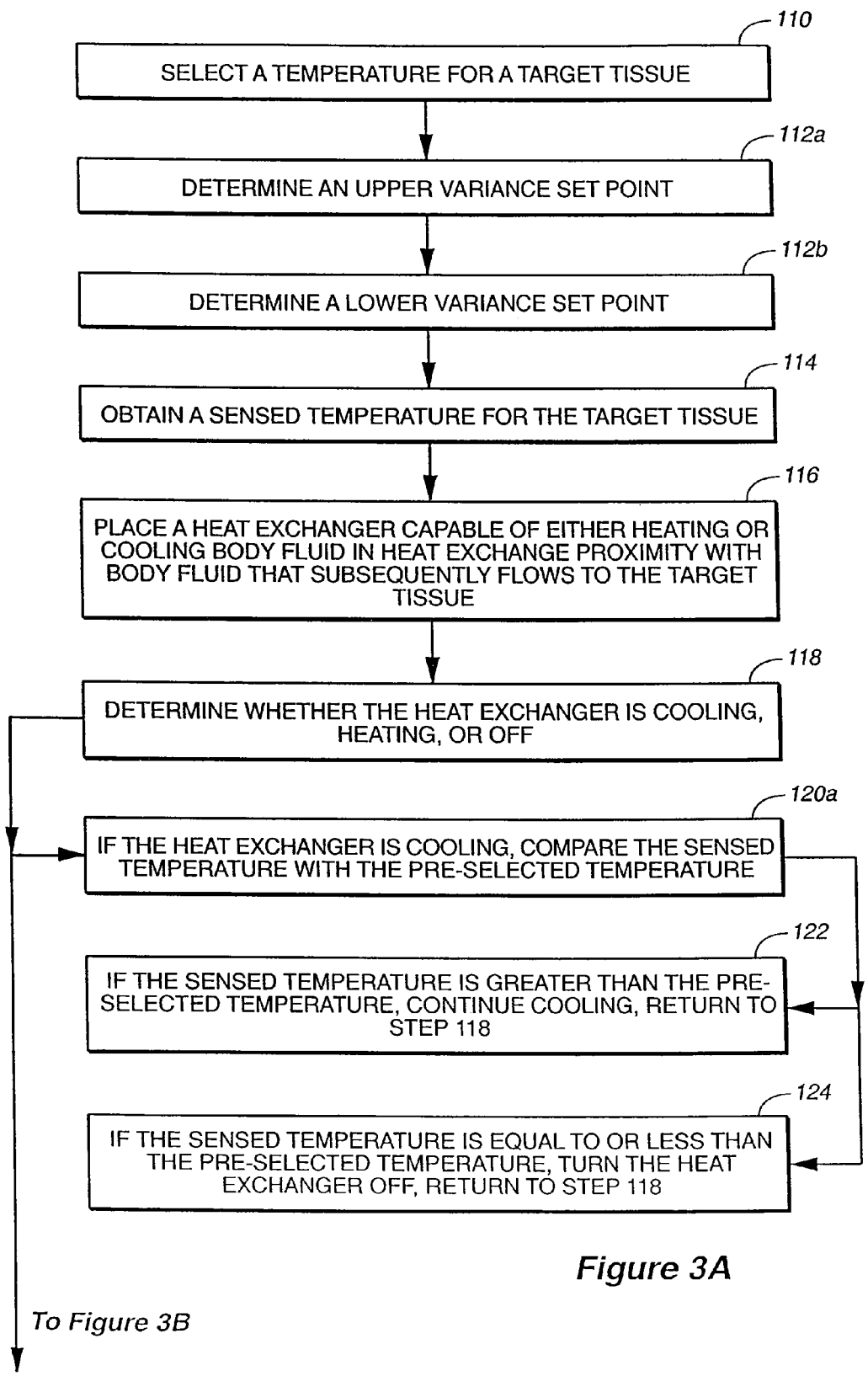

The flowchart seen in FIGS. 3A and 3B illustrates an exemplary sequence of steps that the controller processor 70 coordinates during temperature regulation of a patient. First, in step 110, a target temperature for the target tissue (which may be the entire body) is selected, generally by user input. The target temperature may be different than the body temperature, or may be the same if maintenance of normal patient temperature is the goal. Steps 112a and 112b involve determination of an upper variance set point and a lower variance set point, respectively. This is generally a pre-set buffer range above and below the target temperature that is built or programmed into the controller processor. These variance set points straddle the target temperature and create a buffer range of temperature within which the controller operates.

More specifically, the sensed temperature for the target tissue is obtained in step 114 prior to or after step 116 in which a heat exchanger capable of either heating or cooling body fluid is placed in proximity with body fluid that subsequently flows to the target tissue. Based on user input or on a comparison between the target temperature and the sensed tissue temperature a determination is made in step 118 as to whether the heat exchanger will be operating a cooling mode, a heat mode, or will remain off. That is, if the target temperature equals the tissue temperature then there will be no need to initially heat or cool the body fluid.

The determination step 118 leads to three different modes of operation of the system depending on whether the system will be COOLING, HEATING, or OFF. These modes of operation correspond to steps 120a, 120b, and 120c, which appear on both the FIGS. 3A and 3B.

If the system is in the COOLING mode, the flowchart logic leads to step 120a which compares the sensed tissue temperature with the pre-selected target temperature. If the tissue temperature is greater than the target temperature the system continues cooling as indicated in step 122, and the processor 70 returns to decision step 118. On the other hand, if the sensed tissue temperature is equal to or less than the target temperature, the heat exchanger is converted to the OFF mode as indicated in step 124 and the process 70 returns to decision step 118.

If the system is in the HEATING mode, the flowchart logic leads to step 120b which also compares the sensed tissue temperature with the pre-selected target temperature. If the tissue temperature is less than the target temperature, the system continues heating as indicated in step 126, and the processor 70 returns to decision step 118. On the other hand, if the tissue temperature is equal to or greater than the target temperature, the heat exchanger is converted to the OFF mode as indicated in step 128, and the processor 70 returns to decision step 118.

If the system is in the OFF mode the flowchart logic leads to step 120c which compares the sensed tissue temperature with the upper variance temperature set point. Then, if the sensed tissue temperature is equal to or greater than the upper variance set point, the system is converted to the COOLING mode as indicated in step 130, and the processor 70 returns to decision step 118. If the tissue temperature is less than the upper variance set point, the processor continues to step 132 in the flowchart logic, and determines if the tissue temperature is equal to or less than the lower variance set point, whereby the system is converted to the HEATING mode and processor 70 returns to decision step 118. Finally, if the tissue temperature is between the upper and lower variance set points, the system does nothing as indicated in step 134, and the processor 70 returns to decision step 118.

FIG. 4 is a graphical illustration plotting the fluctuating sensed tissue temperature over a period of time relative to the target temperature and variance set points. In the example, the target temperature is set at 31 degrees Celsius, with the upper and lower variance set points ½ degrees on either side. Initially, the sensed tissue temperature is greater than the target temperature, such as if the heat exchange catheter is placed in contact with blood at 37 degrees Celsius. The system is first placed in the COOLING mode so that the sensed tissue temperature is reduced until it equals the target temperature at 136, corresponding to steps 120a and 124 in FIG. 3A. In step 124, the heat exchanger is converted to the OFF mode, which results in the sensed tissue temperature climbing until it reaches the upper variance set point at 138, corresponding to step 130 in FIG. 313, at which time the system begins cooling again. This cycle is repeated in the region indicated at A.

Eventually, the patient may be unable to maintain even the target temperature as shown by the temperature profile in the region indicated at B. For example, after the sensed tissue temperature reaches the target temperature at 140, and the heat exchanger is turned OFF, the sensed target temperature may continue to drift lower until it reaches the lower variance set point at 142. The controller logic senses this in step 132 of FIG. 3B, and converts the system to the HEATING mode. Subsequently, the sensed tissue temperature climbs to the target temperature at 144, and the system is again turned OFF, corresponding to steps 120b and 128 in FIG. 3B. Alternatively, depending on the patient and the situation, it may be that after the sensed tissue temperature reaches the target temperature and the heat exchanger is turned OFF, the patient's temperature may begin to increase until it rises to the upper variance set point temperature, at which point, as described in box 130 the heat exchanger begins to COOL. As can be appreciated, the sensed tissue temperature continues to fluctuate between the upper and lower variance set points in this manner.

The control scheme as applied to the system of the present invention has the advantage of allowing the operator to essentially input a desired temperature after which time the system will automatically regulate the tissue temperature until it reaches the target temperature, and will maintain the tissue temperature at that target temperature. The buffer range created by the upper and lower variance set points prevents the controller from turning the heater/cooler on and off or activating and de-activating the pump driver in rapid succession, actions that would be potentially damaging to these electric devices.

Exemplary Heat Exchange Control Unit

FIGS. 5A-5F are various views of an exemplary heat exchange control unit 150 of the present invention that is particularly suited for rapid temperature regulation of a patient. As seen in the Figures, the control unit 150 comprises a vertically-oriented outer housing having a lower portion 152 and upper portion 154 separated at a generally horizontal dividing line 156 located close to the top of the unit. The control unit 150 is mounted on wheels 158 for ease of portability, with the wheels preferably being of the swivel type having foot-actuated locks. For ease of servicing, the upper and lower portions may be joined together with hinges 155 at the back so that the top portion may be lifted up and rotated back to expose the interior of the unit. In an exemplary embodiment, the control unit 150 has a height that enables an operator to easily access an upper control panel 160 without the need for significant bending. For example, the control unit 150 may have a total height of between approximately 2-3 feet, and preferably about 32 inches. The substantially horizontal cross-section of a majority of the control unit 150 may have widths of between one and two feet, although the lower portion 152 preferably widens at its lower end with the wheels 158 mounted on the lower corners to provide greater stability.

Figure 5A:
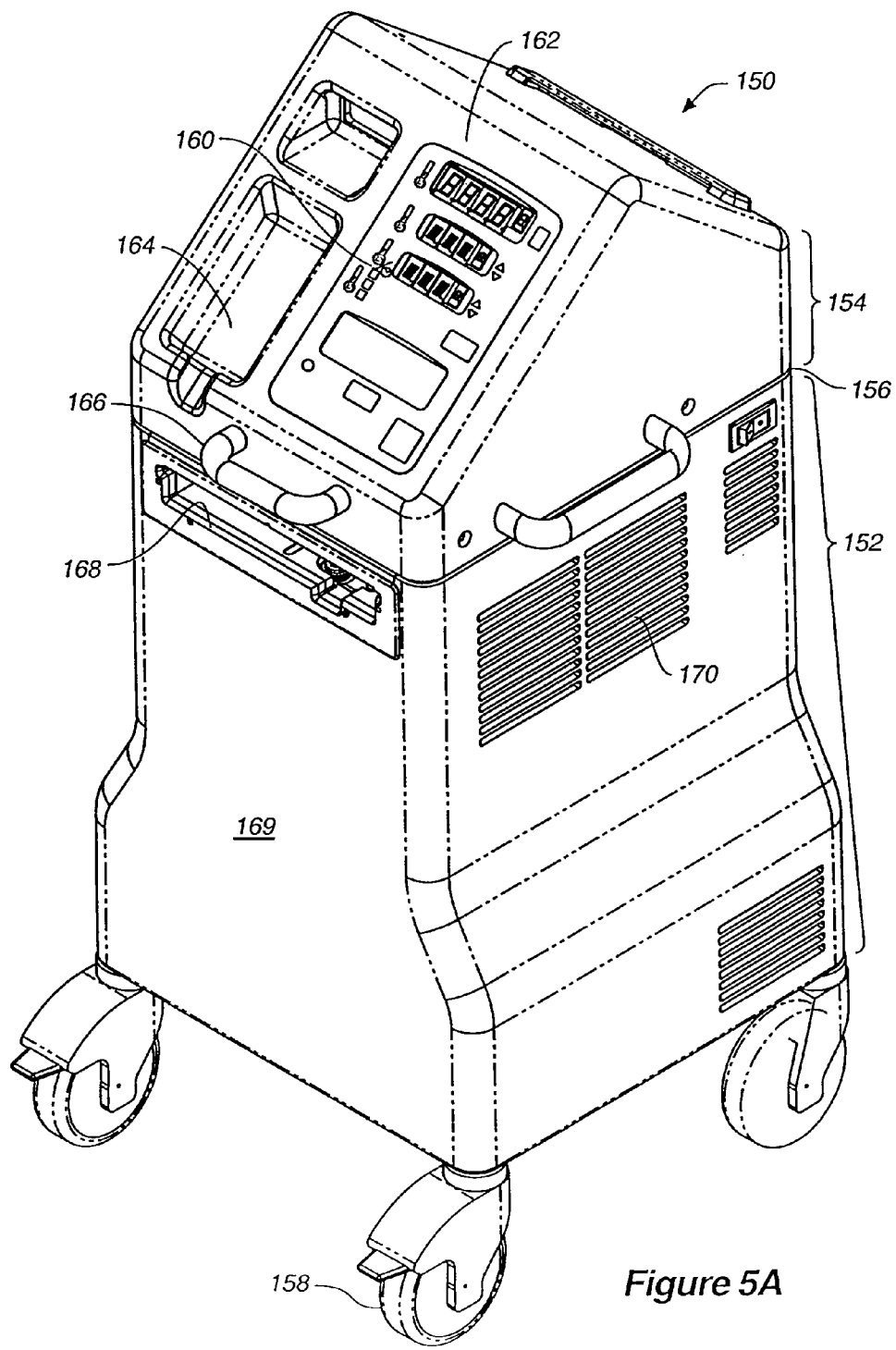
FIG. 5A is a perspective view of an exemplary re-usable control unit of the present invention.

FIG. 5A illustrates the assembled control unit 150, while FIGS. 5B-5G show various exploded views and subassemblies of the control unit. FIG. 5A illustrates the front and right sides of the unit 150 wherein the control panel 160 is visible on an angled upper panel 162 of the upper portion 154 front side. The angled upper panel 162 also defines a fluid container receiving cavity 164 adjacent the control panel 160. Further, a plurality of handles 166 may be provided to help maneuver the control unit 150.

A heat exchange cassette-receiving opening 168 is also provided on a front panel 169 of the control unit 150, just below the horizontal dividing line 156. As will be explained below, the opening 168 is sized and shaped to receive a heat exchange cassette of the present invention, analogous to the heat exchange cassette-receiving opening 102 shown in FIG. 2. Likewise, the control unit 150 provides all of the features that were described above for the control unit 50 of FIG. 2, including a heater/cooler, a pump driver, a controller processor/microprocessor, and a manual input unit, namely the control panel 160.

Because of the relatively high capacity for heating and cooling, the lower portion 152 of the control unit housing includes a plurality of vents 170 to facilitate convective heat exchange between the interior of the housing and the surrounding environment. The control unit housing may be manufactured of a number of suitably strong and corrosion-resistant materials, including stainless-steel, aluminum, or molded plastic. Desirably, the components of the control unit 150 are adapted to run on conventional power from a catheterization lab power outlet, for example.

The present invention also contemplates the use of two different control units in sequence, depending on need. For example, the control unit 150 of FIGS. 5A-5F having a relatively large heat transfer capacity and large housing can be used initially to rapidly alter the patient's body temperature. Subsequently, a smaller unit having an internal battery power source can be substituted for convenience and economy. Both the large and small control units desirably define the same sized and configured cavity for receiving a cassette of the present invention. In this manner, the cassette may be de-coupled from one unit, the patient transported with the cassette in place to another location without the first unit, and the cassette coupled to another unit for a subsequent operation/therapy. The present invention also encompasses a situation wherein the cassette is de-coupled from a first unit and then coupled to a second unit of the same size. This simply obviates the need to transport control units with the patient.

Exemplary Control Panel

Figure 5B:
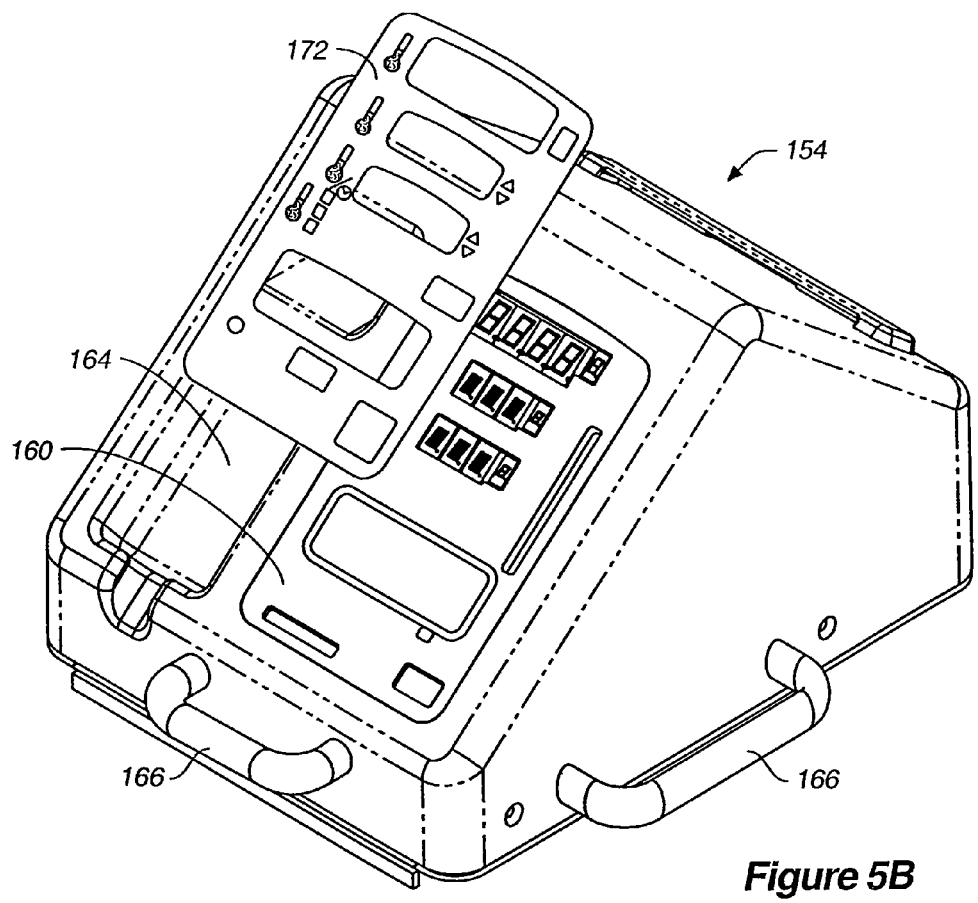
FIG. 5B is a perspective view of an upper portion of the control unit of FIG. 5A.
Figure 5C:
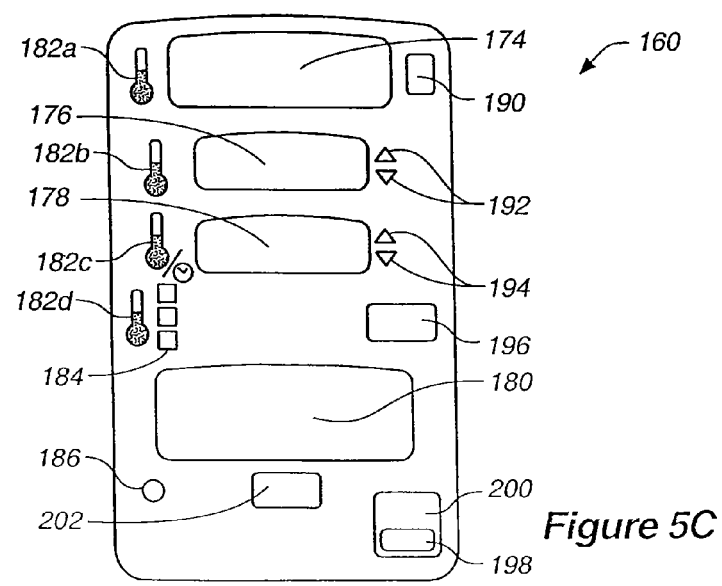
FIG. 5C is a plan view of an exemplary control panel for the control unit of FIG. 5A.
Figure 5D:
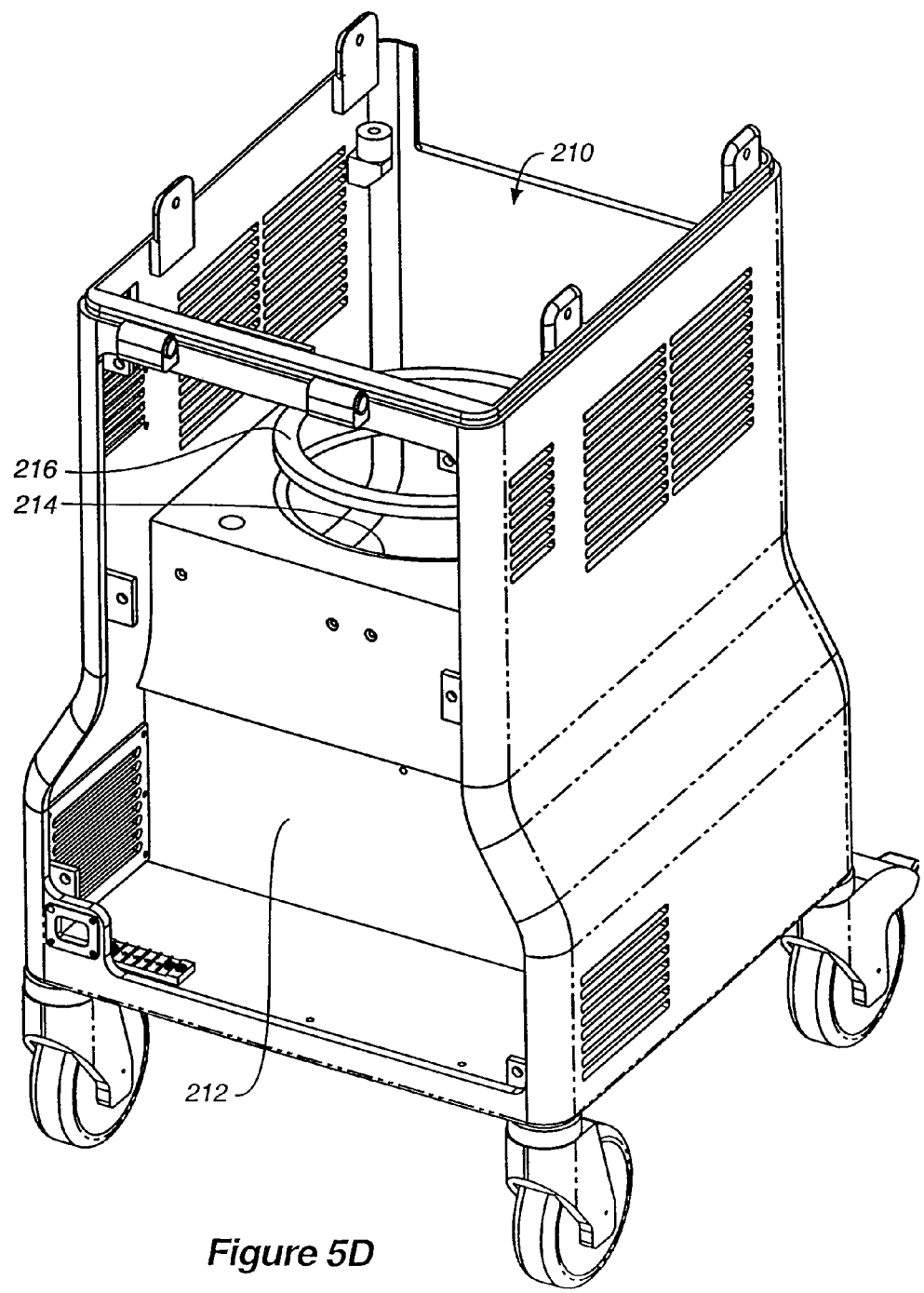
FIGS. 5D-5F are perspective views of a lower portion of the control unit of FIG. 5A having exterior panels removed to expose interior components.

FIGS. 5B and 5C illustrate in greater detail the upper portion 154 of the control unit 150, and in particular the control panel 160. FIG. 5B shows a facade 172 exploded from the control panel 160, with the facade shown in FIG. 5C having indicia printed thereon corresponding to various displays and buttons. (The reader will notice that the control panel 160 in FIG. 5C is an alternative embodiment from one shown in other drawings, and includes several added features and with several buttons and/or displays being slightly relocated). The following is a description of the physical characteristics of the control panel 160, with a description of an exemplary method of using the control panel to follow later in the description.

The exemplary control panel 160 of FIG. 5C provides a number of visual displays, including, from top to bottom along the centerline, a patient temperature display 174, a target temperature display 176, a cooling/warming rate display 178, and a system feedback/status display 180. Other desirable information may be displayed, either with an additional display, or alternating with information displayed on one of the screens shown here, or by user initiated request from one of the screens shown here. For example, by way of illustration but not limitation, if the ramp rate for heating or cooling the patient is set by the user, or is calculated by a control microprocessor, or the projected time to target temperature is calculated, those values may be shown. The larger displays for alphanumeric characters are preferably liquid crystal displays (LCD), while several light emitting diode (LED) status indicators are also provided. Several graphic icons are positioned adjacent the left of the upper three LCD displays 174, 176, and 178, to indicate their respective display functions. Specifically, a patient temperature icon 182a, a target temperature LED 182b, and a cooling/warming rate LED 182c are provided. Just below the cooling/warming rate LED 182c, an operational mode LED 182d and associated vertical series of three mode indicators 184 are provided. Only one of the indicators 184 lights up at any one time, depending on whether the system is in the COOLING, WARMING, or MAINTAINING mode. In lieu of the mode indicators 184, the display 180 may carry the message COOLING PATIENT, WARMING PATIENT, or MAINTAINING so that the operator can easily identify the mode of functioning of the controller. There also may be only one patient temperature icon 182 which has a line of lights that streams upward if the unit is warming, downward if the unit is cooling, and blinks stationary if the unit is maintaining. Finally, a power on/off indicator LED is provided in the lower left corner of the control panel 160.

The control panel 160 also exhibits a number of input buttons including, in descending order on the right side of the control panel, a Celsius/Fahrenheit display toggle 190, a pair of target temperature adjustment buttons 192, a pair of cooling/warming rate adjustment buttons 194, a multi-function/enter button 196, and a mute audible alarm button 198. The mute audible alarm button 198 is nested within an LED alarm indicator 200. Finally, in the lower central portion of the control panel 160, a stop system operation button 202 permits instant shutdown of the system.

Control Unit Housing

Figure 5E:
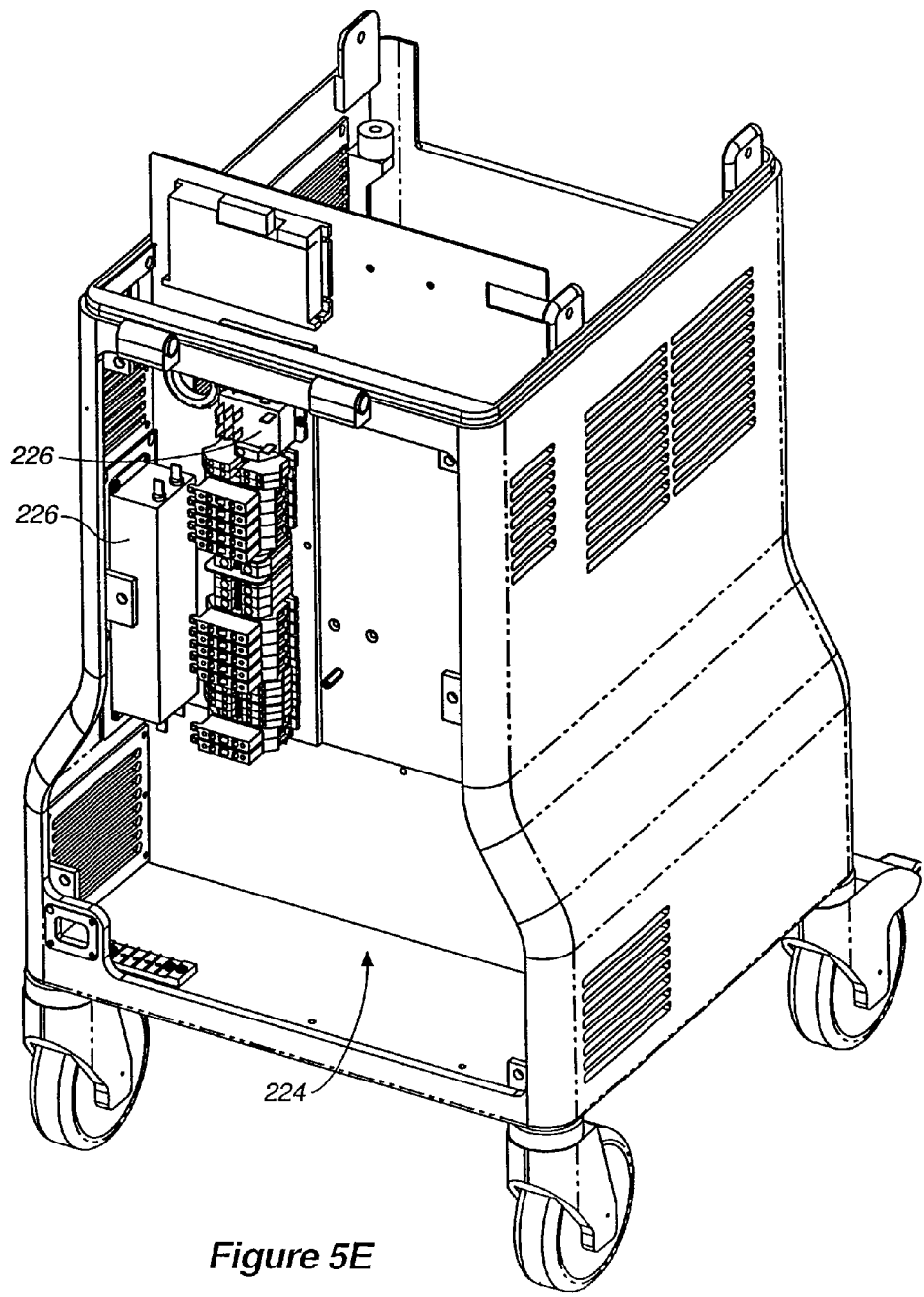
Figure 5F:
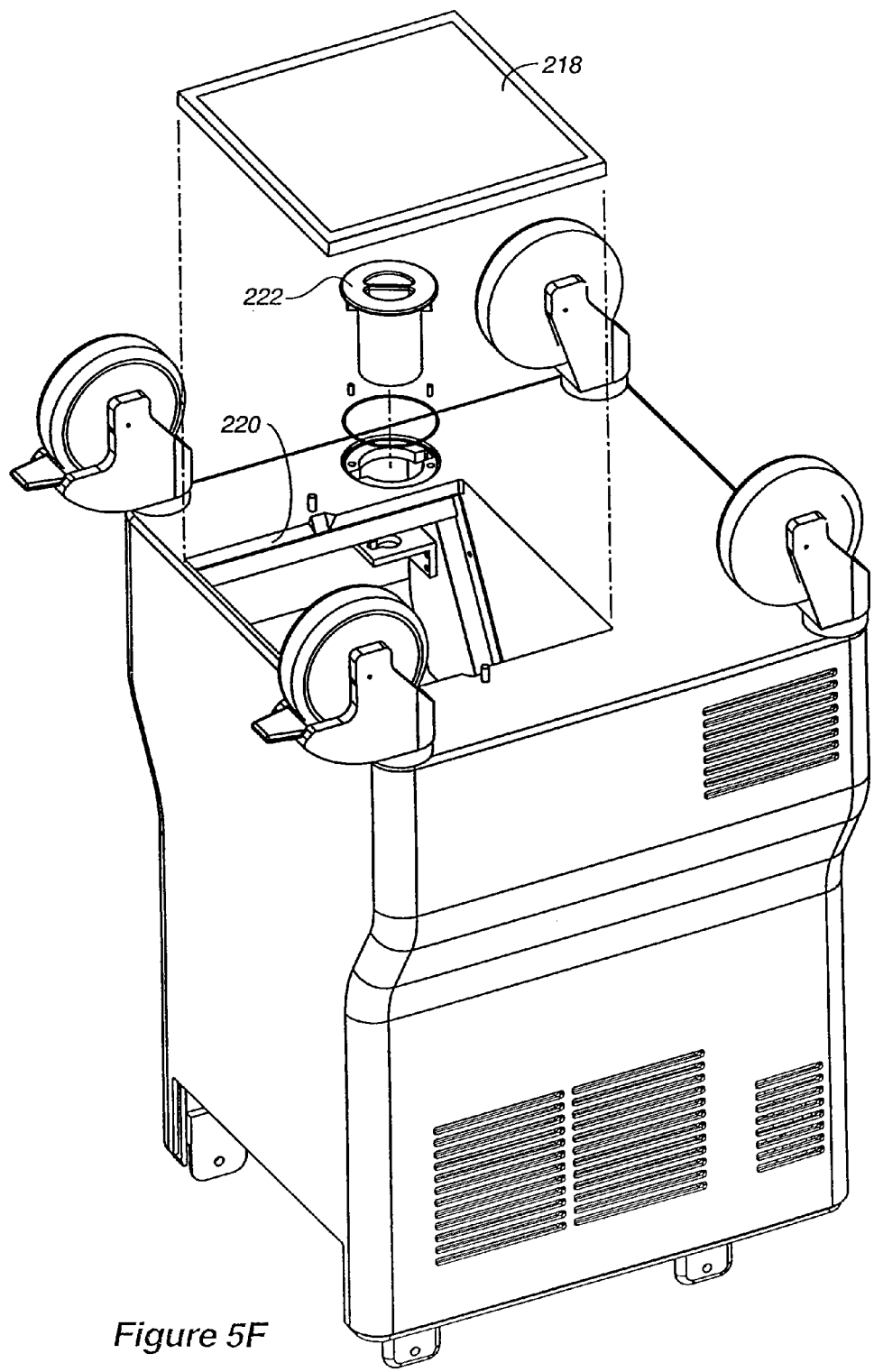

As seen in FIGS. 5D-5G, the control unit housing is defined by a number of panels, some of which can be removed to view and access the interior contents of the control unit 150. For example, in FIGS. 5D and 5F, the front panel 169 (FIG. 5A) has been removed to expose an internal cavity 210 a majority of which is filled by a subhousing 212 enclosing a relatively large blower fan (not shown). As will be explained below, the blower fan within the subhousing 212 interacts with a thermoelectric cooler/heater and is separated therewith by a circular upper opening 214 that receives a gasket 216 to seal about a circular skirt 244 (described below with respect to FIG. 6A). An air filter 218 covers an opening 220 in the bottom of the subhousing 212 within the control unit such that room air pulled into the subhousing 212 through the opening 214 is filtered. Finally, a drain cup 222 may be provided in the bottom of the control unit 150. In FIG. 5E a rear panel has been removed to expose a rear cavity 224 from which a number of electric connectors 226 are accessible.

Figure 5G:
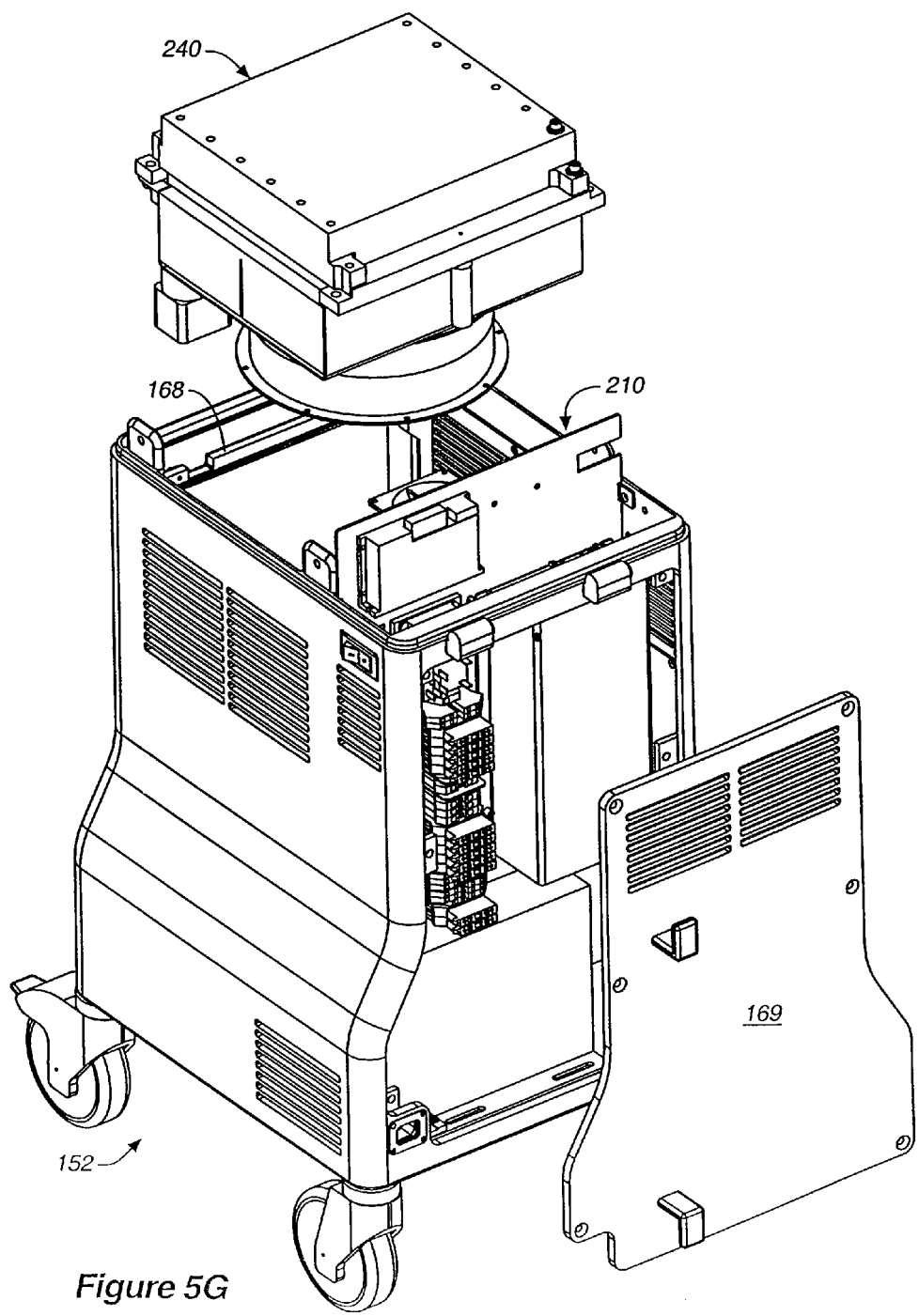
FIG. 5G is a perspective view of the control unit lower portion and showing a heat exchange cassette-receiving subassembly exploded above an inner cavity.

FIG. 5G is a frontal perspective view of the lower portion 152 of the control unit 150 showing a heat exchange cassette-receiving subassembly 240 exploded upward from the inner cavity 210. The subassembly 240 is shown isolated in FIGS. 6A and 6B, and defines a heat exchange cassette-receiving cavity 242 (FIG. 6B) on a front side thereof that registers with the similarly-sized opening 168 in the front panel 169 when the subassembly is within the cavity 210. By this arrangement, a heat exchange unit of the present invention, such as a heat exchange unit 54 of FIG. 2, or a heat exchange cassette as described below, can be inserted through the front panel opening 168 and "plugged-in" to the cavity 242 within the subassembly 240.

Figure 6A:
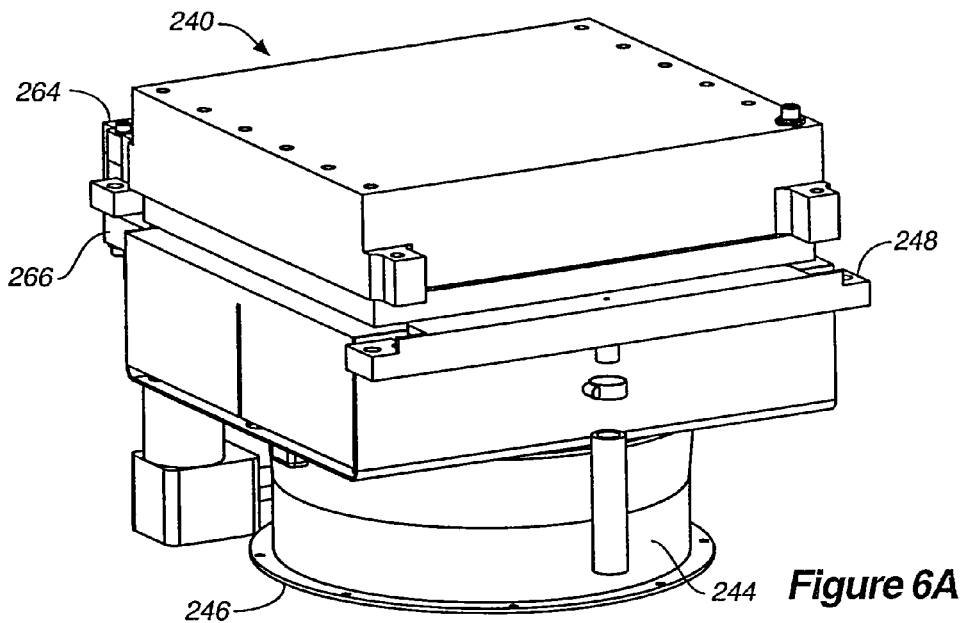
FIG. 6A is a perspective view of the heat exchange cassette-receiving subassembly seen in FIG. 5G.

As seen in both FIGS. 5G and 6A, the tubular skirt 244 depends from the subassembly 240 and includes a lower flange 246 having a series of through holes therein to enable attachment around the circular opening 214 in the blower subhousing 212 (FIG. 5D) with the gasket 216 held therebetween. The skirt 244 thus provides a direct and contained pathway for the air blown upward by the blower for cooling the subassembly 240. Alternatively, the pathway for the air may be reversed, with the blower pulling air downward through the subhousing 212. The subassembly 240 further includes a plurality of mounting brackets 248 that securely attach to a similar number of support brackets provided in the cavity 210 of the control unit 150.

Heat Exchange Cassette-Receiving Subassembly

Figure 6C:
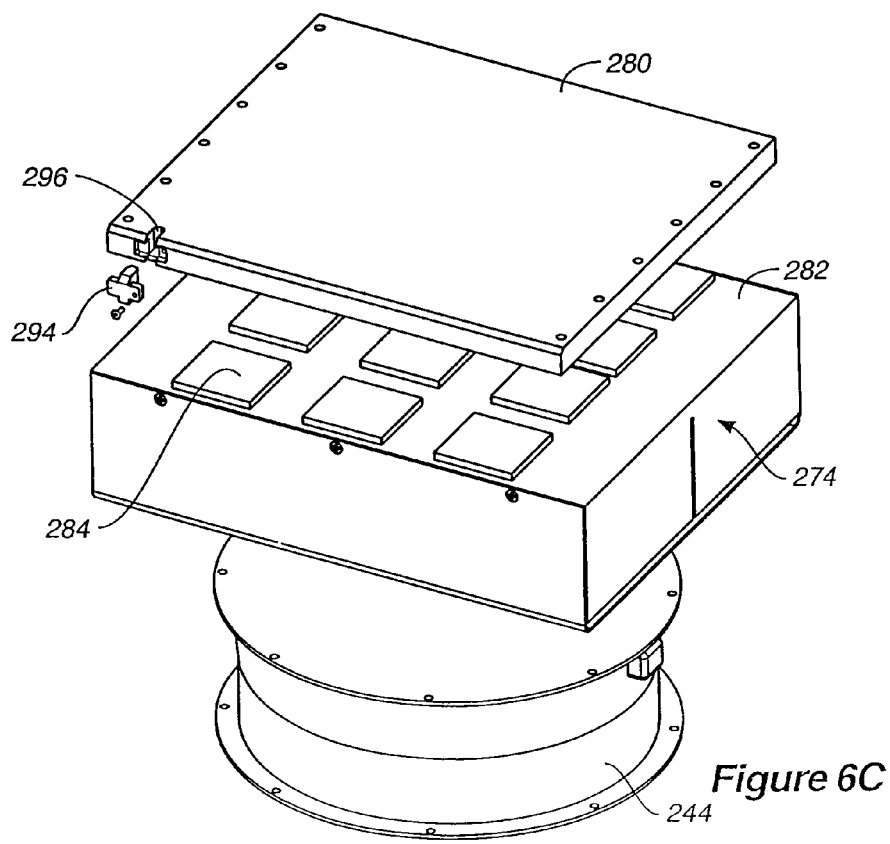
FIG. 6C is an exploded view of a heater/cooler unit of the heat exchange. cassette-receiving subassembly of FIG. 6A.
Figure 6B:
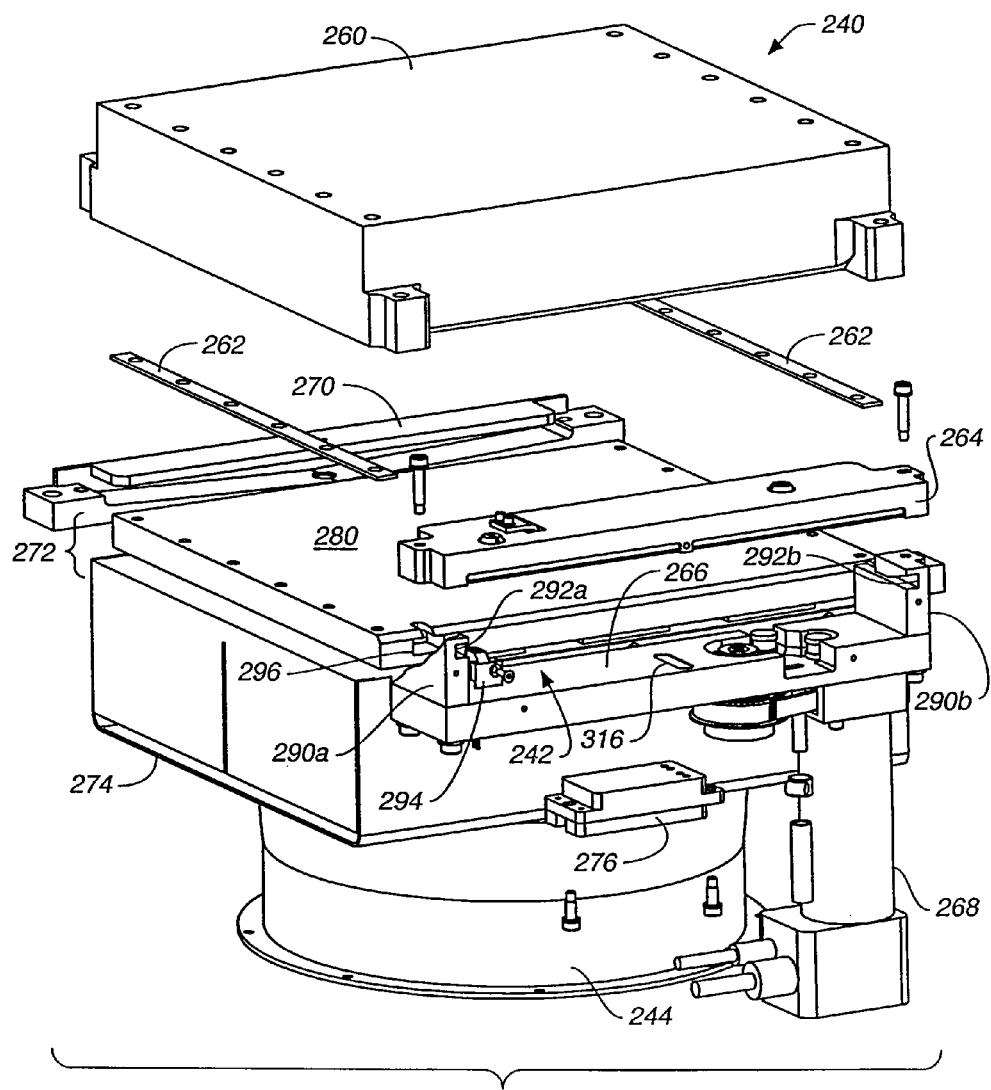
FIG. 6B is an exploded view of the heat exchange cassette-receiving subassembly of FIG. 6A.

FIGS. 6A-6C further illustrate the various components of the heat exchange cassette-receiving subassembly 240 in several views and with several portions removed or exploded. With reference first to FIG. 6B, the subassembly 240 comprises, from top to bottom, an upper pressure plate 260, a pair of elongated side spacers 262, an upper guide assembly 264, a lower guide assembly 266, a pump drive mechanism 268 attached to and depending downward from the lower guide assembly, a rear water channel assembly 270, a heater/cooler subsystem 272, and an air cooler 274 dispose directly below the heater/cooler subsystem. In addition, a fluid level measurement sensor module 276 is shown exploded in FIG. 6B, and is adapted to be mounted to the underside of the lower guide assembly 266.

The air cooler 274 comprises a hollow box-like structure having solid front and rear walls, a circular opening (not shown) in the bottom wall to communicate with the interior of the tubular skirt 244, and a pair of side walls with vents 278 that register with the vents 170 in the surrounding control unit housing. In addition, the air cooler 274 is exposed to the underside of the heater/cooler subsystem 272. This is accomplished by fastening a portion of the heater/cooler subsystem 272 over the open-topped box of the air cooler 274, as will be described in greater detail below with respect to FIG. 6C. In this manner, air blown through the tubular skirt 244 (either upward or downward) flows past the underside of the heater/cooler subsystem 272. If the air is blown upward, it is redirected sideways through the vents 278 and 170 to the external environment. If the air is blown downward, it is pulled in through the vents 278 and 170 and is redirected downward through the first filter in the circular upper opening 214, and out through the second air filter 218 covering the square opening 220 to the external environment. The air cooler 274 therefore acts as a highly efficient convective heat sink for the heater/cooler subsystem 272. Of course, other types of heat sinks and other patterns of convective air cooling may be used, and the present invention should not be considered limited to the air blower 274 shown.

FIG. 6C shows the heater/cooler subsystem 272 exploded with an upper plate 280 separated from a lower plate 282 and between which a plurality of thermoelectric (TE) modules 284 are sandwiched in thermal contact with both. As mentioned previously, the lower plate 282 fastens over the open top of the box-shaped air cooler 274. The TE modules 284 are preferably discrete modules distributed over the surface of the lower plate 282. In exemplary embodiment illustrated, there are twelve square TE modules 284 distributed in rows and columns across substantially the entire area of the lower plate 282. The TE modules 284 preferably function on the well known Peltier principal, wherein the same TE modules may either heat or cool depending on the direction of DC current through the units. Therefore, merely by changing the polarity of the current flowing through the TE module the heater/cooler subsystem can be instantly changed from a heater to a cooler or visa versa. The amount of heat or cold generated can also be adjusted by controlling the amount of current flowing through the TE modules. Thus a very high level of control may be exercised by control of only one variable, the DC current supplied to the TE modules.

The upper plate 280 provides a conductive heat transfer interface between TE modules 284 and the heat exchange cassette inserted within the cavity 242, and tends to distribute the discrete temperature differentials provided by the TE modules 284 over its surface. This helps to prevent localized heating or cooling of the heat exchange cassette, which may provoke an erroneous temperature measurement. Further, the upper plate 280 is manufactured of a suitably rigid metal having good thermal conductivity, such as anodized aluminum or other suitable material. The rigidity of both the upper plate 280 and the upper pressure plate 260 are sufficient to resists bending from fluid pressurization of the heat exchange cassette positioned in the internal cavity 242.

With reference again to FIGS. 6A and 6B, connection of the various components of the subassembly 240 creates the aforementioned internal cavity 242 into which a heat exchange cassette of the present invention can be inserted. In the preferred embodiment, a cassette is provided as described in greater detail below comprising a relatively thick bulkhead portion and a relatively thin external heat exchanger, with the external heat exchanger sized to fit between the upper pressure plate 260 and the upper plate 280 of the heater/cooler assembly 272. In this regard, the lower guide assembly 266 includes a pair of upstanding side walls 290a, 290b each having guide slot 292a, 292b facing inward toward the other. The guide slots 292a, 292b are sized to receive the side edges of the desirably plate-like external heat exchanger and reliably directed it into the narrow gap defined between the upper pressure plate 260 and the upper plate 280. Although not shown, a micro-switch is desirably provided in the slot 292 of one of the upstanding side walls 290 to indicate when the heat exchange cassette has been fully inserted into the internal cavity 242, and is engaged therein for proper operation of the system. Also not shown but well known in the relevant art, registration means such as pressure pins or balls and mating detents may be provided in the control unit and cassette respectively to aid in the correct relative positioning between the cassette and the control unit.

FIGS. 6B and 6C illustrate a thermistor 294 positioned in a similarly-shaped receptacle 296 in one edge of the upper plate 280 of the heater/cooler subsystem 272. The thermistor 294 may be of a standard type well known in the art and generally available, and is secured in the receptacle 296 with a fastener, such as the screw shown exploded in the figures. The thermistor 294 senses the temperature of the upper plate 280 and is connected (not shown) to transmit the information to the control processor of the control unit 150. The temperature of the upper plate 280 provides a surrogate temperature of the heat exchange fluid within the heat exchange cassette positioned in the internal cavity 242. That is, the temperature of the working fluid at the heat exchanger is measured indirectly by sensing the temperature of the upper plate 280. This indirect method has been shown to work adequately, but of course a more direct measurement of the fluid temperature is within the scope of the invention.

Figure 7A:
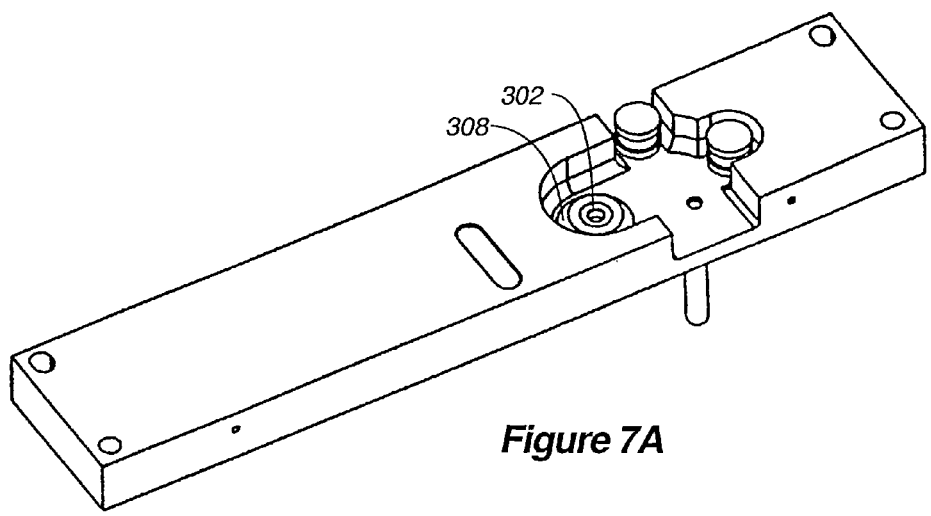
FIGS. 7A-7D are various perspective views of a lower guide assembly and pump drive mechanism of the heat exchange cassette-receiving subassembly of FIG. 6A.

The heat exchange cassette-receiving subassembly 240 further includes a system for driving a pump provided in the heat exchange cassette. More specifically, as mentioned above with respect to FIG. 6B, and as shown in more detail in FIGS. 7A-7D, the pump drive mechanism 268 is attached to the underside of the lower guide assembly 266 for powering a pump in the heat exchange cassette. As shown from below in FIG. 7C, the pump drive mechanism 268 preferably includes an electric motor attached to the underside of the lower guide assembly 266 and having an output shaft (not shown) engaged with a drive belt 300 that, in turn, rotates a pump drive shaft 302 via a pulley 304, the drive shaft being journaled to rotate within a vertical through bore in the lower guide assembly 266. Other alternative methods of transferring rotational motion from the pump drive motor are clearly anticipated by this disclosure and may include a series of gears between the electric motor and the output shaft, a direct drive mechanism whereby the electric motor directly engages the pump in the cassette, or other similar configurations. With respect to FIGS. 7A and 713, the upper end of the drive shaft 302 is located within an irregular channel 306 formed in the top side of the lower guide assembly 266. The upper end of the drive shaft 302 presents a drive gear 308. Although not shown, an exemplary heat exchange cassette of the present invention includes a downward projection that fits within the channel 306 and includes a pump head gear 774 in FIG. 15A that engages drive gear 308. A pair of idler hubs 310a, 310b may also be provided to engage the pump shaft idler wheels and position the pump head gear in engagement with the drive gear 308. A series of related pins and bearings are shown in the drawings, but will not be further explained with the understanding that a skilled artisan would understand the various functional and design alternatives.

Figure 7B:
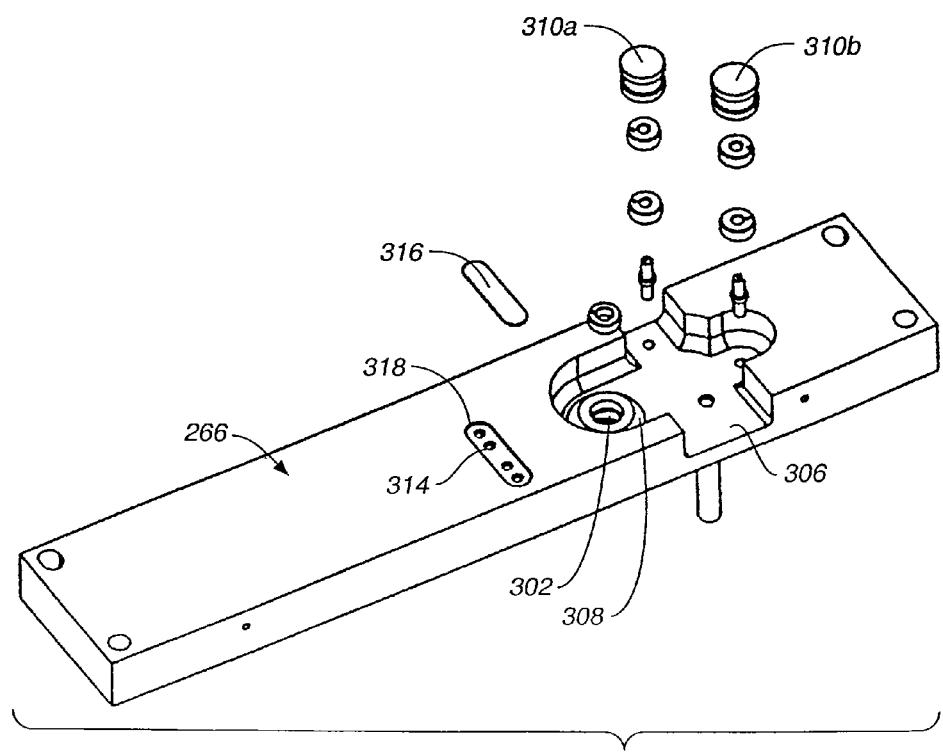
Figure 7C:
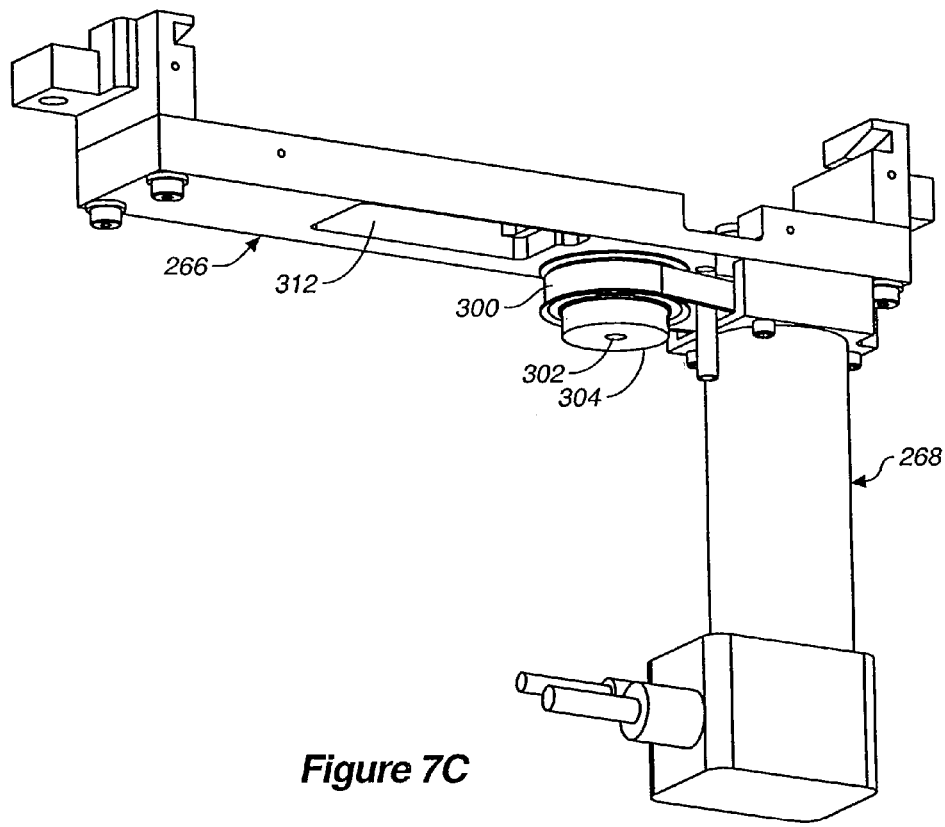
Figure 7D:
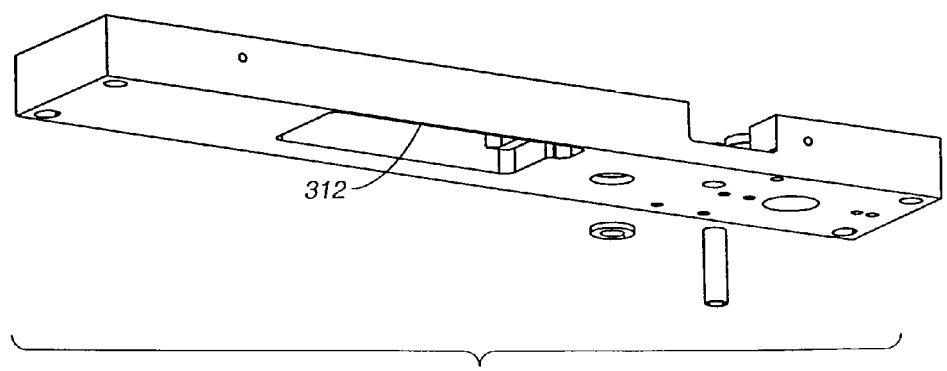

FIGS. 7A-7D also illustrate a cavity 312 formed in the underside of the lower guide assembly 266. A series of through holes 314 extend between the cavity 312 and the top side of the lower guide assembly 266. As seen in FIG. 7B, a transparent window 316 fits into a correspondingly-sized recess 318 and covers the holes 314. A fluid level measurement sensor module 276 seen in FIGS. 6A and 6B fastens within the cavity 312 and includes optical transmitters/sensors that are placed in registry with the openings 314 and interact with the heat exchange cassette to provide an indication of fluid level within the unit, as will be further explained below.

Electronic Control Circuit of the Present Invention

As an alternative to the control system described in conjunction with FIGS. 3A-3B and the graph of FIG. 4, the controller may employ a cascading PID control scheme. In such a scheme, a control system is provided that may be divided into two sections: (a) a Bulk PID control section which takes input from the user (in the embodiment shown, RAMP RATE and TARGET TEMPERATURE) and input from the sensors on the patient representing patient temperature, and calculates an intermediate set point temperature (SP1) and an output signal to the Working Fluid PID control; and (b) the Working Fluid PID control, that receives input from the Bulk PID control section and from a sensor representing the temperature of the working fluid, and generates a signal that controls the temperature of the TE cooler by varying the power input to the TE cooler. The working fluid circulates in heat transfer proximity to the TE cooler, so the Working Fluid PID essentially controls the temperature of the working fluid. In this way, the control scheme is able to automatically achieve a specified target temperature at a specified RAMP RATE based on input from sensors placed on the patient and the logic built into the controller. Additionally, this scheme allows the unit to automatically alter the patient temperature very gradually the last few tenths of a degree to achieve the target temperature very gently and avoid overshoot or dramatic and potentially damaging swings in the electronic power to the TE cooler. Once the target temperature is achieved, the system continues to operate automatically to add or remove heat at precisely the rate necessary to maintain the patient at the target temperature.

Figure 8:
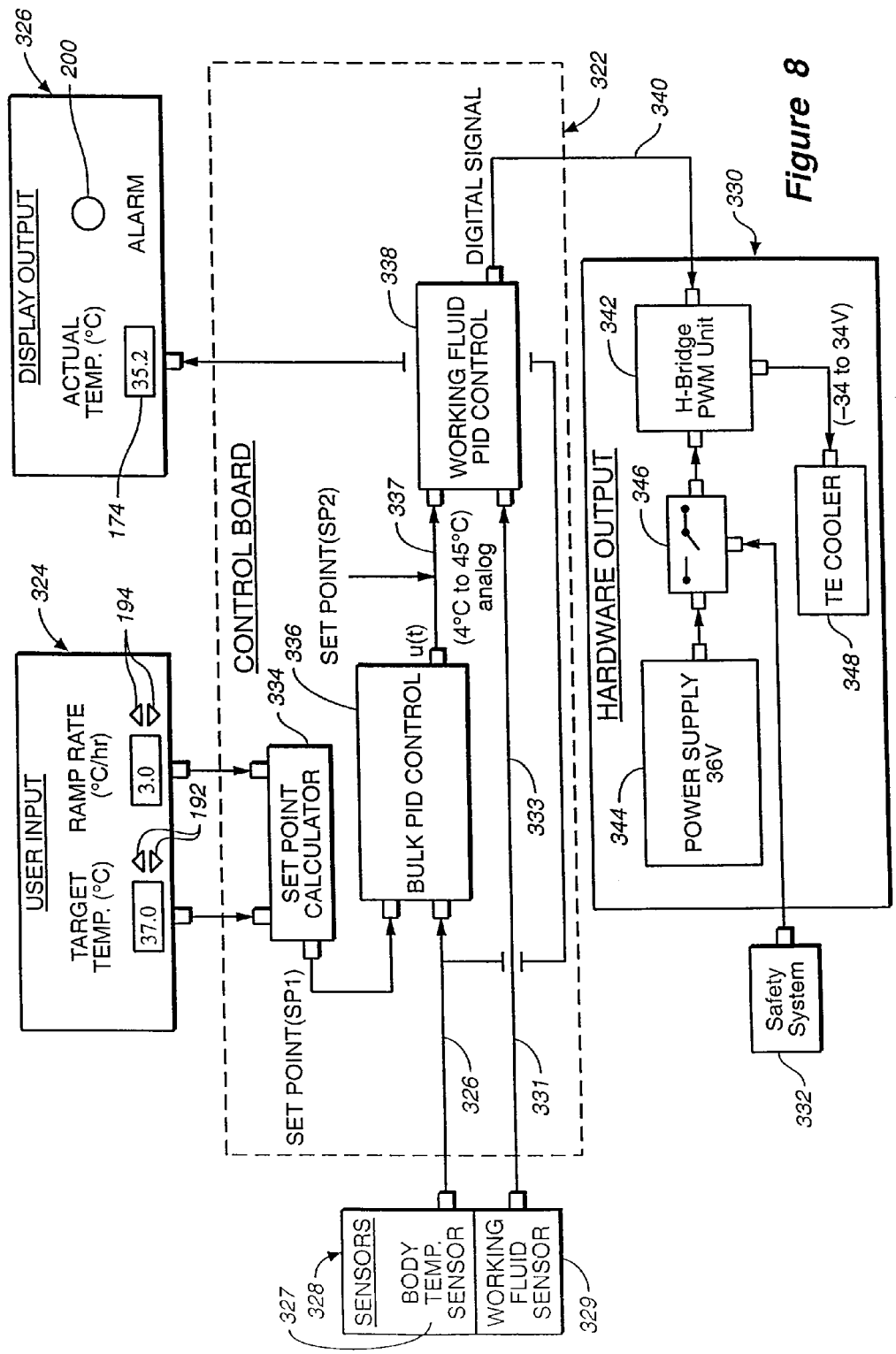
FIG. 8 is a schematic diagram of exemplary components of the present invention; illustrating communication and feedback interconnections therebetween.

Specifically, this is achieved as illustrated in FIG. 8. FIG. 8 illustrates an exemplary control schematic of components of the present invention specifically adapted for use in control unit 150 of FIG. 5A, but applicable to any control unit described herein. Some of these elements correspond to elements identified previously, and thus, where appropriate, reference numbers will be repeated for clarity. In general, the control circuit includes a control board having a number of logical components indicated within the dashed line 322, a user input 324, a display output 326, a plurality of sensors 328, a number of elements of electronic hardware indicated within the box 330, and a safety system 332. The user inputs 324 and display outputs 326 were described above with respect to the control panel 160 of FIG. 5C. The two user inputs 324 applicable to the control circuit in this embodiment are the target temperature adjustment buttons 192 and cooling/warming rate adjustment buttons 194. The display outputs 326 applicable to the control circuit are the patient temperature display 174 and the alarm display 200, but may include a number of other displays for various feedback to the user. A plurality of sensors 328 may be provided, including at least a sensor 327 that senses the patient's actual body temperature and generates a signal represented by line 326, and a sensor 329 that directly or indirectly senses the temperature of the working fluid and generates a representative signal 331. As stated previously, the working fluid may be, for example, saline that is heated or cooled by passing in heat exchange proximity with a TE cooler 348 and then is circulated within a heat exchange catheter.

After the system is primed, a set point temperature (SP1) is determined with a set point calculator 334 using the target temperature and the desire ramp rate as inputs. This set point temperature represents an interim target temperature that the system will achieve at any given time, for example 0.1° C. each 6 minutes, if the ramp rate is 1° C. per hour, starting with the initial patient temperature. This set point temperature is transmitted to a Bulk PID control section 336 of the control board. The Bulk PID control 336 also receives input from the body temperature sensor 327.

Based on the differential between the SP1 and actual body temperature, if any, the Bulk PID control 336 raises or lowers the temperature specified for the heat exchange fluid that will be circulated through the exchange catheter so as to induce a change to the patient temperature at the specified ramp rate. That is, a value for the desired working fluid temperature, or a second set point temperature (SP2), is transmitted to a Working Fluid PID control unit 338 as illustrated at 337. The Working Fluid PID control unit 338 also receives input from the temperature sensor 329 for the working fluid as illustrated at 333. The Working Fluid PID control unit 338 compares the sensed working fluid temperature with the desired working fluid temperature transmitted from the Bulk PID control to determine a differential, if any. Based on this differential, the Working Fluid PID control 338 transmits a digital signal as illustrated at 340 to an "H-Bridge" polarity switching unit 342, which directs power of an appropriate magnitude and polarity to the TE cooler 348 to cause the TE cooler to be heated or cooled toward the desired temperature. This, in turn, heats or cools the working fluid as the system operates to circulate the working fluid in heat exchange proximity to the TE cooler.

The polarity switching unit 342 receives power from a source 344 and transforms that power to the appropriate magnitude and polarity requested by the Working Fluid PID control unit. Between the power source and the polarity switching unit is a safety relay 346 actuated by the safety system 332 that will, in the absence of a safety issue, transmit the power from the power source 344 to the polarity switching unit 342. If the safety system 332 is aware of a safety issue, for example if a low fluid level is sensed, it may direct the safety relay 346 to open and prevent power from the power supply 344 from being directed to the TE cooler 348. In the absence of any safety issue, however, the polarity switching unit 342 transmits the power to the heater/cooler unit 348 in accordance to the request from the Working Fluid PID control unit. Various subsystems of the present invention provide input to the safety system 332, and will be described below when introduced.

The control circuit includes logic that permits rapid heat exchange when the target temperature and the sensed body temperature are relatively far apart, and which slows down the rate of heat exchange as the sensed body temperature nears the target temperature. As the sensed patient temperature and the SP1 become very close, the Bulk PID will dictate only a very small change in the working fluid temperature, and thus the rate of change will become smaller and smaller as the SP1 becomes very close to the sensed patient temperature until the rate of change is essentially non-existent. In this way, the patient temperature very gently is heated or cooled the last few tenths of a degree, avoiding overshoot or dramatic swings from heating to cooling when the body temperature is at the target temperature. As the input TARGET TEMPERATURE is reached, the SP1 and the TARGET TEMPERATURE are essentially the same, and the system operates to set the power to the TE cooler at a level that maintains the necessary working fluid temperature to hold the patient temperature at the TARGET TEMPERATURE. In this way, the system will work to maintain a target temperature with the working fluid maintained at just the right temperature to add or remove heat at the precise rate necessary to maintain that target temperature as essentially a steady state.

The Working Fluid PID control 338 samples its respective inputs at a rate of 10 times a second and updates the output to the polarity switching unit 342 at a rate of once every second, and thus the trends of changing patient temperature are constantly monitored and adjusted. The Bulk PID control 336 samples its inputs at the same rate, and thus a new target temperature or a new ramp rate can be specified by the user with nearly instantaneous system response.

A First Exemplary Heat Exchange Cassette

Suitable heat exchange cassettes for use in the invention are described in U.S. Patent Application 60/185,561 incorporated in full herein by reference. Such catheters are generally described below.

Figure 9:
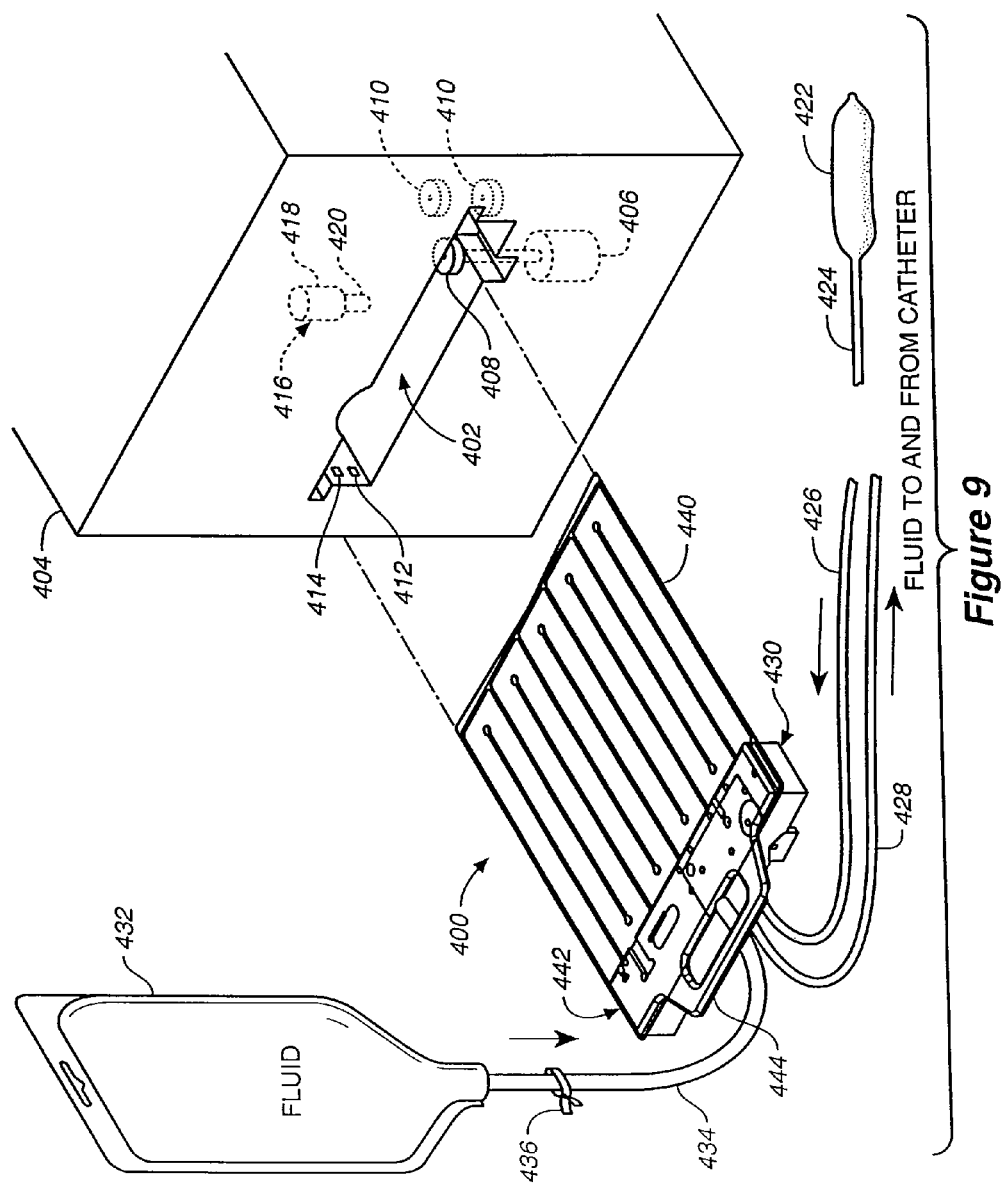
FIG. 9 is a perspective view of a disposable heat exchange cassette attached to a heat exchange catheter and an external fluid source, and positioned for insertion into a suitable opening in the reusable control unit of the present invention.

FIG. 9 schematically illustrates an exemplary heat exchange cassette 400 of the present invention shown adjacent to a receiving opening 402 in a control unit 404. The control unit 404 may be configured like element 50 described above with reference to FIG. 2, or like element 150 with reference to FIGS. 5-8. Consequently, the control unit 404 includes a heater/cooler mechanism (not shown in FIG. 9), a pump drive mechanism 406 (schematically shown), a controller processor, and a manual input device (also not shown in FIG. 9). The pump drive mechanism 406 includes a drive gear 408 and a pair of idler wheels 410, similar to the embodiment shown in FIGS. 7A-7D.

FIG. 9 further schematically illustrates exemplary placement of an optical beam source 412 and optical beam sensor 414 used to determine a fluid level within the heat exchange cassette 400, as will be explained further below. Furthermore, exemplary placement of a valve actuation system 416 including, at least, a linear actuator 418 and push rod 420 is shown. Finally, it will be appreciated by one skilled in the art that the various advantageous features described above with reference to FIGS. 2 and 5-8 may be ascribed to the control unit 404 of FIG. 9.

FIG. 9 illustrates certain aspects of the overall heat exchange catheter system of the present invention, as described above with respect to FIG. 2, including a heat exchanger 422 on the distal end of an in-dwelling catheter 424 through which a heat exchange fluid may be circulated via an inflow line 426 and outflow line 428. The fluid inflow and outflow lines 426, 428 are typically of a flexible compressible material such as polyvinylchloride or other suitable flexible compressible tubing material, and are fluidly connected to a bulkhead 430 of the heat exchange cassette 400. A fluid supply bag 432 supplies heat exchange fluid for priming the system via a supply line 434 which can be closed through the use of a stop cock or pinch clamp 436. Bag size is not generally critical but has a typical capacity of about 250 ml. The disposable heat exchange cassette 400 can be packaged with or separately from the heat exchange catheter 424.

The heat exchange cassette 400 comprises the aforementioned bulkhead 430 to which an external heat exchanger 440 is coupled via a cover plate 442. As mentioned above, the external heat exchanger 440 is substantially flat and thin so as to fit within a narrow slot or gap provided within the control unit 404 and be sandwiched between a heater/cooler plate and a pressure plate. The bulkhead 430 is somewhat thicker and is provided with a handle 444 to facilitate insertion and removal from the control unit 404. Additionally, the bulkhead 430 docks within an outer portion of the opening 402 such that the pump drive mechanism 406 engages a pump head therein. Exemplary details of the pump head will be provided below. (It should be noted that the Figures depict two different embodiments of the bulkhead. The bulkhead shown in FIG. 9 is described in greater detail with respect to FIGS. 10B, 13A-13E and 14A-14E.)

It should also be reiterated that the control unit 404 comprises a re-usable component of the entire system, while the heat exchanger 440, catheter 424, and fluid supply 432 comprise disposable components. Indeed, in a preferred embodiment, all the components except for the control unit 404 are packaged together in a sterile preassembled unit. This arrangement enables the medical staff to set up the entire system by simply opening up the sterile package, "plugging-in" the heat exchange cassette 400 into the control unit 404, and introducing the catheter 424 into the appropriate location in the patient. After the procedure is over, everything but the control unit 404 is disposed of.

Figure 10B:
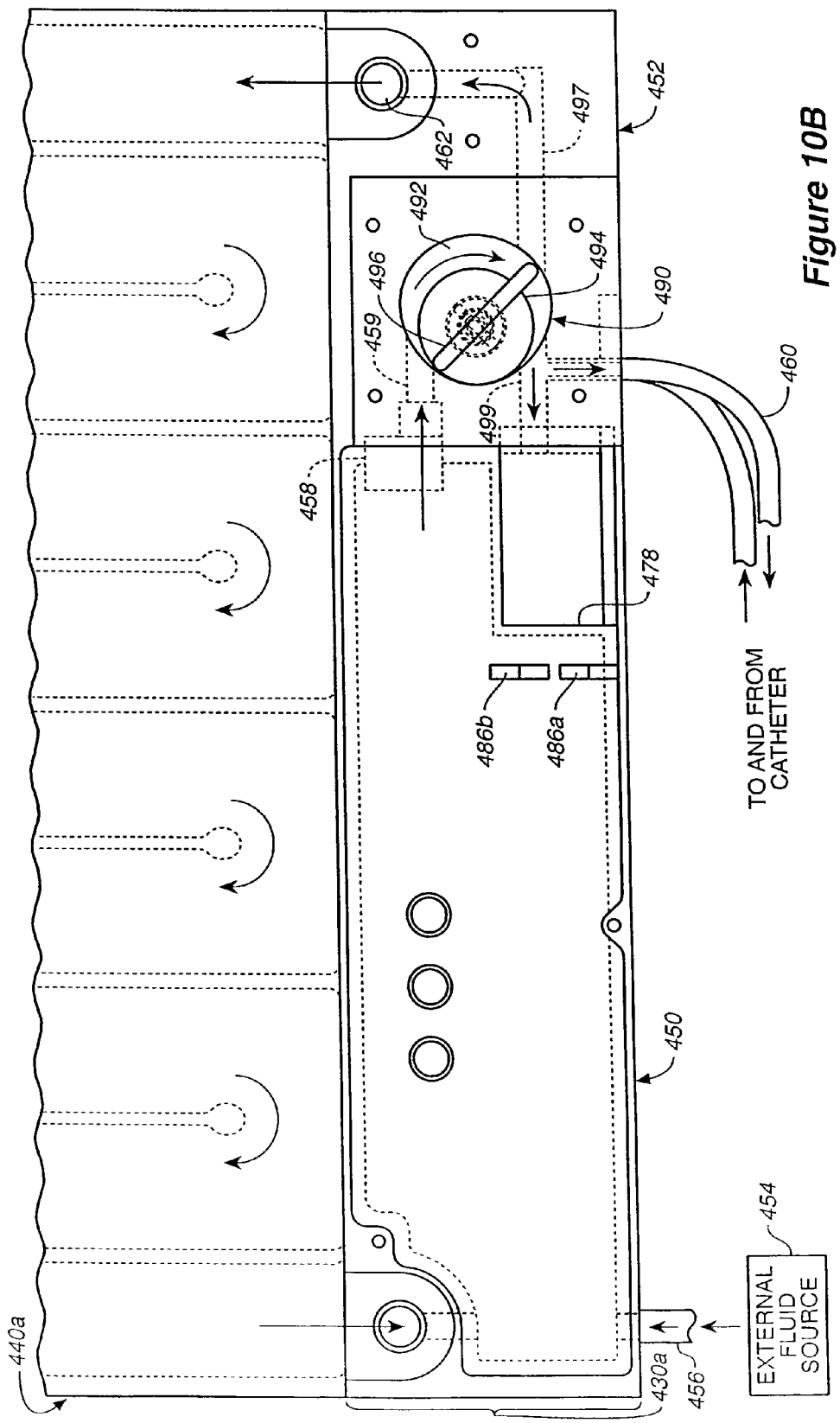
FIG. 10B is a plan view of one end of the heat exchange cassette of FIG. 10A illustrating fluid flow through a bulkhead and attached external heat exchanger.
Figure 10C:
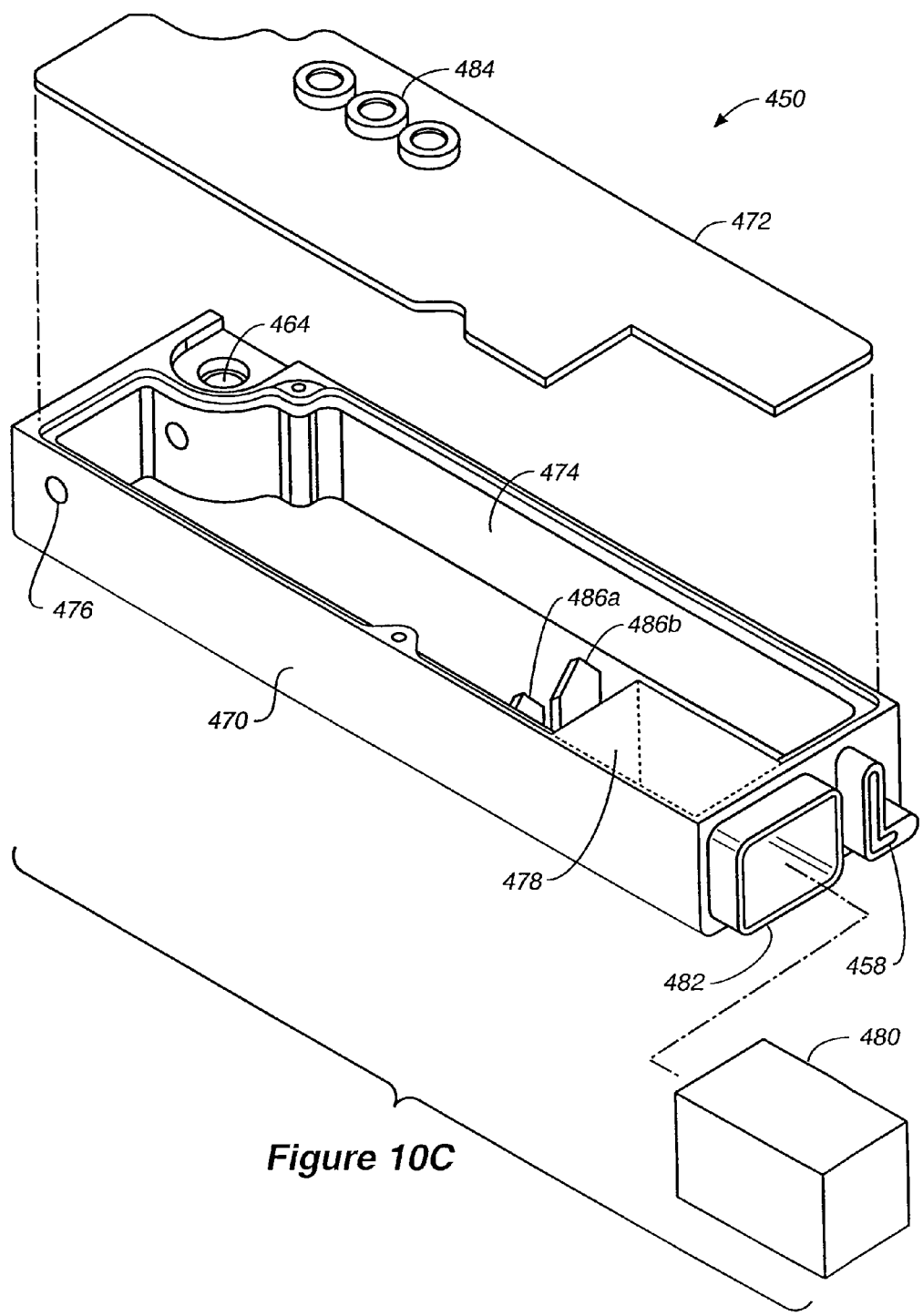
FIG. 10C is an exploded perspective view of a reservoir section of the bulkhead of FIG. 10B.
Figure 10D:
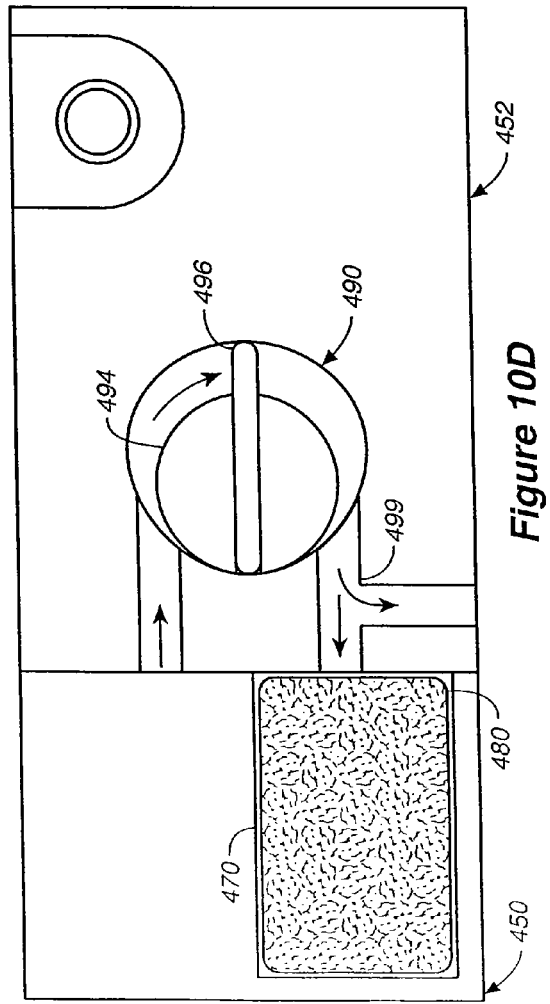
FIG. 10D is a schematic plan view of a fluid pressure damper of the bulkhead of FIG. 10B.

With reference now to FIGS. 10A and 10C-10D, an exemplary heat exchange cassette 400a of the present invention will be described. As described above, the exchange unit 400a includes a bulkhead 430a, an external heat exchanger 440a, and a cover plate 442a. The bulkhead 430a includes a reservoir section 450 and a pump section 452 shown exploded in FIG. 10A, and coupled together for fluid communication in FIG. 10B.

The cutaway plan view of FIG. 10B shows a number of flow arrows that indicate the flow path of heat exchange fluid through the bulkhead 430a and external heat exchanger 440a. Beginning from an external fluid source 454, such as the fluid bag 432 shown in FIG. 9, an inlet line 456 primes the reservoir section 450, and fluid is then pumped to the right in the drawing through an L-shaped outlet channel 458 (FIG. 10C) and into an inlet 459 of the pump section 452. The outlet of the pump section 452 leads to the conduit 460 that supplies the in-dwelling catheter. After circulating through the indwelling heat exchange catheter, the working fluid flows back into a flow-through channel 497 in the pump section 452 and through an outlet 462 on the upper side thereof leading to the external heat exchanger 440a and a flow channel defined therewithin. After passing through the heat exchanger 440a, fluid flows back into an inlet 464 of the reservoir section 450 of the bulkhead 430a.

With reference still to FIGS. 10A and 10C-10D, but with particular reference to the perspective view of FIG. 10C, the reservoir section 450 comprises a lower container 470 that includes, as a top wall, an upper cover plate 472 closely received in a stepped rim of the container and is fastened thereto by a biocompatible adhesive. The container 470 defines a fluid cavity 474 therewithin which receives fluid from two sources: a supply inlet 476 to which the external fluid source conduit 456 attaches, and the inlet 464 connected to the interior of the external heat exchanger 440a. The L-shaped channel 458 provides a fluid outlet located at the end of the reservoir section 450 fluidly connected to the pump inlet 459. Located at the same end of the reservoir as the L-shaped channel is a damping chamber 478 that is not open to the reservoir. A compressible material 480, such as a block of foam, is assembled into the damping chamber 478. The function and advantage of such a damping chamber 478 will be described further below.

Figure 13A:
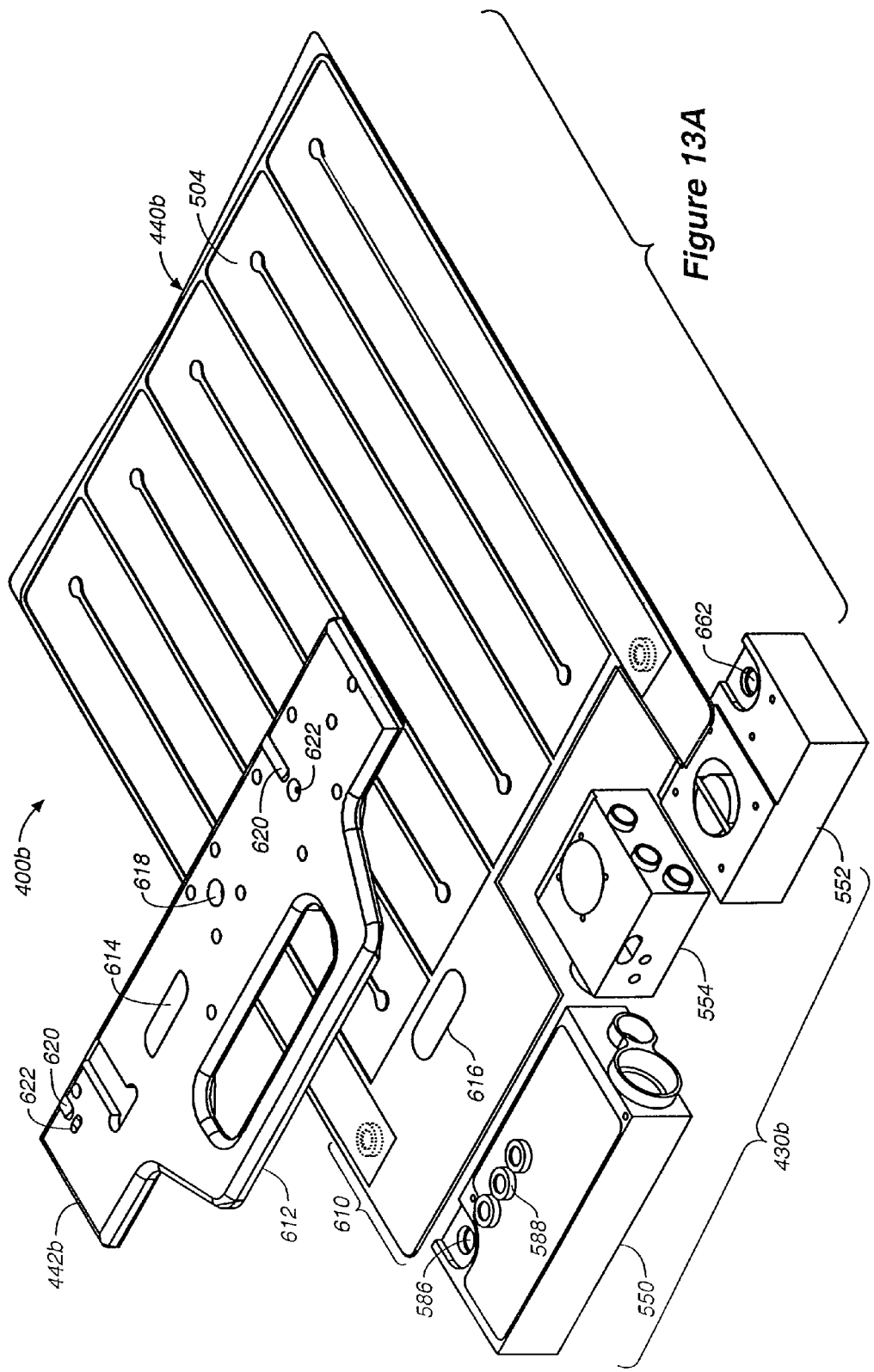
FIG. 13A is an exploded view of a second disposable heat exchange cassette for use in the present invention.

The cover plate 472 seals around the edge of the container 470 to create the fluid cavity 474, but is provided with one or more vent holes 484 fitted with hydrophobic gas permeable vents permitting the release of air from within the cavity. The vent holes 484 permit air to be displaced from within the container 470 when fluid is introduced therein during a system priming operation, without permitting escape of any fluid therefrom. The pore size on the vent holes 484 is small enough to prevent the entrance of any contaminants such as microbes, thus maintaining the sterility of the fluid that is being circulated through the catheter in the patient's body. First and second prisms 486a, 486b are also located within the container 470 as part of a fluid level detection system, to be described further below. The location of the prisms in this embodiment are adjacent the wall of the damping chamber 478, but on the embodiment shown in FIG. 9 are at the other end of the reservoir, and are attached as shown in FIG. 13E at 590a, 590b. As one of skill in the art will readily recognize, the location of the prisms, and the function whether vertical or horizontal is a matter of design choice, and requires concomitant changes in the location of the optical beam sensors 412, 414 in the control unit.

As seen in FIG. 10B, the pump section 452 includes a rotating-type pump head 490 defined within a quasi-cardioid shaped cavity 492 The pump head 490 includes a rotor 494 and a movable vane 496, and rotates on a shaft (not numbered) that is driven by an external source, such as the pump drive mechanism 406 seen in FIG. 9. The pump head 490 is desirably able to pump fluid through the system at pressure in excess of 35 psi and, more preferably, is able to rapidly achieve and maintain a predetermined pressure, for example 40 psi. Specific details of the pump head 490 will be provided below with respect to FIGS. 15-16, it being understood that the rotating-type pump can be a vane pump as shown, an impeller pump, or a gear pump. Furthermore, with some modification, the present system can utilize other types of fluid pumps, such as diaphragm pumps or peristaltic pumps.

The pump section 452 also has the aforementioned flow-through channel 497 having a fluid coupling inlet means 498 that leads from the catheter directly to the outlet 462 leading to the external heat exchanger 440a. As seen in FIGS. 10B and 10D, a diverging pump outlet channel 499 is in fluid communication with a fluid coupling outlet to the catheter 460, and also to the pressure dampening chamber 478. The pressure damping chamber may be filled with, for example, a block of compressible material 480 in fluid communication with the fluid flowing to the catheter. If fluid from the pump flowing to the catheter is experiencing pressure fluctuations, the fluid is exposed to the compressible material 480 within the dampening chamber 478, and as fluid column contacts the compressible material 480, the material compresses slightly or expands slightly, and in doing so acts to absorb pressure fluctuations in the fluid that may result from the action of the pump. The compressible material thus has the effect of dampening pressure pulses in the fluid flow to the catheter.

Suitable examples of the compressible material include a block of foam, encapsulated foam such as polyethylene foam encased in a polyethylene film, foam enclosed within a sealed plastic pouch, foam coated with or impregnated with plastic or silicone, gas encapsulated within a flexible pouch such as a polyethylene balloon, and so forth.

Exemplary External Heat Exchanger

The external heat exchanger shown as 440 in FIG. 9 and 440a in FIG. 10A can be any combination of one or more structural and compliant members such that the overall configuration of the external heat exchanger is adapted to mate with the opening provided in the control unit 404a. In a preferred embodiment, as seen in the cross sections of FIGS. 11A and 11B, the structural member comprises a planar back plate 500 and the compliant member comprises a layer 502 of flexible, thermally conductive material. The compliant layer 502 is sealed to the back plate 500 in a pattern which forms a serpentine flow channel 504 therebetween, as seen in FIG. 10A. The flow channel 504 includes a fluid inlet orifice 506 provided with a flow fitting 508, and a fluid outlet orifice 510 provided with an identical flow fitting 512. The flow fittings 508 and 512 are seen in perspective in FIGS. 12A and 12B.

The back plate 500 is typically stiff and made of a high density polyethylene and is generally about 0.762 mm (0.030 inches) thick. The thinner compliant layer is shown in this embodiment as being sealed in a serpentine pattern to the back plate by fusing, such as by heat sealing or other suitable technique to permanently adhere the two layers together. The pattern of heat sealing creates a serpentine pathway composed of sealed portions 514 separating the continuous serpentine flow channel 504 or, alternatively, a plurality of flow channels.

The winding flow channels 504 form a pathway which causes the heat exchange fluid to flow back and forth adjacent to and in heat transfer relationship with the heater/cooler device within the control unit 404a, and ensures that the fluid circulates proximate to the heat heater/cooler device for a sufficient amount of time to allow for adequate heating or cooling of the fluid. The present invention also may utilize sealed portions that are not continuous, as long as the sealed portions are configured so as to create channels that permit fluid flow through the external heat exchanger 440a. In addition, the external heat exchanger can be configured to have a V-shaped leading edge 516 that acts as a guide to facilitate placement into the control unit 404.

Figure 11A:
FIGS. 11A and 11B are sectional views take along line 11-11 through the external heat exchanger of FIG. 10A, and showing the heat exchanger in its uninflated and inflated states, respectively.
Figure 11B:

The thinner compliant layer 502 is generally about 0.102-0.203 mm (0.004-0.008 inches), and is typically a low density polyethylene material that is slightly elastomeric or compliant so that when pressurized heat exchange fluid flows into the legs of the serpentine channels 504, they bow out slightly as may be seen by comparing FIG. 11A (uninflated) and FIG. 11B (inflated). Since the back plate 500 and thinner compliant layer 502 are both polyethylene, they weld together effectively by means of heat fusion or ultrasonic welding. However, the bulkhead 430a is not the same material, and therefore the external heat exchanger is generally sealed to the bulkhead by other means, such as by a mechanical pressure seal.

As seen in FIG. 10A, the external heat exchanger 440a is provided with an extended attachment 520 that is sealed to the bulkhead 330. The extended attachment 520 has three sections distributed across the bulkhead 330; a first flap section 522a, a cutaway section 522b, and a second flap section 522c. One or more vent holes 524 are cut into the first flap section 142 to allow air to vent from the corresponding number of hydrophobic gas permeable vents 484 in the reservoir cover plate 472, as was described above. While a plurality of vent holes 524 is shown in the embodiment of FIG. 10A, any suitable shape or number of holes will suffice, for example a single vent hole is shown in the embodiment of FIG. 13A, infra.

As mentioned, each of the orifices 506, 510 opening to the serpentine channels 504 is provided with a fitting 508, 512 that allows fluid to flow into the space between the thin compliant layer 502 and the back plate 500. When heat exchange fluid is pumped into the inlet orifice 506 through the first fitting 508, it winds its way along the serpentine path to the outlet orifice 510 and then enters the bulkhead through the second fitting 512. The entire external heat exchanger 440a is placed in thermal contact with a heater/cooler within the control unit 404, such as the heat exchange surface of a thermoelectric cooler or a number of TE cooler modules in contact with a thermal plate (as shown in FIG. 6C). The thinner compliant layer 502 is positioned against the heat exchange surface so that the temperature of heat exchange fluid may be controlled by controlling the temperature of the surface and pumping fluid through the external heat exchanger.

Figure 12A:
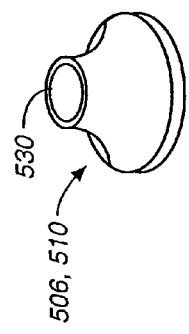
FIGS. 12A-12B are inverted perspective views of an exemplary fluid fitting for use with the external heat exchanger of FIG. 10A.
Figure 12B:
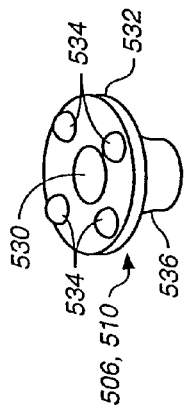

The fittings 508, 512 are secured within the inlet and outlet orifices 506, 510 by virtue of their particular construction, as illustrated in FIGS. 12A and 12B. Each fitting 506, 510 has a central channel 530, a base plate 532, a plurality of spacer protrusions 534 on the lower surface of the base plate, and a nose 536 projecting in the opposite direction from the base plate 532. The embodiment of FIG. 12B illustrates four such protrusions but the invention contemplates having fewer or more than four protrusions. When the fitting 506 is placed in the external heat exchanger 440a, the nose 536 projects through the inlet orifice 506, and the base plate 532 is tightly positioned between the compliant layer 502 and the back plate 500. The spacer protrusions 534 space the base plate 532 away from the back plate 500 of the external heat exchanger. At the outlet orifice 510, fluid contained within channels 504 passes between the protrusions, through channel 530, and then into bulkhead 430a. Similarly, fluid returning from the heat exchange catheter enters the heat exchange channels 504 through the central channel 530 in fitting 506, and passes between the protrusions 534. Two O-rings, such as flexible rubber washers, can be positioned around the periphery of the nose 536 of each fitting 506, 510 between the compliant layer 502 and the bulkhead 430a. The noses 536 of each fitting 506, 510 are sized to be inserted into the associated outlet 462 and inlet 464 of the bulkhead 430a.

A Second Exemplary Heat Exchange Cassette

FIGS. 13A-13E illustrate a second exemplary heat exchange cassette 400b that is in many ways similar to the first-described heat exchange cassette 400a, but has a bulkhead assembly that includes a feedblock section and pressure valve as described below. As in the earlier embodiment, the exchanger 400b includes a bulkhead assembly 430b coupled to an external heat exchanger 440b through the use of cover plate 442b. The bulkhead assembly 430b includes a reservoir section 550 a pump section 552 and a feedblock section 554 disposed therebetween. These three sections can be independent and discrete units that are coupled together, as seen in FIG. 13A, or may be defined within a single unit. The bulkhead section(s) can be machined, molded, or cast, and are typically made of the durable, lightweight material such as plastic or PLEXIGLAS.

Figure 13B:
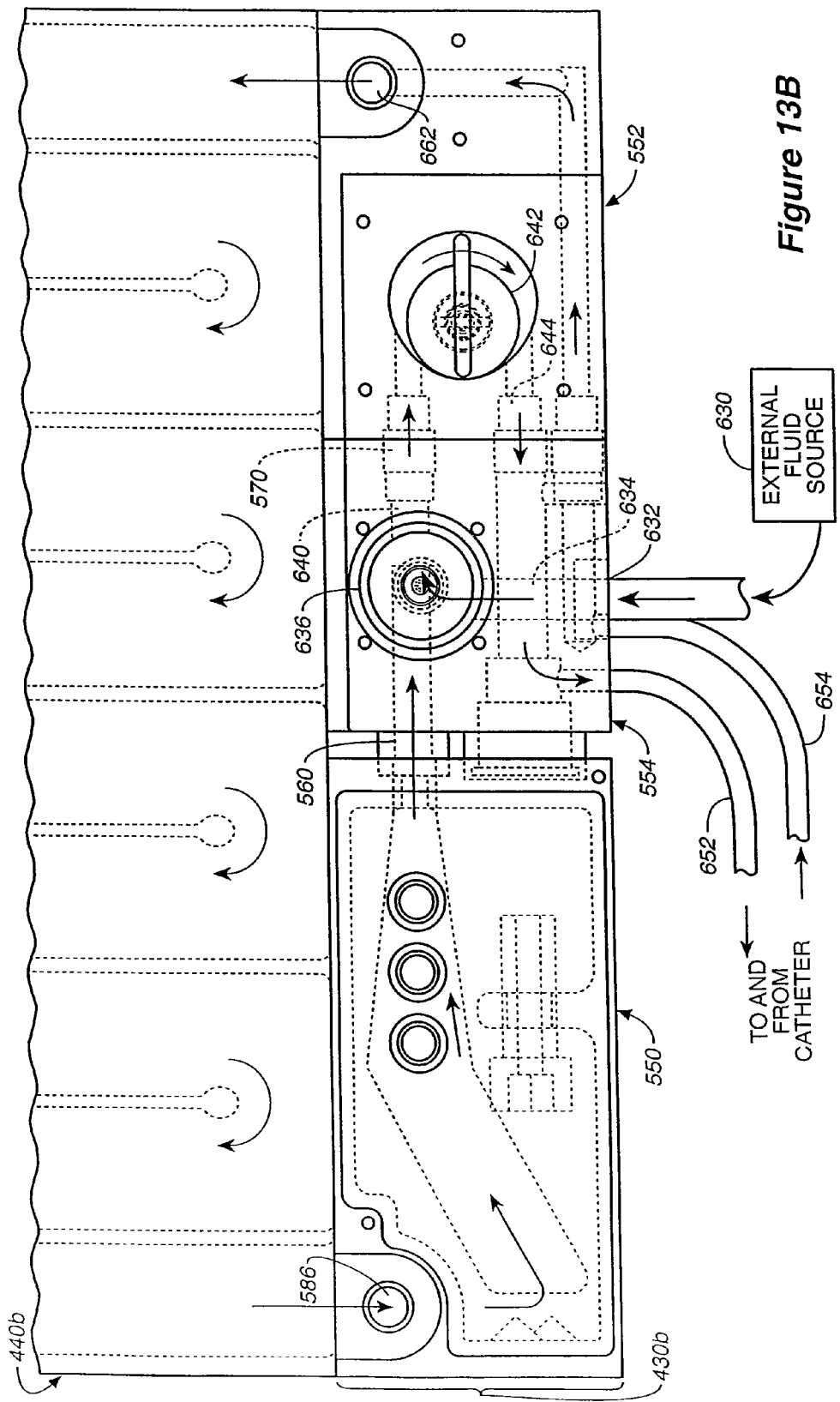
FIG. 13B is a plan view of one end of the heat exchange cassette of FIG. 13A illustrating fluid flow through a bulkhead assembly and attached external heat exchanger
Figure 13E:
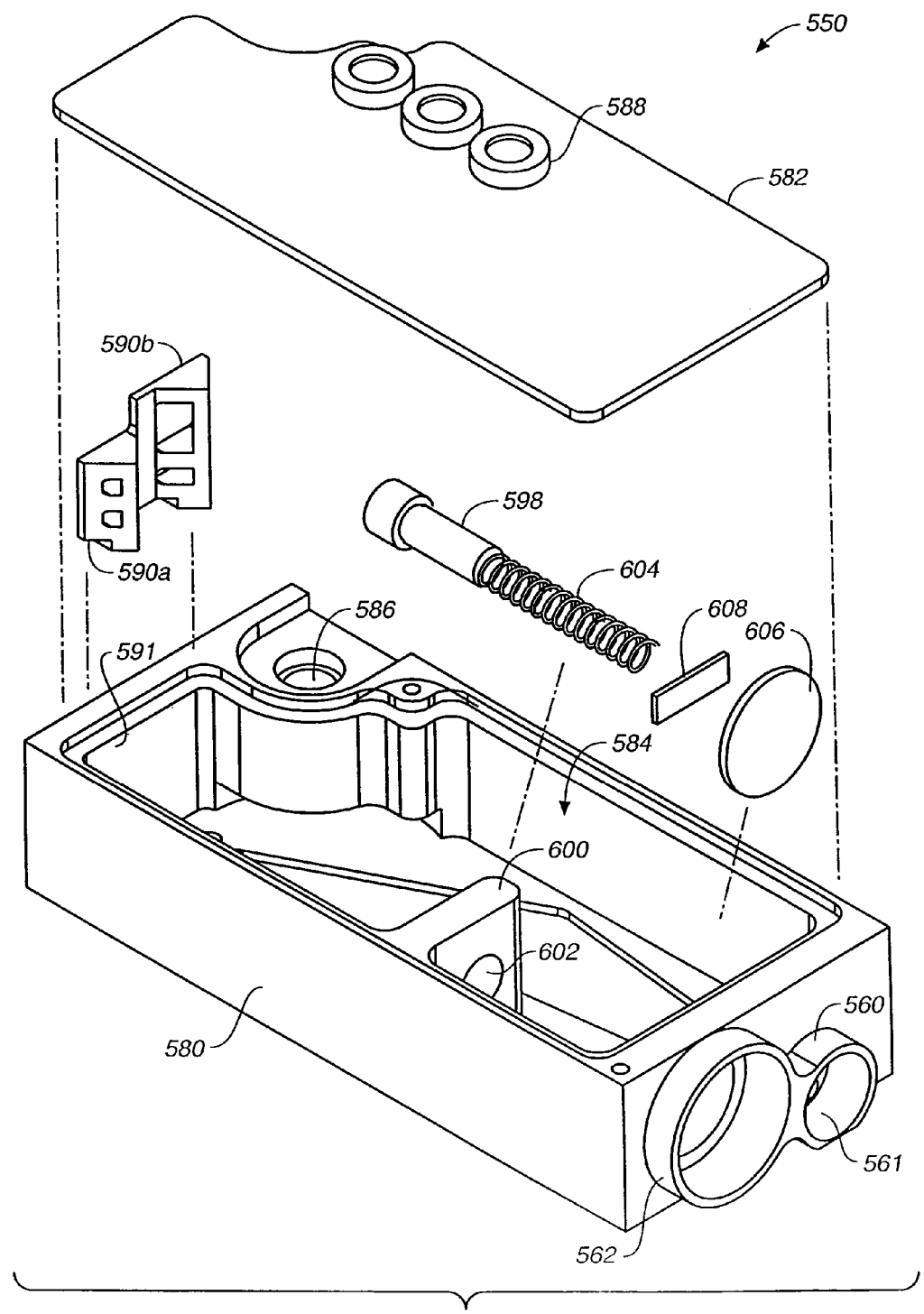
FIG. 13E is an exploded perspective view of a reservoir section of the bulkhead assembly of FIG. 13B.
Figure 14A:
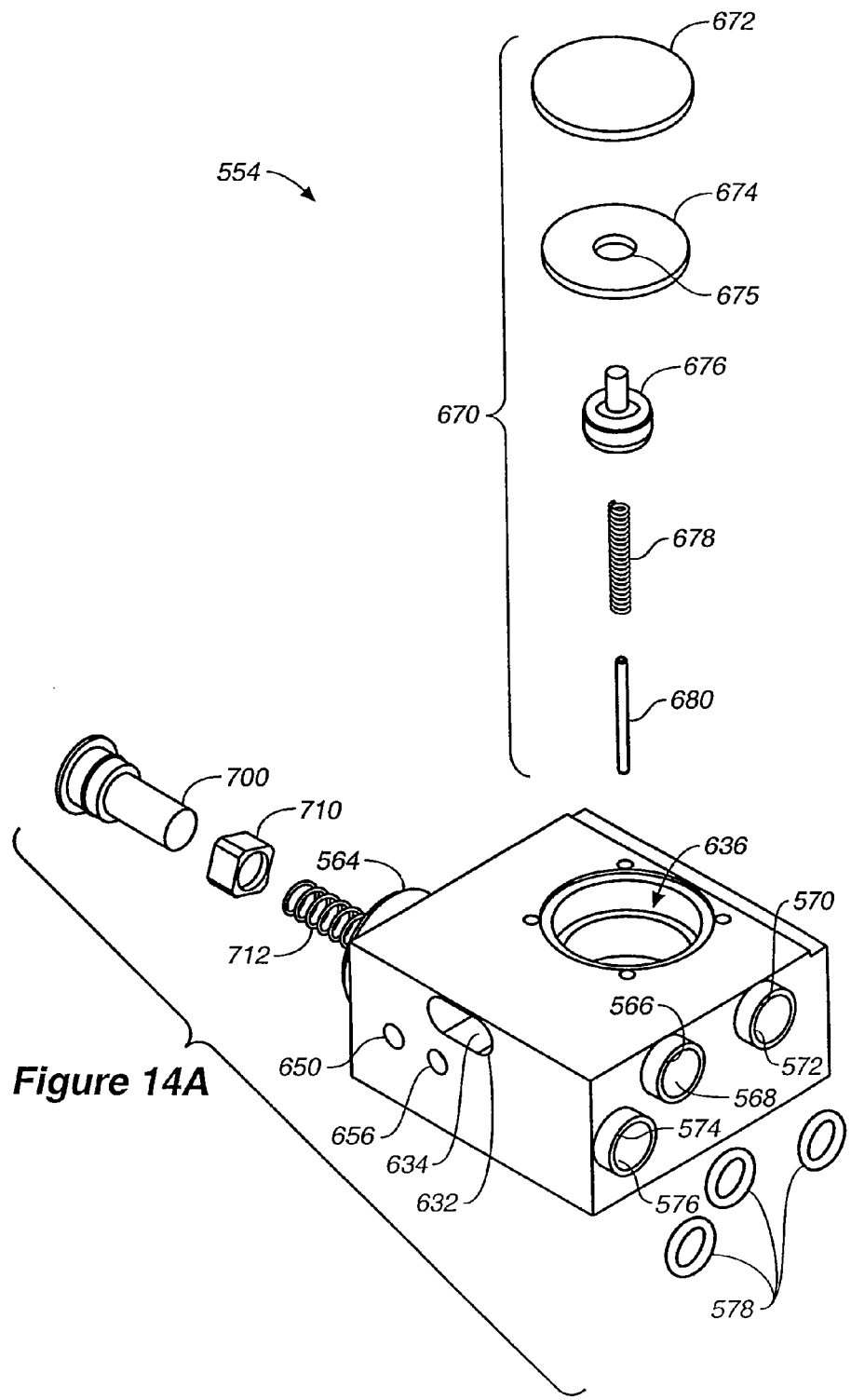
FIG. 14A is a perspective exploded view of a feedblock section of the bulkhead assembly of FIG. 13B.

With reference to the perspective views of FIGS. 13A and 13E, the hollow reservoir section 550 has an elongated rectilinear shape with a pair of collars on one longitudinal end facing the feedblock section 554: namely, a fluid outlet collar 560 defining a reservoir outlet channel 561 and a pressure regulator collar 562. These two collars securely engage two collars of slightly smaller size on the juxtaposed end of the feedblock section 554; specifically, as seen in FIG. 14A, a fluid inlet collar (not shown) and a pressure sensing chamber collar 564. The feedblock section 554 is also a hollow, generally rectilinear housing and includes, on the side facing the pump section 552, an inlet collar 566 leading to an inlet conduit 568, a first outlet collar 570 opening from a first outlet conduit 572, and a second outlet collar 574 opening from a second outlet conduit 576. A series of O-rings 578 are sized to fit around each of these collars 566, 570, 574 and ensure fluid tight seals between the collars and associated openings formed in the juxtaposed side of the pump section 552.

a. Exemplary Reservoir Section

With reference still to FIGS. 13A-13E, but with particular reference to the perspective view of FIG. 13E the reservoir section 550 comprises a lower container 580 that includes, as a top wall, an upper cover plate 582 closely received in a stepped rim of the container which may be further affixed with adhesive or heat welding or other acceptable fastening method. The container 580 defines a fluid cavity 584 therewithin which receives fluid from a single source: an inlet 586 connected to the interior of the external heat exchanger 440b. The cover plate 582 seals the fluid cavity 584 around the edge of the container 580, but is provided with one or more vent holes 588 fitted with hydrophobic gas-permeable vents permitting the release of air from within the cavity during a priming operation.

First and second prisms 590a, 590b are also located within the container 580 adjacent a transparent bulkhead material or window 591 as part of a fluid level detection system. As seen in FIG. 13D, the lower container 580 can be configured so as to have an indented or sloped area 592 in the base. The sloped or indented area defines a fluid channel or sump from the interior fluid cavity 584 of the reservoir adjacent the prisms 590a, 590b to the fluid outlet 561. In this way the fluid opening leading to the reservoir outlet channel 561 is at approximately the same elevation as the prisms 590a, 590b which will therefore assure fluid to the pump even if the level of fluid at the prisms is quite low. As will be discussed below, the prisms are safety systems for detecting low fluid level, a potentially dangerous condition, and the indented area 592 adds extra insurance that a low fluid level will be detected before an absence of fluid to the pump becomes a problem.

As seen in FIG. 13E, a pressure regulator shaft 598 mounts in the fluid reservoir cavity 584 through a mounting flange 600 extending into the cavity from one of the side walls of the container 580. In one embodiment, the pressure regulator shaft 598 includes threads which mate with internal threads provided in a through hole 602 in the flange 600. A reference spring 604 is biased between the shaft 598 and a diaphragm 606. The diaphragm 606 may be a membrane, for example, a cloth-reinforced silicone membrane. Because of the presence of the hydrophobic gas permeable vents 588, the pressure on the reservoir side of the diaphragm 606 is essentially atmospheric pressure plus the pressure applied by reference spring 604. The pressure of reference spring 604 may be adjusted by advancing or retracting the shaft 598 within the threaded hole 602, which in turn adjusts the amount of spring force applied against the diaphragm. A pressure plate 608 is interposed between the diaphragm 606 and the reference spring 604 to more evenly distribute the pressure of the spring to the reservoir side of diaphragm. Further specifics of this exemplary pressure regulating mechanism of the present invention will be described below.

b. Cover Plate

As with the earlier described heat exchange cassette 400a, the external heat exchanger 440b of FIG. 13A includes an extended attachment flange 610 that is secured to the upper side of the bulkhead assembly 430b by the cover plate 442b. Preferably, a mechanical seal is formed between the attachment flange 610 and the bulkhead assembly 430b by virtue of a number of fasteners (not shown) extending between the cover plate 442b and the bulkhead assembly. The cover plate 442b includes a handle 612 for ease of manipulation of the heat exchange cassette 400b.

The cover plate 442b further includes a plurality of apertures and grooves that interact with the bulkhead assembly 430b, and also with the re-usable control unit of the present invention, such as the exemplary control unit 404 of FIG. 9. For example, an elongated aperture 614 registers with a similarly shaped aperture 616 in the attachment flange 610, both apertures permitting passage of air from the reservoir section vents 588. The cover plate 442b further has a priming valve aperture 618 that permits access to a flexible diaphragm of the feedblock section 554, as described below. Furthermore, the cover plate 442b is configured to have one or more indicators to alert the user that the heat exchange cassette is in the correct position for operation. For example, the cover plate may have a slot that operates to depress a switch on the control unit to indicate proper placement, such as a switch in the receiving opening 402 of the exemplary control unit 404 of FIG. 9. Similarly, the cover plate 442b may have slots 620, leading to depressions 622 that received biased detents such a spring loaded bearings on the control unit. When the heat exchange cassette 400b is being positioned within the control unit, the detents will be guided along the slots 620, and once the unit is fully inserted the detents will cam into the depressions 622 with an audible click to inform the user that placement is complete, As one of skill in the art will understand, a more secure positive locking arrangement may be provided, although as will be described below, pressurization of the external heat exchanger 440b serves to hold the heat exchange cassette 400b tightly within the re-usable control unit.

c. Fluid Pathway Through Second Heat Exchange Cassette During Automatic Prime

Prior to a detailed description of the sections of the bulkhead assembly 430b, fluid flow through the heat exchange cassette 400b will be generally explained. When the external fluid source has been attached to the feedblock 554, the system is initially filled with fluid and purged of air before insertion into a patient. This process is called priming. The priming is done automatically by the cassette in conjunction with the control unit depicted in FIG. 9. The control unit initially activates a priming push rod 420 that depresses a flexible membrane 672 on the cover plate above the valve actuating rod 680. This positions the valve in the feedblock to the "prime" position (FIG. 14E) so that fluid from the fluid source enters a fluid fill reservoir 682a, and is directed toward the pump through pump feed line 640. The feed line from the reservoir is closed and fluid enters from the fluid bag, to the pump, thence through the pressure regulating chamber, the catheter, back into the heat exchange unit, through the serpentine path, and into the reservoir. As the reservoir fills, the air that is displaced is expelled through the hydrophilic valves. Once the reservoir is full, the fluid level detectors signal the control unit that the reservoir is full, and the prime valve is deactivated, so that pus rod 420 withdraws, flexible membrane 672 relaxes, and the valve actuating rod, 680, which is biased by spring 678 to the upward position, returns to the "run" position. In this position, the priming valve is positioned in the run position (FIG. 14D) and fluid is pumped in a closed circuit from the reservoir, through the pump, through the pressure regulating chamber, through the catheter, back into the heat exchange unit across the TE cooler through the serpentine path, and into the reservoir.

Figure 14D:
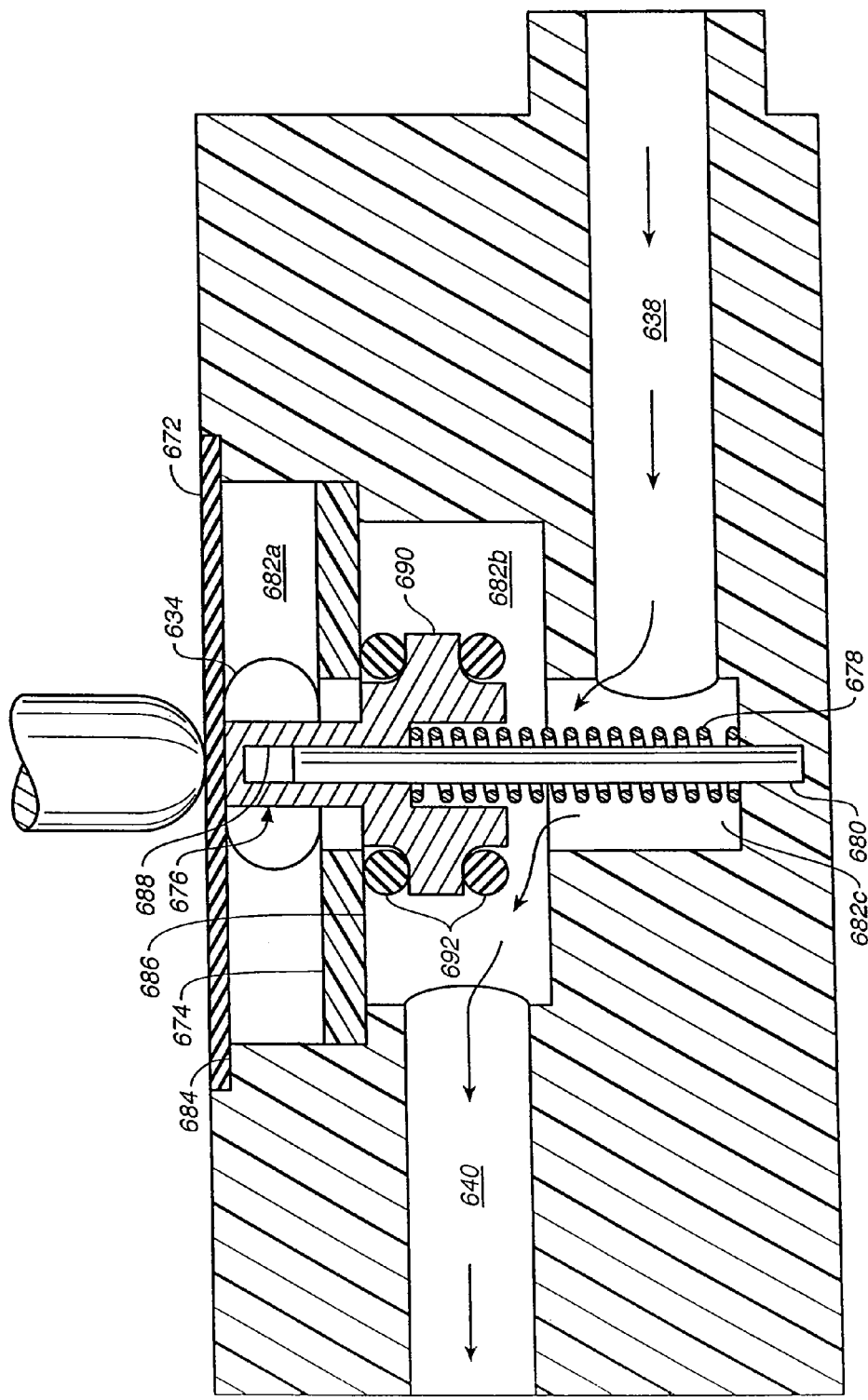
FIG. 14D is a cross-sectional view of the automatic priming valve of the feedblock section of FIG. 14A, with the valve in a "run" orientation.
Figure 14E:
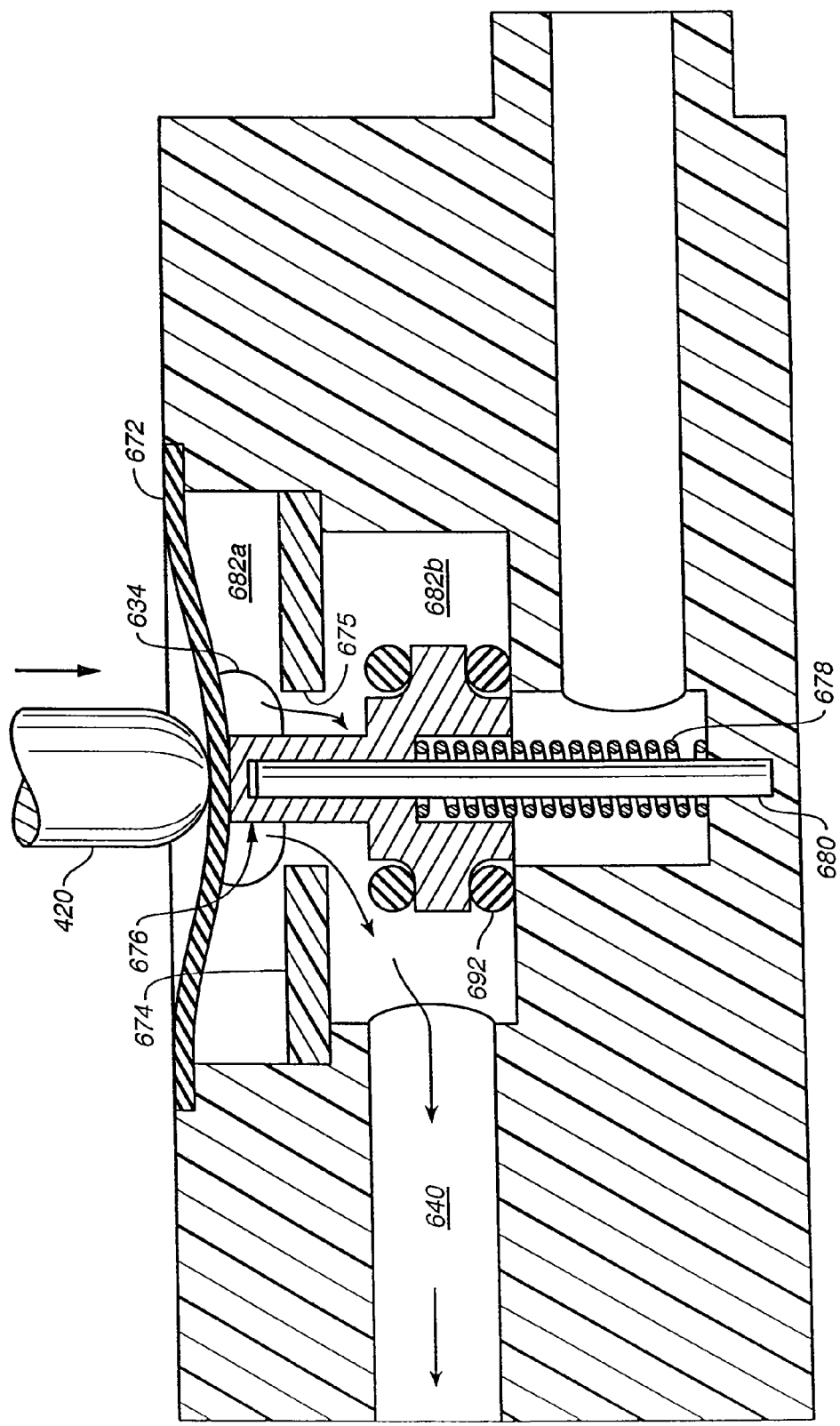
FIG. 14E is a cross-sectional view of the automatic priming valve of the feedblock section of FIG. 14A, with the valve in a "prime" orientation.

To better explain this priming sequence, a number of fluid flow arrows are indicated in FIGS. 13B, 14D and 14E. An external fluid source 630 attaches to a fill port 632 leading to a fill channel 634 in communication with a central chamber 636 of the feedblock section 554 (also see FIG. 14A). The fluid outlet collar 560 of the reservoir section 550 directs fluid to the central chamber 636 via an internal channel 638 in the feedblock section. A further internal channel 640 (FIG. 14A) of the feedblock section 554 provides an outlet from the central chamber 636 leading to the first outlet conduit 572 defined within the first outlet collar 570, and, ultimately, to the pump section 552.

Initially the system is primed as described in the next section. This fills the reservoir, the catheter, and the external heat exchanger with fluid and expels the air in the system. The system is then in the RUN condition, whereby fluid is pumped in a closed circuit in approximately the following pathway, seen best with reference to FIGS. 13B and 13C. The pump section 552 includes a rotary-type pump head 642 that propels fluid through an outlet channel 644 past a pressure regulating chamber 646 in the feedblock section 554 via the inlet conduit 568 within the inlet collar 566. The pressure regulating chamber 646 has an outlet channel 648 and outlet port 650 to which a catheter inflow line 652 (FIG. 13B) couples. The fluid is pumped through the heat exchange catheter from the outlet channel. After passing through the heat exchange catheter, fluid returns through an outflow line 654 that couples to an inlet port 656 (FIGS. 13C and 14A). The return heat exchange fluid then passes through a relay channel 658 and passes out of the feedblock section 554 through the second outlet conduit 576 within the second outlet collar 574. Fluid then passes through a flow through channel 660 within the pump section 552 leading to a bulkhead outlet 662, as also seen in FIG. 13A.

The bulkhead outlet 662 leads to one or more internal flow channels provided within the external heat exchanger 440b. As with the earlier-described embodiment, the heat exchanger 440b may be any combination of one or more structural and compliant members such that the overall configuration is adapted to mate with the opening provided in the control unit 404a. For instance, the heat exchanger 440b may be constructed as seen and described with respect to the cross sections of FIGS. 11A and 11B. Namely, the heat exchanger 440b may include a rigid back plate 500 and a layer 502 of flexible, thermally conductive material sealed to the back plate 500 in a pattern which forms a serpentine flow channel 504 therebetween. The aforementioned flow fittings 508 and 512 seen in FIGS. 12A and 12B are also desirably used to facilitate inflow and outflow from the serpentine flow channel 504.

After passing through the flow channel 504 within the heat exchanger 440b, fluid enters the reservoir cavity 584 through the bulkhead inlet orifice 586. And finally, from the reservoir section 550, fluid passes through the outlet collar 560 back into the central chamber 636 of the feedblock section 554.

Alternatively, the system of the present invention can be passively primed, and the fluid level maintained without resort to a switching valve as described above. That is, a fluid supply bag may be attached so as to drain by gravity to prime the system. At the same time there is no backflow valve and the bag accepts excess fluid if, for example, the fluid expands when heated. If the heat exchange balloon leaks and the circuit starts to empty, the bag will continue to fill the system until The bag is empty, then the reservoir level will begin to drop. When it drops to a predetermined low level, a fluid level detector will sense the low level, sound an alarm and shut the flow off. A small fluid bag (e.g., 250 cc's maximum) is desirable so that if there is a leak a minimum amount of heat exchange fluid such as saline will be pumped into the patient. Such a small volume of saline is not considered a medical risk to the patient.

d. Exemplary Feedblock Section

FIGS. 14A-14G illustrate the component parts of the exemplary feedblock section 554 that provides one embodiment of a priming valve and a fluid regulator for the heat exchange catheter system of the present invention. As mentioned, the central chamber 636 has a first inlet in fluid communication with an external fluid source 630, a second inlet in fluid communication with the reservoir section 550, and an outlet in fluid communication with the pump section 552. A priming valve 670 mounted within the central chamber 636 regulates flow into the central chamber from either of the first and second inlets, depending on the fluid level within the reservoir section 550. The priming valve 670 includes, from top to bottom in FIG. 14A, a flexible membrane 672, an annular guide disk 674 having a central orifice 675, a valve member 676, a valve spring 678, and a valve stem 680. As seen in FIGS. 14D and 14E, these components are arranged within the central chamber 636, which actually comprises a series of three gradually smaller stepped subchambers 682a, 682b, 682c.

The solid flexible membrane 672 covers the central chamber 636, and more particularly, seats within a counter bore 684 and is fastened therein, such as with adhesive. A push rod, such as the push rod 420 in the receiving opening 402 of the control unit 404 seen in FIG. 9, is positioned to pass through the priming valve aperture 618 in the cover plate 442b and displace the flexible membrane 672 downward which, in turn, displaces the valve member 676 downward, as seen in FIG. 14E. The push rod 420 is desirably not contained in the heat exchange cassette 400b, and may be manually triggered or automatically controlled such as by the valve actuation system 416 of FIG. 9. The push rod 420 may act, for example, by means of the linear actuator 418 displacing the push rod downward upon a signal from the processor of the control unit 404, triggered by fall insertion of the heat exchange cassette 400b into the receiving opening 402 of the control unit 404.

Once the valve member 676 is displaced downward, the aforementioned fill channel 634 (FIG. 13B) brings fluid from the external fluid source 630 to the upper, largest subchamber 682a. The guide disk 674 seats against a shoulder 686 at the bottom of the upper subchamber 682a that defines a transition between the upper subchamber and the middle subchamber 682b. The middle subchamber 682b opens to the outlet channel 640, and also steps to the smaller lower subchamber 682c. The lower subchamber 682c, in turn, receives fluid from the reservoir section 550 via the inlet channel 638. The rigid valve stem 680 is fixedly position within a cavity in the floor of the lower subchamber 682c, and extends upward into the upper subchamber 682a. The valve member 676 includes an internal cavity 688 that receives the upper end of the valve stem 680 so as to permit relative linear movement therebetween. The valve spring 678 surrounds the valve stem 680 and is placed into compression between the valve member 676 and floor of the lower subchamber 682c.

The valve member 676 has a lower annular flange 690 extending outward from concave shoulders that receive and seat a pair of O-rings 692. The valve member 676 translates linearly along the valve stem 680 such that the O-rings 692 alternately contact the underside of the guide disk 674 (FIG. 14D), and the floor of the middle subchamber 682b (FIG. 14E). The spring 678 normally biases the valve member 676 upward along the valve stem 680 such that the upper O-ring 692 seals against the underside of the guide disk 674. In this default position, seen in FIG. 14D, fluid flows from the reservoir section through the inlet channel 638, lower subchamber 682c, middle subchamber 682b, and through the outlet channel 642 toward the pump head 552. Alternatively, during priming of the system, the push rod 420 is displaced downward, as seen in FIG. 14E, displacing the valve member 676 downward such that the lower O-ring 692 contacts and seals against the floor of the middle subchamber 682b. In this mode of operation, fluid flows from the fill channel 634 into the upper subchamber 682a, through an annular space between the valve member and the central orifice 675 of the guide disk 674, through the middle subchamber 682b, and through the outlet channel 642 toward the pump head 552.

e. Exemplary Pressure Regulator

A pressure regulator valve to regulate the pump output pressure is desirable. Any pressure regulator that down-regulates pressure may be used in the pressure line between a pump outlet 744 and the outlet port 650 to down-regulate the pressure from the pump to the desired supply pressure for the heat exchange catheter. A pressure regulator in accordance with the present invention may also function to dampen any pressure variations, such as vibrations in the fluid line generated by the pump.

One such pressure regulator is illustrated in the feedblock section 554 of the heat exchange cassette 400b of FIG. 14A. The exemplary pressure regulation system is seen in FIGS. 1413-14C and 14F-14G, and comprises a spring-biased diaphragm that flexes to relieve pressure above a threshold value and ensure that heat transfer fluid is provided to the catheter at a relatively constant pressure. For clarity of illustration, FIG. 14B is simplified by removing the priming valve described previously with respect to FIGS. 13B and 13C from the drawing, although in the actual embodiment, the feedblock section contains both elements.

With reference to FIG. 14B, the pump outlet 744 fluidly connects to the inlet of the pressure regulating chamber 646. Fluid pressure at the pump outlet may vary somewhat depending on wear and fluid temperature, and is generally higher than the desired supply pressure for the heat exchange catheter. For example, a catheter supply pressure of about 40 psi may be desired, while the pump outlet pressure may be, for example, 45-54 psi. Therefore, the fluid pressure must be down-regulated before being directed to the catheter. As described in detail below, the present invention provides an apparatus and method of down regulating the pressure by directing the fluid flow through a narrow throttle that automatically adjusts to create a pressure drop of precisely the correct amount.

As mentioned previously with respect to FIG. 13E, a portion of the pressure regulator resides within the reservoir chamber 684 and includes the pressure regulator shaft 598 mounted for linear adjustment within the flange 600, and a reference spring 604 biased between the shaft and the diaphragm 606. As seen in FIGS. 14A and 14B, a push rod 700 attaches to the diaphragm 606 on the feedblock side, and extends through a throttle chamber 702 into the pressure regulating chamber 646. The pressure regulating chamber 646 is in fluid communication with a fluid channel 704 that is in turn in communication with the pump outlet 744. A pressure regulating disk 706 is fixed within the fluid channel 704 and, as best seen in FIGS. 14C and 14F, and has a generally annular outer disk 708, an annular axially-extending lip 709 sized about half the diameter of the disk, and a plurality of radial fingers 710 extending inward from the disk to define a cloverleaf opening 712 therein. The fingers 710 extend radially inward into proximity with the rod 700 so as to act as a centering guide for the rod.

The rod 700 contacts or is attached to the center of a throttle plate 714, having a generally square configuration with rounded corners, as seen in FIGS. 14A and 14G. Arcuate gaps 716 are thus defined between the throttle plate 714 and the cylindrical fluid channel 704. The diaphragm 606, rod 700, and throttle plate 714 are free to axially slide to an extent within the surrounding channels formed in the feedblock section 554. The throttle plate 714, if in contact with the pressure regulating disk, would form a seal against the generally annular lip 709, although in actual function, the throttle plate does not come to rest against the annular lip. Instead it is the passage of the fluid through the small gap existing between the throttle plate, around the annular lip 709, and into the cloverleaf opening 712 that creates the pressure drop lowering the fluid pressure from the pressure at the pump outlet to the desired pressure in the chamber 646.

The throttle plate 714 attaches to a cup-shaped extension 718 that receives a relatively weak throttle spring 720. The throttle spring 720 is received on its other end by a hollow spring cap 722 affixed within the fluid channel 704. The spring cap 722 includes an opening along its axis so that fluid may flow from the pump outlet 744 toward the pressure regulating chamber 646.

The diaphragm 606 is biased to the right (toward the regulating chamber 646) in FIG. 14B by a preset amount equal to the pressure within the reservoir 584 (essentially room pressure because the reservoir is open through the aforementioned hydrophobic valves) plus the adjustable pressure of the reference spring 604. Through attachment of the rod 700 to the diaphragm 606, the throttle plate 714 is also biased away from the pressure regulating disk 706. On the other side, the weak throttle spring 720 biases the throttle plate 714 slightly toward the pressure regulating disk, thus keeping the throttle plate snug and oriented.

Fluid from the pump outlet 744 flows through flow channel 704 past the spring cap 722 and through the arcuate gaps 716 around the throttle plate 714. Fluid then flows through the cloverleaf opening 712 in the pressure regulating disk 706 and into the pressure regulating chamber 646, from where it flows through the outflow port 650 leading to the heat exchange catheter. As best seen by the arrows in FIG. 14C, fluid flowing through the small arcuate gaps 716 formed around the throttle plate 714 experiences a pressure drop because of the narrow size of the gaps, and from the tortuous path as it flows around the annular axially-extending lip 709 and through the cloverleaf opening 712. The magnitude of the pressure drop depends on the spacing between the throttle plate 714 and pressure regulating disk 706, and increases significantly when the spacing decreases because of the nearly right angle turn of the fluid from the gaps 716 inward around the lip 709.

The action of the flexing of the preset diaphragm and the axial movement of the throttle plate act to automatically adjust the pressure drop to the desired level so that the pressure in the pressure regulated chamber is constant at the preset pressure. If the pressure from the pump outlet 704 increases, the diaphragm 606 will flex toward the reservoir, and the attached throttle plate 714 will be forced toward the pressure regulating disk. This will narrow the flow openings between the throttle plate 714 and the fixed pressure regulating disk 706, thus increasing the pressure drop across the components. Conversely, if the pump outlet pressure decreases, the diaphragm 606 will flex outward, moving the push rod away from the reservoir thus causing the throttle plate 714 to move away from the pressure regulating disk 706. This increases the size of the flow openings, thus decreasing the pressure drop across the components. In this way, the pressure regulating system automatically response to variations in pressure at the pump outlet 704 to increase or decrease the pressure drop, and maintain the pressure supplied to the heat exchange catheter at a preset amount, for example 40 psi.

f. Indirect Method of Fluid Pressure Control Using Motor Current

As mentioned above, controlling the pressure and/or flow rate of the heat exchange medium through the heat exchange catheter may be accomplished by regulating the speed of the pump based on the back pressure of the fluid being pumped. Alternatively, conventional flow meters may be provided within the fluid conduits. However, each of these conventional systems presents an additional cost, and may be subject to failure or error. In addition, such monitoring elements desirably would be designed not to contact fluid directly so as to avoid potentially contaminating the fluid. Non-contact flow and pressure sensors typically involve infrared or ultrasonic devices, which, along with the associated hardware to interpret the measurements, can be expensive and subject to failure in use. Consequently, it may be desirable to eliminate the pressure regulator valve, pressure regulator chamber and sensing chamber from the cassette design. In that instance, another means of insuring constant pressure and providing for smooth fluid flow can be incorporated into the cassette design.

Although the present invention encompasses conventional means for controlling the flow rate or pressure of the heat exchange medium, a preferred means is to control the current flow through the pump drive motor. The torque developed by an electric motor is directly proportional to the current supplied to that electric motor. Where, as in the pump described below, friction within the pump is negligible so that the torque generated by friction does not vary significantly with pump speed, the fluid pressure developed by a rotating pump vane such as that described below is directly proportional to torque supplied by the electric motor operating the pump. (Another way of describing the pressure developed by the pump is back pressure developed by the system.) Therefore by controlling the current supplied to the electric motor at a constant amount regardless of the speed (rpm) developed by the motor, the pressure output of the pump would be relatively constant. This pressure regulation to a constant current is achieved with a simple amplification feedback which is well known to those in the art and will not be described in greater detail here.

Suffice it to say, with reference to the embodiment of FIGS. 5-8, the pump drive mechanism 268 typically comprises an electric motor and a power supply that provides the necessary current to run the motor. Constant current can be attained by directing the voltage from the power supply to an amplifier which adjusts and controls the fluctuating voltage input to provide a constant current output to the motor. With a constant current supplied to the electric motor that runs the pump, the motor provides for constant torque to the pump head in the disposable heat exchange unit/cassette, which ultimately provides for constant pressure supplied to the fluid to the catheter.

Therefore, in one embodiment of the disposable cassette of the invention, the cassette comprises an external heat exchanger having an inlet and an outlet, a first fluid supply line in fluid communication with the heat exchanger inlet, a disposable pump head having a pump inlet in fluid communication with the heat exchanger outlet and having a pump outlet, a second fluid supply line in fluid communication with the pump outlet for receiving fluid pumped out of the pump outlet, and an optional pressure regulator in fluid communication with the pump outlet for regulating the pressure of fluid pumped from the pump head. The pump head is actuated by an electric motor that is controlled by an amplifier controller, where the amplifier controller supplies a constant current to the pump head thereby causing the pump head to supply a relatively constant pressure to the fluid in the second fluid supply line.

Exemplary Pump

The pump section 552 is readily adapted for use with the reservoir section 550 and feedblock section 554 of the heat exchange cassette of FIG. 13A or the reservoir section 450 of the heat exchanger and 400a of FIG. 10A, and is configured to allow for pumping of heat exchange fluid at a constant pressure. In this embodiment of the invention, the pumping mechanism creates rapid flow in a heat exchange fluid supply system for supplying a heat exchange fluid to an intravascular heat exchange catheter, and comprises a cavity having a quasi-cardioid shape, an inlet to the cavity, an outlet from the cavity, a pump head comprising a rotor having a central groove, and a vane slidably mounted in the groove and impinging on the edge of the cavity.

Figure 15A:
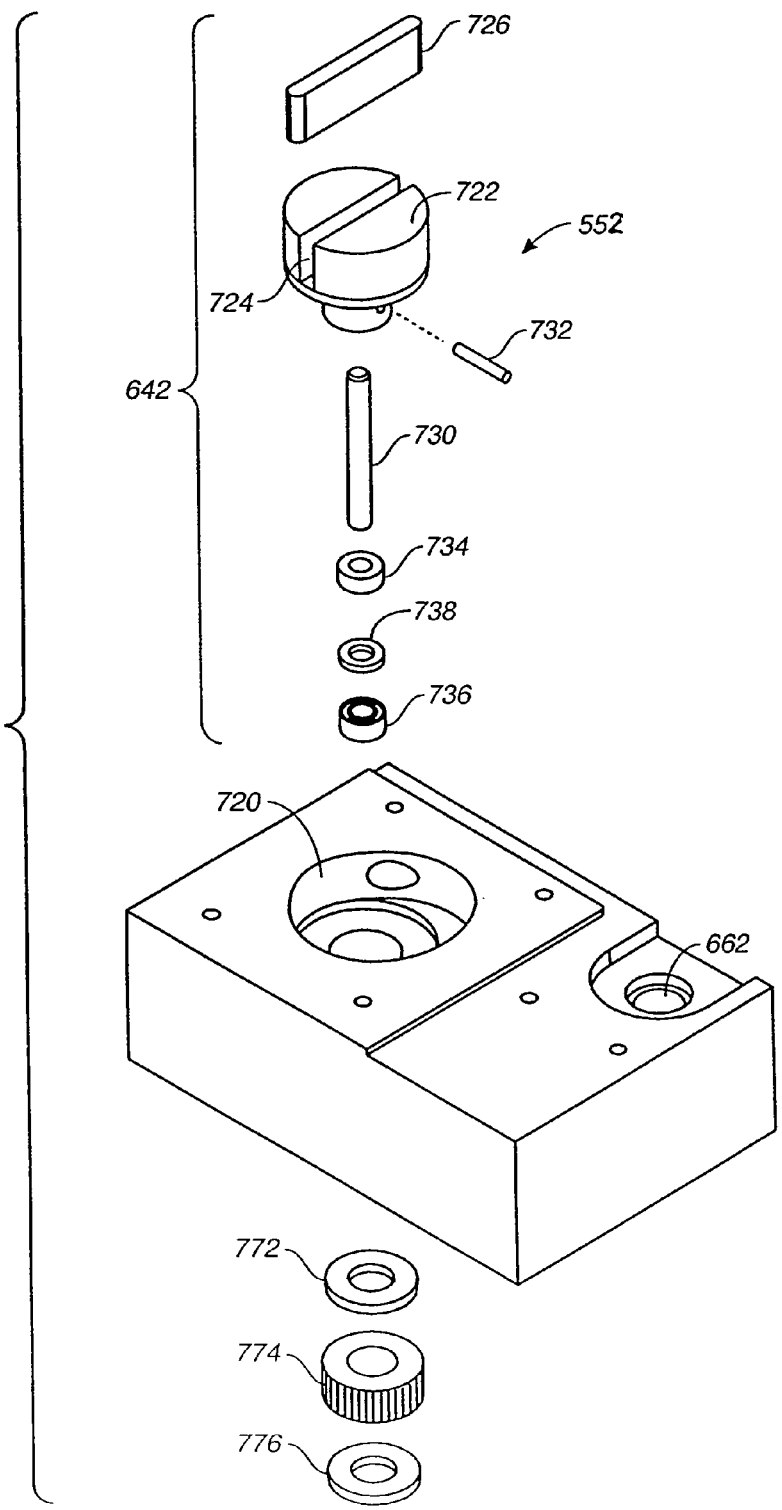
FIG. 15A is a perspective exploded view of a pump section of the bulkhead assembly of FIG. 13B.
Figure 15B:
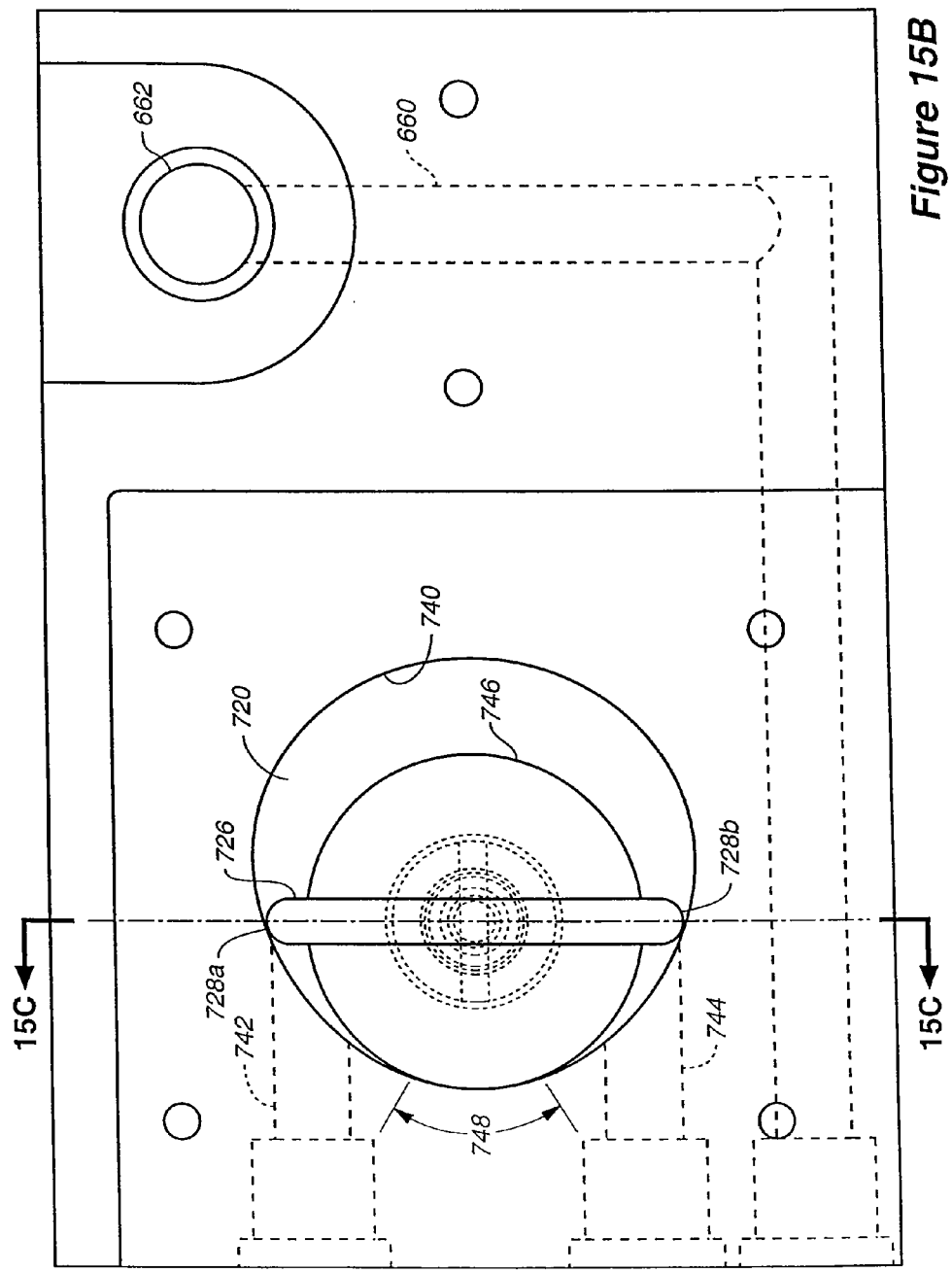
FIG. 15B is a plan view of the pump section of FIG. 15A.
Figure 15C:
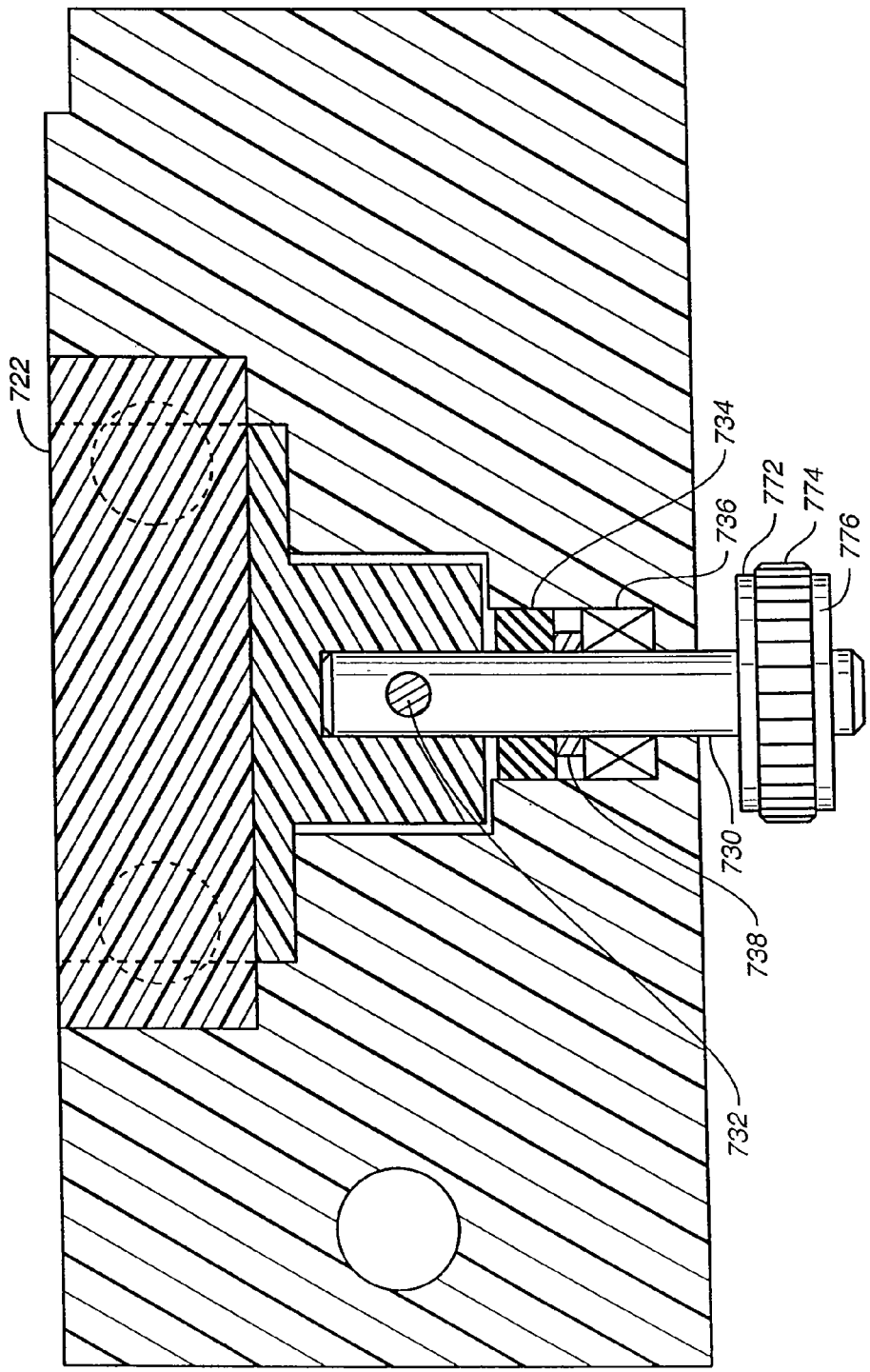
FIG. 15C is a sectional view through the pump section taken along line 15C-15C of FIG. 15B.

An exemplary vane-type pump section 552 is illustrated in FIGS. 15A-15C, where the pump section 550 contains a cavity 720 of quasi-cardioid shape and the pump head 642. The pump head 642 has a rotor 722 which is circular and rotates within the cavity 720, and has a central groove 724 disposed diametrically thereacross. A vane 726 is slidably mounted in the groove and impinges on the edge of the cavity 720. As the rotor 722 rotates around its center, the vane 726 moves freely, sliding back and forth within the groove 724, with the ends 728a, 728b of the vane being continuously in contact with the wall of the cavity 720.

With reference to FIGS. 15A and 15C, the rotor 722 is mounted to rotate with a shaft 730 by means of a pin 732. The shaft 730 rotates within a seal 734 and a bearing 736 separated by an optional spacer 738, provided in a manner known to those of skill in the art of rotating shafts mounted in a fluid-tight arrangement.

With reference to FIG. 15B, a fluid inlet channel 742 leads from the feedblock section 554 and opens into the cavity 720 just beyond the edge of the rotor 722. The aforementioned fluid outlet channel 744 opens into the cavity 720 on the opposite side of the rotor 722 and leads back to the feedblock section 554. As the rotor 722 rotates, the vane 726 is in relatively fluid tight, continuous contact with the cavity wall 740. Fluid enters into the cavity 720 from the inlet channel 742 and is contained in the cavity between the cavity wall 740, the rotor wall 124 and the vane 726. As the rotor 722 rotates the vane 726 also moves. This causes the fluid path to increase in area as it is filled with heat exchange fluid from the inlet channel 742, and then decrease in area as the vane pushes the heat exchange fluid through outlet channel 744. The outer wall 746 of the rotor 722 is in relatively fluid tight contact with the wall 740 of the cavity along arc 748 and therefore fluid cannot travel directly from the inlet channel 742 to the outlet channel 744 of the pump. As the rotor rotates, fluid is pumped from the inlet channel 742 around the quasi-cardioid shaped cavity and pushed by the vane out the outlet channel 744. The configuration of the fluid path can be likened to a "crescent" shape, as can be seen in FIG. 15B.

The pump is designed to rotate within the range of 200-1000 rpm and to function for up to 72 hours. More specifically, the pump is designed to operate for significant periods of time, for example in excess of 72 hours, at fairly high rotational speeds, for example approximately 800 rpm, and to operate on pump fluids at temperatures that vary between approximately 0° C. and 45° C. The choice of materials should be selected to accommodate these needs. For example, the rotor 722 of the pump head is made of a rigid and durable material with adequate lubricity to sustain a long period of close contact with the cavity wall 740 (FIG. 15B) while rotating without undue wear. The rotor 722 may be made of, for example, polyvinylidene fluoride, and the vane 726 may be made of a material such as high density polyethylene.

It is desirable that the heat exchange catheter is supplied with fluid at a relatively constant pressure at the inlet to the catheter, for example about 40-46 psi, but wear and temperature variations may affect the output pressure of the pump. In the embodiment which includes the pressure regulator, the pump is designed to have an output pressure slightly higher than the optimal pressure for the heat exchange catheter, for example 42-48 psi, and the pressure is regulated down to the desirable pressure of 40-46 psi. If the output pressure of the pump varies, a pressure regulator can be incorporated into the disposable heat exchange cassette to ensure that the heat exchange catheter is provided heat transfer fluid at a relatively constant pressure. The pressure regulator can be, for example, a pressure regulator valve as described with reference to FIG. 14B, a pressure damper as seen in FIG. 10D, or a constant current regulation of the pump motor.

The rounded ends 728a, 728b on the vane 726 provide the additional advantage that the point of contact between the vane edges and the cavity wall 740 changes constantly through the rotation of the rotor 722 and thus avoids a single wear point on the ends of the vane. This allows the vane 726 to rub against the wall 740 of the cavity for as long as 72 hours and yet retain a relatively fluid tight contact therebetween. In a preferred embodiment, the vane is designed to fit in the cavity 720 at room temperature with a slight clearance, for example 0.127 mm (0.005 inches). This clearance is one means of accommodating the transient and steady state thermal changes that occur during operation and allows for expansion of the vane due to an increase in temperature during operation. In this manner, at the temperatures that are encountered during normal operation, the vane ends 728a, 728b will maintain adequate contact with the wall 740 of the cavity 720 for pumping.

Figure 16A:
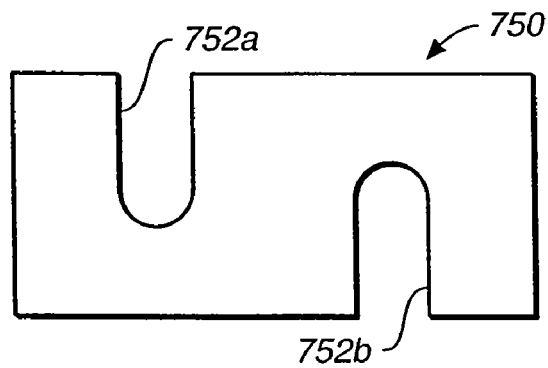
FIGS. 16A-16C are elevational views of alternative embodiments of a pump vane for use in the pump section of FIG. 15A.
Figure 16B:
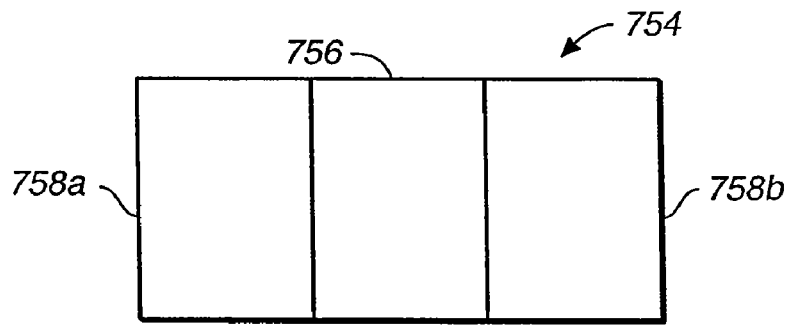
Figure 16C:
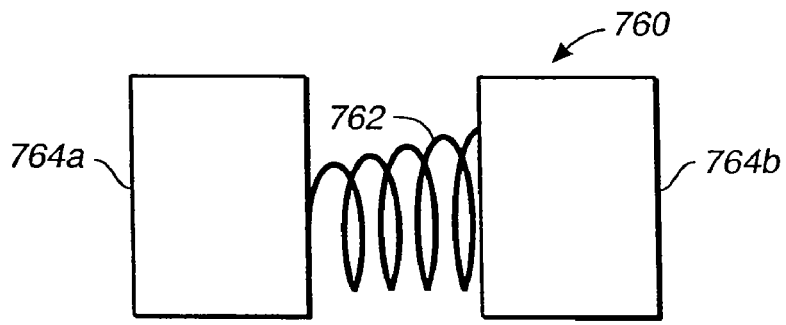

There are numerous other vane designs that also accommodate thermal changes so that the vane remains in continuous contact with the wall of the cavity and is able to move smoothly within the cavity. FIGS. 16A-16C are side views of examples of such designs. In FIG. 16A, a vane 750 is configured with cut-out sections 752a, 752b, which allow for expansion or contraction of the vane during operation. In FIG. 16B, a vane 754 defines a center section 756 made of a compressible material to accommodate expansion or contraction of the end portions 758a, 758b during operation. In FIG. 16C, a vane 760 includes a center spring 762 to bias the end portions 764a, 764b outward during operation to contact the wall of the cavity regardless of the temperature of the vane.

Figure 15D:
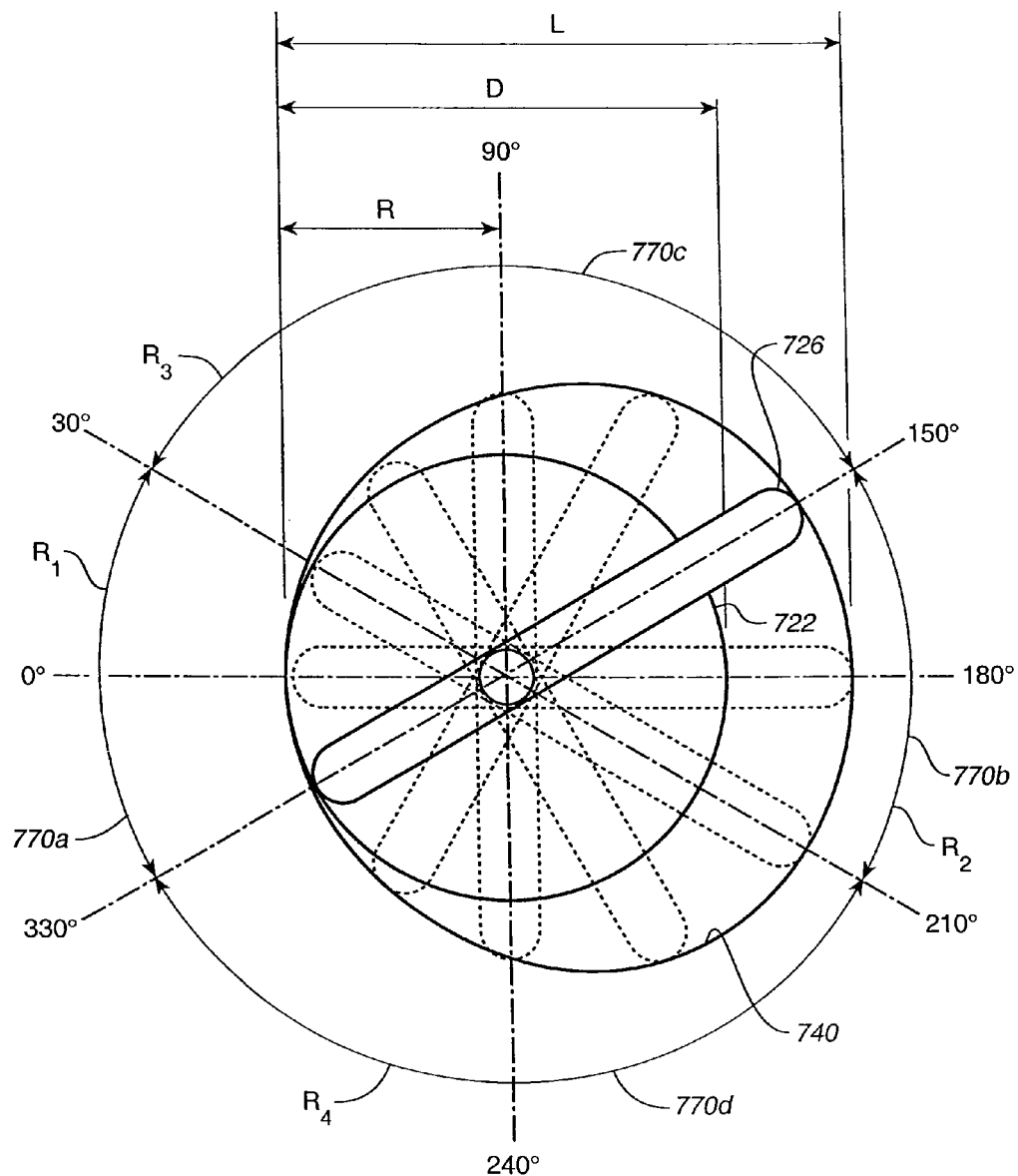
FIG. 15D is a schematic plan view of the geometry of a pump head within the pump section of FIG. 15A.

One significant aspect of the invention relates to the geometry of the quasi-cardioid shaped cavity 720, as seen in FIG. 15D. Recalling FIG. 15B, the cavity wall 740 includes an inlet 742 and an outlet 744 thereto, and is part of the pumping mechanism of the disposable heat exchange cassette 400b. The pump head 642 of the pumping mechanism comprises the rotor 722 having a diameter "D" and the aforementioned diametral groove 724 (FIG. 15A), and the vane 726 having a length "L" and slidably mounted in the groove so as to impinge on the edge of the cavity 740.

As shown in FIG. 15D, the circumference of the cavity 740 can be divided into four arcs 770a, 770b, 770c, 770d, where the radius "R" of each arc has its center at the center of the rotor 722 and is measured to the cavity wall 740. For orientation purpose, the arcs 770a, 770b, 770c, 770d are defined with reference to the center of the rotor 722, with a base line of 0° identified with the point midway between the inlet and the outlet of the cavity, i.e., the line projected from the center of the rotor 722 and the point on the cavity wall that is midway between the inlet channel 742 and the outlet channel 744 (see FIG. 15B). 0-360° angles are measured, in a clockwise fashion from the base line.

Accordingly, the four arcs are defined as follows: (a) a first arc 770a from 330° to 30° and having a radius $R_1$, (b) a second arc 770b from 150° to 210° and having a radius $R_2$, (b) a third arc 770c from 30° to 150° and having a radius $R_3$, and (d) a fourth arc 770d from 210° to 330° and having a radius $R_4$. The four radii are defined as follows:

$$R_1 = D/2$$

$$R_2 = L - (D/2)$$

$$R_3 = (D/2) + \{[(L-D)12] \cdot [\cos(1.50+135)]\}$$

$$R_4 = (D/2) + \{[(L-D)/2] \cdot [\cos(1.50-315)]\}$$

Therefore, arc 770a is circular and thus has a constant radius $R_1$; arc 770b is not circular since its radius $R_3$ changes as the angle of rotation increases from 30° to 150°; arc 770c is also circular and thus also has a constant radius $R_2$; and arc 770d is not circular since its radius $R_4$ changes as the angle of rotation decreases from 210° to 330°. These calculations are somewhat approximate because the vane has a thickness, the end of the vane also has a radius (i.e. is rounded), and the exact contact point between the vane and the wall of the cavity varies slightly with the rotation of the rotor. Since both ends of the vane have the same radius of curvature, this imprecision is equal on each side, and the exact shape of the cardioid cavity can be adjusted to compensate and still maintain contact at all points between the vane and the cavity wall.

Figure 17A:
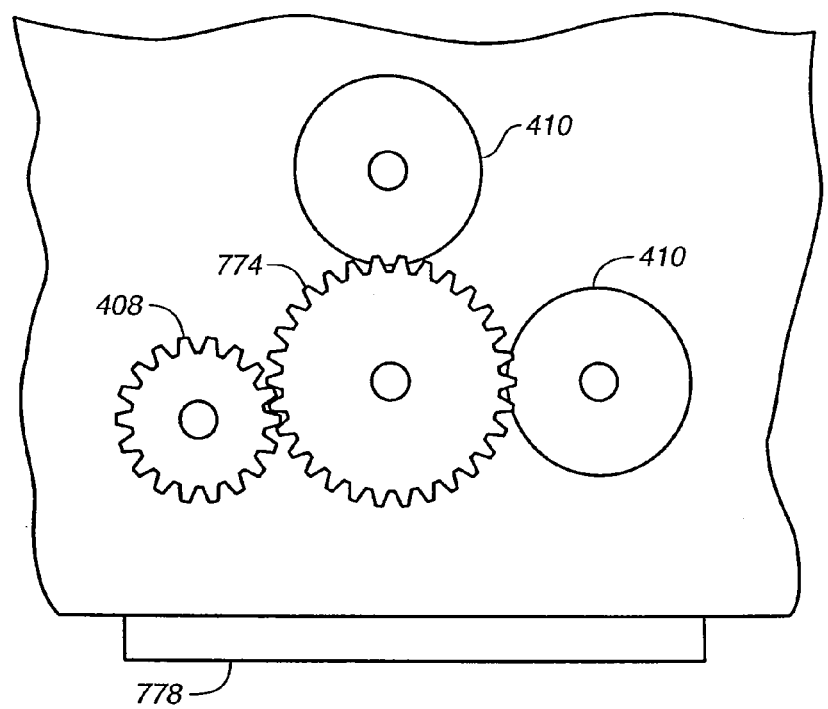
FIGS. 17A-17B are plan and elevational views, respectively, of a pump head driven gear engaged with a drive mechanism of the re-usable control unit.

With reference now to FIG. 15C, the shaft 730 protrudes below the rotor 722 and is fitted with three wheels 772, 774, and 776 which cooperate with the pump drive mechanism housed in the reusable control unit 404 (FIG. 9), which imparts rotational motion to the shaft and thence to the rotor. The top most wheel 772 is a smooth alignment wheel, the middle wheel 774 is a toothed driven wheel, and the bottom most wheel 776 is another smooth alignment wheel. The driven wheel 774 can be constructed, for example, of a plastic material such as nylon, polyurethane or PPS. The alignment wheels 772 and 776 can be constructed, for example, of a polycarbonate material. These three wheels cooperate with a plurality of wheels on the reusable control unit 404, two of which are depicted in FIG. 9 as guide wheels 410. A toothed drive wheel 408 is driven by the pump drive mechanism 406, and is shown in FIGS. 17A and 176, which depict placement of the pump wheels 772, 774, and 776 within the control unit 404. FIG. 17A also shows placement of a gear shield 778, which covers the receiving opening 402 in the control unit 404 (FIG. 9) once the heat exchange cassette 400b is positioned in place.

Figure 17B:
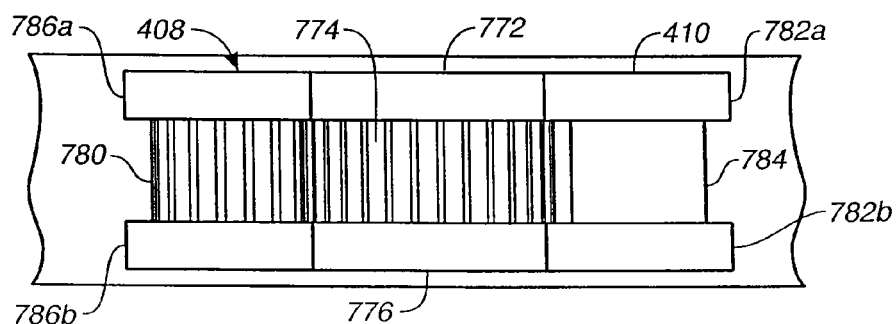

When the heat exchange cassette 400b is inserted into the reusable control unit 404, the toothed driven wheel 774 engages the toothed portion 780 of motor wheel 708. The driven wheel 774 and motor wheel 408 are held engaged by contact between guide wheels 410 and alignment wheels 772, 776. As can be seen in FIG. 17B, the guide wheels 410 have a larger diameter top and bottom sections 782a, 782b, respectively, with a small diameter middle section 784. This allows the top sections 782a to fit snugly against alignment wheel 772 and the bottom sections 782b to fit snugly against alignment wheel 776, while at the same time the middle section 784 will not come in to contact with the toothed drive wheel 774. The guide wheels can be machined as a single spool-shaped unit or the top, middle and bottom sections can be separate pieces that are permanently affixed together. The toothed motor wheel can also be designed to have a slightly larger top section 786a that fits snugly against alignment wheel 772 and/or a slightly larger bottom section 786b that fits snugly against alignment wheel 776. Preferably the motor wheel makes contact with at least one of the smooth alignment wheels.

The positioning of the alignment and guide wheels causes the teeth of motor wheel 408 and driven wheel 774 to mesh at the appropriate distance so that the teeth are not forced tightly together. The diameter of the smooth alignment wheels 772, 776 will be approximately the pitch diameter of the driven wheel 774 to provide proper positioning of the drive teeth. Similarly, the diameter of the top and bottom sections, 786a, 786b, of the motor wheel 408 will be approximately the pitch diameter of the toothed portion 780 of the motor wheel 408. This is advantageous in imparting smooth rotational motion without imparting side forces to the drive shaft, or causing friction between the teeth by virtue of their being jammed together.

The diametral pitch of the driven wheel 774 and the motor wheel 408 are the same and they preferably will have the same diameter. However they may be different diameters, but it is preferable that the gear pitch is the same, for example, a diametral pitch of 48 (48 teeth per inch in diameter) has been found to provide adequate strength with minimal noise during operation. A typical driven wheel 774 will have a pitch diameter of 2.54 cm (1 inch), and the corresponding motor wheel 780 will also have a pitch diameter of about 2.54 cm (1 inch).

Methods for Priming the Heat Exchange Catheter System

Figure 18A:
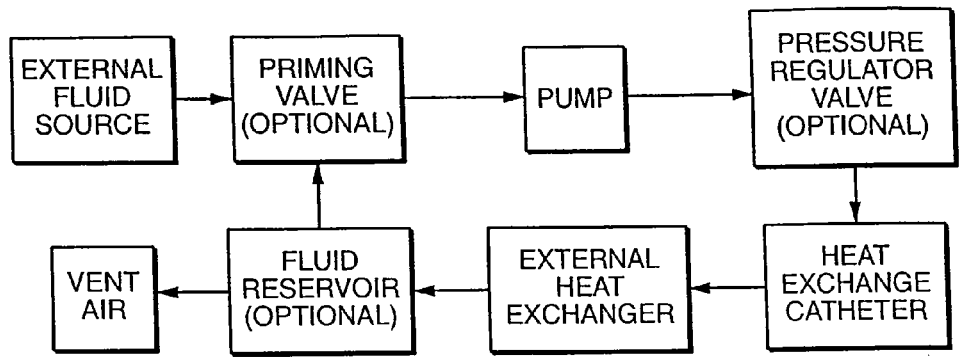
FIGS. 18A-18C are schematic illustrations of the fluid flow using different embodiments of the disposable heat exchange cassette of present invention.
Figure 18B:
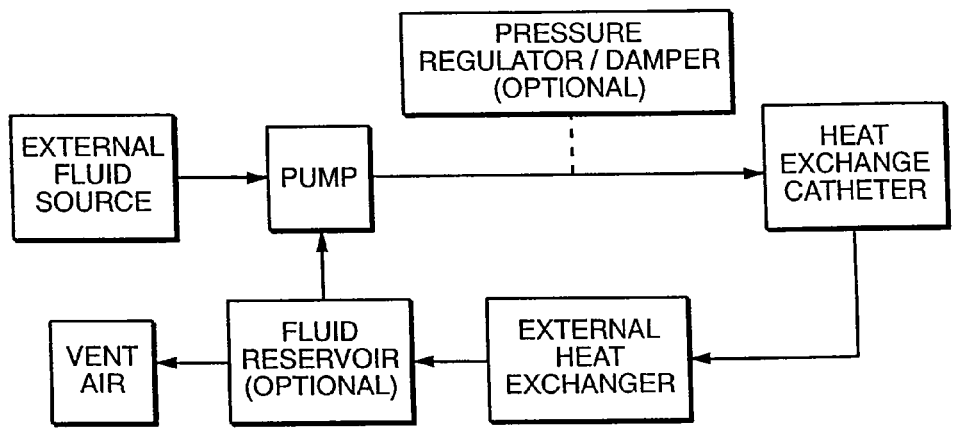
Figure 18C:
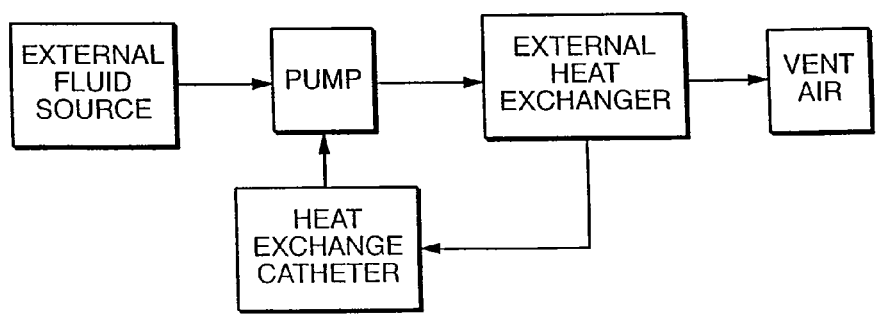

Referring to FIGS. 18A-18C, several methods of supplying heat exchange fluid to an intravascular heat exchange catheter are illustrated by fluid flow pathways, each pathway illustrating a different embodiment of the heat exchange cassette of the invention. In these embodiments, fluid flows from the pump to the heat exchange catheter, returns from the catheter and passes through the external heat exchanger, and then enters a fluid reservoir. From the reservoir, the fluid moves to the pump, and the cycle repeats for the desired duration. An optional pressure regulator can be position in the fluid path moving from the pump to the catheter. Fluid is provided from an external fluid source, which in the embodiment of FIG. 18A enters the priming valve, and in the embodiments of the FIGS. 18B and 18C directly enters the pump head (of course, as indicated in FIG. 10B, the external source of fluid may be connected to the reservoir).

Examples of these methods and the respective fluid pathways are further understood by reference to FIGS. 10A and 13A. In general, the method comprises the steps of:

(a) providing power to operate a pump head;

(b) transferring fluid from an external fluid source to a chamber;

(c) pumping fluid from the chamber into a pump cavity;

(d) pumping fluid from the pump cavity to the catheter;

(e) pumping fluid from the catheter to a external heat exchanger which is positioned in heat transfer relationship with a heater/cooler;

(f) pumping fluid from the external heat exchanger to a heat exchange fluid reservoir;

(g) pumping fluid from the heat exchange fluid reservoir into the pump cavity; and (h) repeating steps (d) through (g) for the duration of operation of the catheter.

The heat exchange cassette of the invention is initially primed, that is, filled with heat exchange fluid from an external source and excess air removed. This priming of the system of the invention can be accomplished in numerous ways. One embodiment of the invention utilizes a "valved-priming" mechanism, and is illustrated by the embodiment of FIGS. 13A-14E. This valved-priming mechanism involves a priming sequence having a valve or the like controlling temporary fluid input from an external fluid source, and once the system is primed, the valve prevents further fluid input from the external source and fluid thereafter circulates within a closed circuit including the heat exchange cassette 400b and the attached in-dwelling catheter. In the embodiment of FIGS. 13A-14E, the valved priming mechanism 670 is contained within a discrete unit, namely the feedblock section 554. It is understood however, that the valved-priming mechanism can be located in another portion of the bulkhead 430b, for example as part of the pump section 552 or reservoir section 550, and still serve the same function.

The invention also encompasses a method for automatically commencing and ceasing the priming of a heat exchange fluid supply system for supplying a heat exchange fluid from an external fluid source to an intravascular heat exchange catheter, using the means described above. This method comprises the steps of:

(a) first providing power to operate the pump, wherein the reservoir is not filled to capacity and the valve is in its first position and the pump operates to pump fluid:

a. from the external fluid source through the fluid providing line into the fill port of the chamber and out of the fluid outlet into the pump cavity b. from the pump cavity to the fluid return line to the catheter;

c. from the catheter through the fluid supply line to the external heat exchanger inlet orifice;

d. from the external heat exchanger outlet orifice to the heat exchange fluid reservoir; and e. into the heat exchange fluid reservoir to fill the reservoir;

(b) then filling the reservoir to capacity; at which point (c) the optical fluid level detector operates to move the valve to its second position and the pump operates to pump fluid from the heat exchange fluid reservoir to the fluid inlet of the chamber and out of the fluid outlet into the pump cavity.

When the disposable heat exchange cassette 400b of the invention is first put into operation, the unit is initially filled with heat exchange fluid from an external fluid source such as an IV bag of saline attached to the fill port 632 leading to the fill channel 634. In addition, the linear actuator 418 of the valve actuation system 416 is activated, to place the priming valve 670 in its first position (FIG. 14E) with the valve member 676 depressed sufficiently to allow fluid to flow from the IV bag into the valve chamber 636. More specifically, during a priming operation, the push rod 420 in the receiving opening 402 of the control unit 404 seen in FIG. 9, passes through the priming valve aperture 618 in the cover plate 442b (FIG. 13A) and displaces the flexible membrane 672 downward which, in turn, displaces the valve member 676 downward, as seen in FIG. 14E. The lower O-ring 692 on the valve member 676 thus contacts and seals against the floor of the middle subchamber 682b, permitting fluid to flow from the fill channel 634 into the upper subchamber 682a, through the middle subchamber 682b, and through the outlet channel 642 toward the pump head 552. In this manner, heat exchange fluid from external fluid source 630 (FIG. 13B) enters the feedblock section 554, and then flows into the pump section 552. From the pump section 552, the fluid is pumped out through pressure regulating chamber 646, the outlet channel 648 and outlet port 650, and to the catheter inflow line 652 leading to the heat exchange catheter. Fluid is thereafter circulated through the catheter, back through the catheter inflow line 654 that couples to an inlet port 656 of the feedblock section 554, through the flow through channel 660 within the pump section 552 leading to a bulkhead outlet 662. Fluid enters and passes through the external heat exchanger 440b and back into the reservoir section 550. As the fluid is pumped into the reservoir section 550, air displaced by the fluid escapes through the hydrophobic vents 588. This generally continues until the system is full of heat exchange fluid and excess air has been vented out of the system. At this point in the process, the valve 670 is closed from the external fluid source 630 (by, e.g., automatic release of the push rod 420) and the fluid supply circuit between the catheter and the heat exchange cassette 400b is closed.

The reservoir section is provided with a means to detect when the fluid reservoir is full, as described below, whereby signals are provided to the reusable control unit that represent the level of the heat exchange fluid in the reservoir. Using these data, the reusable control unit adjusts the linear actuator 416 so that the position of the valve 670 changes and the fluid flow path is altered. Thus when the fluid level in the reservoir section 550 rises to a sufficient level, a signal is sent to the reusable control unit to deactivate the linear actuator 416 so that it moves to a released position, thus withdrawing the push rod 420, resulting in the valve member 676 being biased back to its second position (FIG. 14D). In this second position, fluid from the now full reservoir is directed through the feed-block section 554 to the pump section 552, while fluid flow from the external fluid source is diminished or ceases entirely.

In a preferred embodiment the pump would continue to run for a period of time after the level sensor indicated that the system was full to ensure that any air bubbles in the catheter or the external heat exchanger or the bulkhead would be expelled into the reservoir section 550 where they could vent to the atmosphere. Since the fluid is being drawn from the bottom of the reservoir through reservoir outlet channel 561 (FIG. 13E), and air moves up towards the top of the reservoir where the hydrophobic vents 588 are located, this acts to purge air from the system. Therefore, it is important to realize that the priming valve 670 may also have a third position that is an intermediate position from its first and second positions described above. In this manner, heat exchange fluid may enter the central chamber 636 from either the reservoir or the external fluid source, or both simultaneously if the priming valve 670 is opened to this intermediate position. So, for example, in an embodiment of the intention that utilizes the pump in a first, intermediate and then second position, fluid would enter the pump solely from the external fluid source (first position, FIG. 14E), then fluid would enter the pump in part from the external fluid source and in part from the reservoir section 550 (intermediate position) and finally fluid would enter the pump solely from the reservoir section 550 (second position, FIG. 14D).

It should be noted that priming of the system occurs prior to the insertion of the heat exchange catheter into the patient, with the heat exchange balloon outside the body. Indeed, the heat exchange balloon is desirably restrained within a protective tubular sheath, or is otherwise radially constrained, to prevent inflation thereof during priming. Once priming is complete, the pump motor is halted, the protective sheath is removed, and the catheter is inserted to the desired location within the patient. The sheath thus ensures a radially compact profile of the catheter during priming of the system and subsequent intravascular insertion, which prevents injury and facilitates the insertion so as to speed up the procedure.

Referring to the embodiment of FIGS. 13-15 and the flow diagram of FIG. 18A, a method for supplying heat exchange fluid to an intravascular heat exchange catheter comprises the steps of:

(a) transferring fluid from an external fluid source 630 to a fluid reservoir 550;

(b) providing power to operate a pump head 642;

(c) venting air from the fluid reservoir section 550 as the air is displaced by the fluid from the external fluid source;

(d) pumping fluid through a circuit that includes the fluid reservoir section 550 through a pump cavity 720, to a heat exchange catheter, then to an external heat exchanger 440b which is positioned in heat transfer relationship with a heater/cooler, and hence the fluid, and air displaced by the circulating fluid, flow from the external heat exchanger 440b to the fluid reservoir 550;

(e) venting the air displaced by the circulating heat exchange fluid from the fluid reservoir section 550;

(f) repeating steps (a) through (e) for the duration of operation of the catheter.

Preferably a step for measuring the fluid level in the heat exchange fluid reservoir is included to insure that the reservoir remains full. Such a step can also comprise using an optical fluid level detector to determine the fluid level, where step (h) begins when the reservoir is filled to capacity and step (b) ceases when step (h) begins. The method for supplying heat exchange fluid to a catheter for the embodiment of FIG. 10A uses a passive-priming mechanism, while the method for the embodiment of FIG. 13A uses a unique valved-priming mechanism, described in detail above. In the priming mechanism shown in FIG. 10A, the fluid level measuring step may also comprise using an optical fluid level detector to determine the fluid level, where step (g) begins when the reservoir is filled to capacity and step (b) ceases when step (g) begins.

More particularly, the embodiment of FIGS. 10A-10D provides the mechanism for passively priming the system with heat exchange fluid from an external source 454. The external fluid source 454 is generally hung or placed at a location above the reservoir 450, and is connected by a fluid providing line 456 to the reservoir. The reservoir 450 has a fill port 476 connected to the fluid providing line 456, and thus fluid flows into the reservoir 450 which communicates with the pump section 452, thus priming the pump head 490. Initially, with the catheter out of the patient's body and sheathed, the pump is operated to draw heat transfer fluid from the external fluid supply and circulate it through the system. The air that is in the system is vented through the hydrophobic air vents. When the pressure in the system is equal to the head pressure from the external fluid source (this will happen at a level which depends on the pump pressure and the height of the external fluid source above the reservoir) the system will essentially be in equilibrium and will cease drawing fluid from the external source. At this point the catheter and heat exchange cassette system will be considered to be primed. The heat exchange catheter will generally thereafter be inserted into the patient, and as the system is operated, any fluid required to be added to the system to maintain the pressure equilibrium mentioned above will be drawn from the external source which is in fluid communication with the reservoir through fluid providing line. Likewise, any buildup of pressure in the system due, for example to the heating and expanding of the system, will be relieved by fluid flowing back into the external fluid supply source 454. Because of the ability of the system to react to minor expansions and contractions of fluid supply, there is no need to monitor the high level of fluid, and only redundant sensors of the low level need be incorporated into the heat exchange cassette. This has the advantage of automatic maintaining a relatively uniform fluid level without the need for sensors and the like.

Safety Systems

The reservoir section can be provided with a means to monitor the amount of heat exchange fluid that is in the system, more specifically an optical means for detecting the level of fluid contained within the fluid reservoir. Since the heat exchange fluid is a biocompatible fluid and the volume of the external source is only about 250 ml, it is not expected that fluid leakage into the patient will be problematic. It would be undesirable, however, to have the fluid level fall so low that air is pumped into a patient. Therefore the heat exchange fluid supply system of the invention is designed to detect the level of the fluid in the system so that a warning or other measure can be instituted if the system becomes unacceptably low. In a preferred embodiment, two prisms in the bulkhead reservoirs, each having a corresponding beam source and beam, are utilized. Each prism will have a corresponding beam source and sensor mounted on the reusable control unit at a location adjacent to the prism.

For example, FIG. 9 illustrates placement of an optical beam source 412 and optical beam sensor 414 for the first prism 590a in the bulkhead design of FIGS. 13A-13E. As seen in FIG. 13E, the transparent window 591 configured in the end of the reservoir container 580 allows for optical observation of the fluid level in the reservoir cavity 584. An adjacent beam source and sensor would also be provided for the second prism 590b, if present.

For the bulkhead design of FIG. 10A, the beam source(s) and sensor(s) would be positioned on the control unit 404 at a location underneath the first and second prisms 486a, 486b. For example, the fluid level measurement sensor module 276 mounted on the underside of the lower guide assembly 266 in FIG. 6B may include optical transmitters/sensors that are placed in registry with the transparent window 316 so as to interact with the heat exchange cassette and provide an indication of fluid level within the unit. The prisms have a diffraction surface and may be machined separately using a material such as polycarbonate and then affixed within the reservoir section, or they may be machined as part of the section. Again, although only one prism is needed for the fluid level detection method to function, it may be desirable to include a second redundant prism described below.

The second prism/source/sensor is redundant and functions to monitor the same fluid level as the first prism but operates as a safety mechanism in the even the first prism/source/sensor fails to function properly. Alternatively, one of the prisms may also have a "high level" sensing system that can be used to signal the control unit when the fluid in the reservoir reaches a certain high level. This is useful, for example, when the valved-priming system is used and detection of a high or full level is needed to determine when to activate the valve to stop the priming sequence. If desired, both high level and low level sensors can be employed on each prism. The sensors will generate a signal indicating that either there is or is not fluid at the level of the optical beam. If the optical beam source and sensor are positioned or the optical beam is directed near the top of the tank, the indication that the fluid has reached that level will trigger the appropriate response from the control system, for example to terminate a fill sequence. On the other hand, if the sensor is positioned or optical beam directed to sense the fluid level on the bottom of the tank, then the fluid level detector is configured to detect a low fluid level and can generates a signal representing such low level. The heat exchange cassette can then be configured to respond to this signal indicative of a low level of fluid in the reservoir. For example, the pump head can be designed to be responsive to this signal such that the pump head stops pumping when a low fluid level is detected, so that air will not be pumped into the heat exchange catheter. In addition, an alarm may sound and an alarm display, such as the display 200 of FIG. 5C, may be activated to alert the operator to the low fluid level condition.

In a preferred embodiment of the present invention, several levels of safety redundancy are provided to prevent failure of the system, and potential injury to the patient. First, two microprocessors may be provided and constantly monitored for agreement. If one fails, the system alarms and shuts. Secondly, two or more patient sensors may be provided and monitored for agreement. They are sampled frequently by the controller and if the values do not agree, as with the microprocessor, the system alarms and shuts down. Likewise, two or more fluid level sensors for the heat exchange circulation path desirably agree for redundancy. Still further, two or more temperature sensors for the heat exchange medium could be provided and monitored for agreement. In short, various redundant subsystems of the overall system ensure proper operation and the feedback therefrom is used to shut off the system if necessary.

In a preferred embodiment of the invention, the reservoir section is provided with a means to detect when the fluid reservoir is too low. Typically, an optical beam source would begin operation after the reservoir fills with fluid. In operation, the optical beam source produces an optical beam that is directed into the prism from the bottom and is internally reflected one or more times within the prism at its surface interface with the fluid and back to the optical beam sensor. As long as fluid is in the reservoir, the sensor will observe a reflected light beam and the pump will continue to operate, moving fluid through the heat exchange cassette and catheter. However, if the fluid level drops below the upper reflective surfaces of the prism, thus changing the reflective index at that internal surface, the sensor then will not observe a reflected light beam. When no such reflected beam is received, the system sounds an alarm and ceases to pump.

In the embodiment of the invention that involves a valved-priming sequence, the optical beam source is turned on to produce an optical beam that is directed towards the top of the prism. The prism is configured to reflect the beam if the top surface is covered with the heat exchange fluid. A sensor is located below the prism where the light beam will be reflected from the top surface of the prism. As long as the sensor below does observes a reflected light beam, the fill or priming operation of the heat exchange cassette continues to run. As the fluid level rises, at some point it reaches a level such that the top surface of the prism is covered with the fluid, and the optical beam reflected back to the sensor. When the sensor observes a reflected light beam, it generates a signal to the controller to cease the priming operation of the heat exchange cassette, for example by activating a motor to withdraw the push rod 420. Thereafter, the fluid level detector operates to detect a low level for safety purposes, that is once the presence of a signal indicates that the priming has been completed, the sensor continues to generate a signal indicating that the fluid level is above the prism. When the fluid level falls below the reflecting surface of the prism, the sensor sends a signal to the controller that will then act to trigger an alarm and shut down the fluid flow. In this way the system may automatically prime, subsequently be automatically signaled to run, and then automatically shut down if the fluid level falls.

Additional safety systems that are contemplated by the invention include bubble detectors at various locations on the conduits to detect any bubble that may be pumped into the fluid system and temperature monitors that may signal if a portion of the system, or the fluid, is at a temperature that is unacceptably high or low. A detector to indicate whether the fluid sensor optical beam sources are operational may be supplied, for example by placing a detector located to detect the optical beam initially when the system is turned on but there is insufficient fluid in the reservoir to cause the beam to diffract back to the detector. The control unit depicted in FIGS. 1, 2 and 5 provide for multiple patient temperature sensors. A warning may sound, and the system may shut down, if the temperature signal from the two different sensors are dramatically different, indicating that one of the sensors, perhaps the one driving the control of the system, is misplaced, is not functioning, has fallen out or the like. Other similar safety and warning systems are contemplated within the scope of the system of the invention.

It should also be understood, in accordance with the present invention, that the controller processor may be configured to simultaneously respond to multiple sensors, or to activate or de-activate various components such as several heat exchangers. In this way, for example, a controller might heat blood that is subsequently circulated to the core body in response to a sensed core body temperature that is below a target temperature for the core, and simultaneously activate a second heat exchanger to cool blood that is directed to the brain region in response to a sensed brain temperature that is above a target temperature for the brain. It may be that the sensed body temperature is at the target temperature and thus the heat exchanger that is in contact with blood circulating to the body core may be turned off by the controller, while at the same time the controller continues to activate the second heat exchanger to cool blood that is directed to the brain region. Any of the many control schemes that may be anticipated by an operator and programmed into the control unit are contemplated by this invention.

A further advantage of the system of the present invention is that all of the portions of the system that are in contact with the patient are disposable, but substantial and relatively expensive portions of the system are reusable. Thus, the catheter, the flow path for sterile heat exchange fluid, the sterile heat exchange fluid itself, and the pump head are all disposable. Even if a rupture in the heat exchange balloon permits the heat exchange fluid channels and thus the pump head to come in contact with a patient's blood, no cross-contamination will occur between patients because all those elements are disposable. The pump driver, the electronic control mechanisms, the thermoelectric cooler, and the manual input unit, however, are all reusable for economy and convenience. Desirably, as illustrated, all of these re-usable components are housed within a single control unit. Likewise, the various sensors distributed around body and along the catheter may be disposable, but the controller processor to which they attach is re-usable without the need for sterilization.

It will also be appreciated by those of skill in the art that the system described herein may be employed using numerous substitutions, deletions, and alternatives without deviating from the spirit of the invention as claimed below. For example, but not by way of limitation, the serpentine pathway in the heat exchange plate may be a coil or other suitable configuration, or the sensors may sense a wide variety of body locations and other parameters may be provided to the processor, such as temperature or pressure. Further, the in-dwelling heat exchanger at the end of the catheter may be any appropriate type, such as a non-balloon heating/cooling element. An appropriate pump might be provided that is a screw pump, a gear pump, a diaphragm pump, a peristaltic roller pump, or any other suitable means for pumping the heat exchange fluid. All of these and other substitutions obvious to those of skill in the art are contemplated by this invention.

While particular embodiments of the invention have been described above, for purposes of or illustration, it will be evident to those skilled in the art that numerous variations of the above-described embodiments may be made without departing from the invention as defined in the appended claims.

What is claimed is:

1. A heat transfer catheter flow system, comprising:
   a heat transfer medium circulation loop including a heat transfer catheter insertable within a patient, a heat transfer unit, and conduits coupled to the heat transfer catheter and heat transfer unit that enable circulation of a heat transfer medium therebetween;
   a pump head in contact with heat transfer medium within the circulation loop for circulating heat transfer medium through the circulation loop;
   a cassette including the heat transfer unit and containing the pump head;
   a controller with which the cassette mates, the controller including a control circuit and a pump motor, wherein the pump head engages the pump motor when the cassette mates with the controller; and
   an electronic feedback loop that detects a backed torque experienced by the pump motor and provides feedback to the control circuit that in turn controls the speed of the pump motor.

2. The system of claim 1, wherein the controller includes a cavity for receiving the cassette, and wherein the heat transfer unit includes an external heat exchanger including an outer flexible layer at least partly defining a flow channel therein, the flexible layer expanding outward upon flow of heat exchange medium through the flaw channel, wherein the controller includes a heat and/or cold generating element facing the cavity that exchanges heat with the heat exchange medium in the flow channel through the flexible layer, the cavity being sized such that outward expansion of the flexible layer causes the external heat exchanger to be compressively retained within the cavity.

3. The system of claim 1, wherein the controller includes a cavity for receiving the cassette, the pump motor being positioned adjacent the opening of the cavity.

* * * * *

UNITED STATES PATENT AND TRADEMARK OFFICE
CERTIFICATE OF CORRECTION

| | |
|---|---|
| PATENT NO. | : 7,879,077 B2 |
| APPLICATION NO. | : 11/674119 |
| DATED | : February 1, 2011 |
| INVENTOR(S) | : Timothy R. Machold et al. |

It is certified that error appears in the above-identified patent and that said Letters Patent is hereby corrected as shown below:

Title page, (12), delete "MacHold et al." and insert instead --Machold et al.--.

Title page, (75) Inventors, please delete "MacHold" and insert instead --Machold--.

Column 5, line 58, between "of" and "patient" insert --the--.

Column 6, line 31, after "controller" insert --.--.

Column 7, line 60, after "exchange" delete ".".

Column 10, line 21, after "body" insert --.--.
　　　　　line 28, after "response" insert --.-- and after "heat" delete ",".
　　　　　line 67, after "While" insert --the--.

Column 12, line 17, after "through" delete "art" and insert instead --an--.
　　　　　line 64, between "amount" and "heat" insert --of--.

Column 19, line 49, delete "713" and insert instead --7B--.

Column 24, line 19, between "492" and "The" insert --.--.

Column 28, line 11, after "such" delete "a" and insert instead --as--.
　　　　　line 45, delete "pus" and insert instead --push--.

Column 30, line 25, delete "fall" and insert instead --full--.

Column 31, line 14, delete "1413" and insert instead --14B--.

Column 32, line 55, delete "response" and insert instead --responds--.

Signed and Sealed this
Twenty-fifth Day of September, 2012

David J. Kappos
*Director of the United States Patent and Trademark Office*

CERTIFICATE OF CORRECTION (continued)
U.S. Pat. No. 7,879,077 B2

Column 34, line 36, between "in" and "area" insert --the--.

Column 36, line 39, delete "176" and insert instead --17B--.

Column 37, line 47, delete "a" and insert instead --an--.

Column 40, line 47, between "through" and "fluid" insert --the--.
        line 55, delete "automatic" and insert instead --automatically--.

Column 41, line 35, delete "even" and insert instead --event--.
        line 67, after "shuts" insert --down--.

Column 43, line 39, between "around" and "body" insert --the--.

Column 44, line 39, delete "flaw" and insert instead --flow--.